(12) United States Patent
Hodge

(10) Patent No.: US 7,494,817 B2
(45) Date of Patent: Feb. 24, 2009

(54) METHODS FOR GENOTYPE SCREENING USING MAGNETIC PARTICLES

(75) Inventor: Timothy A. Hodge, Eads, TN (US)

(73) Assignee: Transnet YX, Inc., Cordova, TN (US)

( * ) Notice: Subject to any disclaimer, the term of this patent is extended or adjusted under 35 U.S.C. 154(b) by 80 days.

(21) Appl. No.: 11/173,791

(22) Filed: Jun. 30, 2005

(65) Prior Publication Data

US 2006/0014192 A1   Jan. 19, 2006

Related U.S. Application Data

(63) Continuation-in-part of application No. 09/945,952, filed on Sep. 4, 2001, now Pat. No. 7,011,943, and a continuation-in-part of application No. 11/074,995, filed on Mar. 8, 2005, now Pat. No. 7,282,361, and a continuation-in-part of application No. 11/166,990, filed on Jun. 24, 2005.

(60) Provisional application No. 60/230,371, filed on Sep. 6, 2000.

(51) Int. Cl.
  *G01N 33/00* (2006.01)
  *C12M 1/34* (2006.01)
  *C07H 21/04* (2006.01)

(52) U.S. Cl. .................. 436/94; 435/287.2; 536/23.1; 536/24.3; 536/2

(58) Field of Classification Search .............. None
See application file for complete search history.

(56) References Cited

U.S. PATENT DOCUMENTS

| | | |
|---|---|---|
| 4,554,088 A | 11/1985 | Whitehead et al. |
| 4,628,037 A | 12/1986 | Chagnon et al. |
| 4,672,040 A | 6/1987 | Josephson |
| 4,695,393 A | 9/1987 | Whitehead et al. |
| 4,698,302 A | 10/1987 | Whitehead et al. |
| 4,920,213 A | 4/1990 | Dale et al. |
| 5,139,744 A | 8/1992 | Kowalski |
| 5,182,203 A | 1/1993 | Ebersole et al. |
| 5,196,306 A | 3/1993 | Bobrow et al. |
| 5,355,304 A | 10/1994 | DeMoranville et al. |
| 5,366,896 A | 11/1994 | Margrey et al. |
| 5,413,923 A | 5/1995 | Kucherlapati et al. |
| 5,489,513 A | 2/1996 | Springer et al. |
| 5,527,695 A | 6/1996 | Hodges et al. |
| 5,582,989 A | 12/1996 | Caskey et al. |
| 5,583,001 A | 12/1996 | Bobrow et al. |
| 5,596,089 A | 1/1997 | Silversides et al. |
| 5,596,092 A | 1/1997 | Schneider |
| 5,631,844 A | 5/1997 | Margrey et al. |
| 5,654,182 A | 8/1997 | Wahl et al. |
| 5,656,493 A | 8/1997 | Mullis et al. |
| 5,658,548 A * | 8/1997 | Padhye et al. ............. 423/335 |
| 5,658,744 A | 8/1997 | Ochoa et al. |
| 5,665,549 A | 9/1997 | Pinkel et al. |
| 5,677,177 A | 10/1997 | Wahl et al. |
| 5,705,628 A * | 1/1998 | Hawkins ................. 536/25.4 |
| 5,720,936 A | 2/1998 | Wadsworth et al. |
| 5,721,098 A | 2/1998 | Pinkel et al. |
| 5,731,095 A | 3/1998 | Milco et al. |
| 5,731,158 A | 3/1998 | Bobrow et al. |
| 5,733,753 A | 3/1998 | Jorgensen |
| 5,804,382 A | 9/1998 | Sytkowski et al. |
| 5,837,466 A | 11/1998 | Lane et al. |
| 5,841,975 A | 11/1998 | Layne et al. |
| 5,858,658 A | 1/1999 | Haemmerle et al. |
| 5,859,230 A | 1/1999 | Kim et al. |
| 5,863,726 A | 1/1999 | Harley et al. |
| 5,888,723 A | 3/1999 | Sutton et al. |
| 5,898,071 A * | 4/1999 | Hawkins ................. 536/25.4 |
| 5,932,780 A | 8/1999 | Soreq et al. |
| 5,942,402 A | 8/1999 | Schmidt et al. |
| 5,945,525 A * | 8/1999 | Uematsu et al. .......... 536/25.42 |
| 5,968,731 A | 10/1999 | Layne et al. |
| 5,973,138 A | 10/1999 | Collis |
| 6,027,945 A | 2/2000 | Smith et al. |
| 6,030,581 A | 2/2000 | Virtanen |
| 6,037,465 A | 3/2000 | Hillebrand et al. |

(Continued)

FOREIGN PATENT DOCUMENTS

EP    1333286 A    8/2003

(Continued)

OTHER PUBLICATIONS

Hayes et al., M.D. Computing: Computers in Medical Practice, Jul.-Aug. 1996 13 (4): 330-334; abstract only.

(Continued)

*Primary Examiner*—Bradley L Sisson
(74) *Attorney, Agent, or Firm*—Butler, Snow, O'Mara, Stevens & Cannada PLLC

(57) ABSTRACT

This invention relates to a method of an assay of genomic nucleic acid. Additionally, this invention relates to various methods to detect or screen for designated genetic sequences or portion thereof derived from a biological sample. More particularly, this invention relates to the use of magnetically responsive magnetic particles that function to reversibly bind genomic nucleic acid. A portion of the purified genomic nucleic acid is detected in solution by a variety of methods.

13 Claims, 15 Drawing Sheets

U.S. PATENT DOCUMENTS

| | | | |
|---|---|---|---|
| 6,043,039 A | 3/2000 | Bar-Am et al. | |
| 6,054,266 A | 4/2000 | Kronick et al. | |
| 6,054,270 A | 4/2000 | Southern | |
| 6,055,487 A | 4/2000 | Margery et al. | |
| 6,060,240 A | 5/2000 | Kamb et al. | |
| 6,078,902 A | 6/2000 | Schenkler | |
| 6,090,935 A | 7/2000 | Breivik et al. | |
| 6,107,032 A | 8/2000 | Kilger et al. | |
| 6,114,150 A | 9/2000 | Weissman et al. | |
| 6,117,635 A | 9/2000 | Nazarenko et al. | |
| 6,156,501 A | 12/2000 | McGall et al. | |
| 6,159,685 A | 12/2000 | Pinkel et al. | |
| 6,177,278 B1 | 1/2001 | Haj-Ahmad | |
| 6,187,537 B1 | 2/2001 | Zinn, Jr. et al. | |
| 6,192,320 B1 | 2/2001 | Margrey et al. | |
| 6,203,989 B1 | 3/2001 | Goldberg et al. | |
| 6,255,477 B1 | 7/2001 | Kleiber et al. | |
| 6,280,945 B1 | 8/2001 | U'ren | 435/6 |
| 6,291,248 B1 | 9/2001 | Haj-Ahmad | |
| 6,319,670 B1 | 11/2001 | Sigal et al. | 435/6 |
| 6,355,792 B1 | 3/2002 | Michelsen et al. | |
| 6,368,800 B1 | 4/2002 | Smith et al. | 435/6 |
| 6,376,194 B2 | 4/2002 | Smith et al. | 435/6 |
| 6,447,911 B1 | 9/2002 | Pryor et al. | 428/404 |
| 6,465,178 B2 | 10/2002 | Chappa et al. | |
| 6,480,791 B1 | 11/2002 | Strathmann | 702/20 |
| 6,503,762 B1 | 1/2003 | Yamauchi et al. | 436/526 |
| 6,548,253 B1 | 4/2003 | Holschuh et al. | |
| 6,562,568 B1 | 5/2003 | Kleiber et al. | 435/6 |
| 6,607,667 B2 | 8/2003 | Pryor et al. | 210/263 |
| 6,618,679 B2 | 9/2003 | Loehrlein et al. | 702/20 |
| 6,673,631 B1 | 1/2004 | Tereba et al. | |
| 6,699,987 B2 | 3/2004 | Hillebrand et al. | |
| 6,977,178 B2 | 12/2005 | Hodge et al. | |
| 7,011,943 B2 | 3/2006 | Hodge | |
| 7,045,367 B2 * | 5/2006 | Kaganove et al. | 436/532 |
| 7,098,320 B1 * | 8/2006 | Mirkin et al. | 536/23.1 |
| 2002/0012934 A1 | 1/2002 | Meghan et al. | |
| 2002/0012936 A1 | 1/2002 | Lorincz et al. | 435/6 |
| 2002/0081714 A1 | 6/2002 | Jain et al. | |
| 2002/0086326 A1 | 7/2002 | Smith et al. | 435/6 |
| 2002/0119455 A1 | 8/2002 | Chan | |
| 2002/0160361 A1 | 10/2002 | Loehrlein et al. | 435/6 |
| 2003/0003460 A1 | 1/2003 | Sigal et al. | 435/6 |
| 2003/0082571 A1 | 5/2003 | Kachab et al. | 435/6 |
| 2003/0082605 A1 | 5/2003 | Hodge | |
| 2003/0087286 A1 | 5/2003 | Hodge | |
| 2003/0165922 A1 | 9/2003 | Hodge et al. | |
| 2003/0170613 A1 | 9/2003 | Straus | 435/5 |
| 2003/0204322 A1 | 10/2003 | Loehrlein et al. | 702/20 |
| 2003/0207289 A1 | 11/2003 | Hodge et al. | |
| 2003/0207295 A1 | 11/2003 | Gunderson et al. | 435/6 |
| 2003/0207296 A1 | 11/2003 | Park et al. | 435/6 |
| 2003/0215821 A1 | 11/2003 | Gunderson et al. | 435/6 |
| 2004/0086930 A1 | 5/2004 | Tereba | |
| 2005/0170423 A1 | 8/2005 | Hodge | |
| 2005/0221370 A1 | 10/2005 | Hodge | |
| 2005/0239125 A1 | 10/2005 | Hodge | |
| 2005/0266494 A1 | 12/2005 | Hodge | |
| 2005/0272085 A1 | 12/2005 | Hodge | |
| 2005/0287583 A1 | 12/2005 | Smith | |
| 2006/0014186 A1 | 1/2006 | Hodge | |
| 2006/0014192 A1 | 1/2006 | Hodge | |

FOREIGN PATENT DOCUMENTS

| | | |
|---|---|---|
| WO | WO 91/12079 | 8/1991 |
| WO | WO 93/03150 A | 2/1993 |
| WO | WO 93/25709 | 12/1993 |
| WO | WO 94/11838 | 5/1994 |
| WO | WO 96/05488 | 2/1996 |
| WO | WO 98/39475 | 9/1998 |
| WO | WO 99/02667 | 1/1999 |
| WO | WO 00/40593 | 7/2000 |

OTHER PUBLICATIONS

A. Diagger & Co. Catalog, 1999, pp. 528, 542, 543.

Research Genetics (advertisement), Nucleic Acids Research, Aug. 1994, 22(5).

Charles Rivers Genetic Testing Services Order Form—"Transfer and Validation of PCR Assay of Transgenic Rodents".

Charles Rivers Genetic Testing Services Order Form—"Transfer and Validation of Southern Blot Assay of Transgenic Rodents".

Zhang et al., Bioinformatics, vol. 19, No. 1, 2003, pp. 14-21.

Research Genetics, "Designer PCR," Nucleic Acids Research, vol. 22, No. 15, Aug. 11, 1994.

Levison et al., "Recent Developments of Magnetic Beads for use in Nucleic Purification," Journal of Chromatography A, 816(1998) 107-111.

Wu et al., "Methods in gene biotechnology, Chapter 17: New strategies for gene knockout", Methods in Gene Biotechnology, 1997, p. 339-365.

Fu et al., "Rapid determination of transgene copy number in stably-transfected mammalian cells by competitive PCR,". Journal of Biochemical and Biophysical Methods, Aug. 12, 1999, p. 101-112, vol. 40, No. 3, Netherlands.

Drazan et al., "Viral IL-10 gene therapy inhibits TNF-alpha and IL-1 beta, not IL-6, in the newborn endotoxemic mouse,". Journal of Pediatric Surgery, Mar. 1996, p. 411-414, vol. 31, No. 3, United States of America.

Zhang et al., "Gene transfer expression and inheritance of PRSV-rainbow trout-GH complementary DNA in the common carp cyprinus-carpio linnaeus,". Molecular Reproduction and Development, 1990, p. 3-13, vol. 25, No. 1.

Egashira et al, "Visible integration of the adenosine deaminase (ADA) gene into the recipient genome after gene therapy,". American Journal of Medical Genetics, Jan. 23, 1998, p. 314-317, vol. 75, No. 3.

Weaver et al., "A recurring pattern of chromosomal aberrations in mammary gland tumors of MMTV-cmyc transgenic mice," Gene Chromosomes and Cancer, Jul. 1999, p. 251-260, vol. 25, No. 3.

Ma et al., "Owl Monkey Gene Map Evidence for a Homologous Human Chromosome 7Q Region Near the Cystic Fibrosis Locus," Genomics, 1989, p. 389-396, vol. 5, No. 3.

Asahida et al., "Tissue preservation and total DNA extraction from fish stored at ambient temperature using buffers containing high concentration of urea," Fisheries Science, 1996, p. 727-730, vol. 62, No. 5, Tokyo.

* cited by examiner

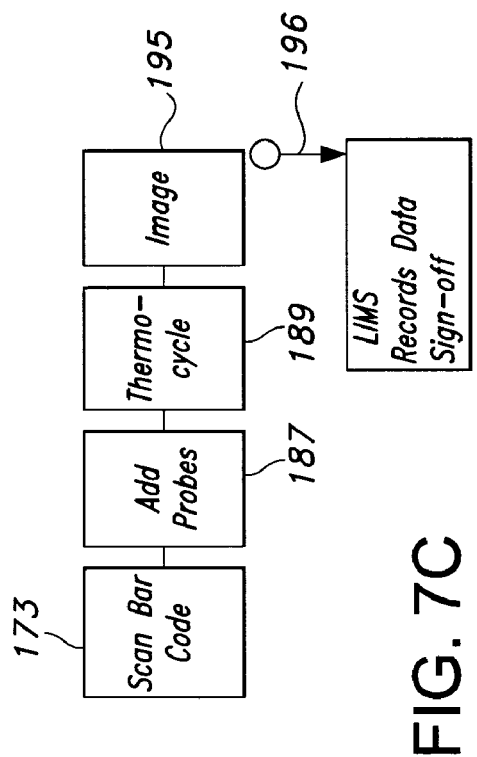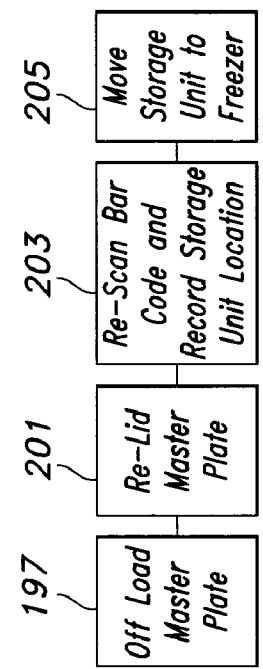

SEQUENCE LISTING

<160> NUMBER OF SEQ ID NOS: 22

<210> SEQ ID NO 1
<211> LENGTH: 792
<212> TYPE: DNA
<213> ORGANISM: Mus sp.

<400> SEQUENCE: 1
cattgaacaa gatggattgc acgcaggttc tccggccgct tgggtggaga ggctattcgg     60
ctatgactgg gcacaacaga caatcggctg ctctgatgcc gccgtgttcc ggctgtcagc    120 gcagggcgc ccggttcttt ttgtcaagac cgacctgtcc ggtgccctga atgaactgca    180
ggacgaggca gcgcggctat cgtggctggc cacgacgggc gttccttgcg cagctgtgct    240
cgacgttgtc actgaagcgg gaagggactg gctgctattg ggcgaagtgc cggggcagga    300
tctcctgtca tctcaccttg ctcctgccga gaaagtatcc atcatggctg atgcaatgcg    360
gcggctgcat acgcttgatc cggctacctg cccattcgac caccaagcga aacatcgcat    420
cgagcgagca cgtactcgga tggaagccgg tcttgtcgat caggatgatc tggacgaaga    480
gcatcagggg ctcgcgccag ccgaactgtt cgccaggctc aaggcgcgca tgcccgacgg    540
cgaggatctc gtcgtgaccc atggcgatgc ctgcttgccg aatatcatgg tggaaaatgg    600
ccgcttttct ggattcatcg actgtggccg gctgggtgtg gcggaccgct atcaggacat    660
agcgttggct acccgtgata ttgctgaaga gcttggcggc gaatgggctg accgcttcct    720
cgtgctttac ggtatcgccg ctcccgattc gcagcgcatc gccttctatc gccttcttga    780
cgagttcttc tg    792

<210> SEQ ID NO 2
<211> LENGTH: 71
<212> TYPE: DNA
<213> ORGANISM: Mus sp.

<400> SEQUENCE: 2
attgccttgt aagcgatgtg attctattgg atggagaggc tattcggcta tgactgggca     60
caacagacaa t    71

<210> SEQ ID NO 3
<211> LENGTH: 70
<212> TYPE: DNA
<213> ORGANISM: Mus sp.

<400> SEQUENCE: 3
cgggtcagta tcggcttatc ggagaggtag gttatcttag tgtagcgaat gttccgttac    60
aacagacaat                                                          70

<210> SEQ ID NO 4
<211> LENGTH: 71
<212> TYPE: DNA
<213> ORGANISM: Mus sp.

<400> SEQUENCE: 4
attgccttgt aagcgatgtg attctattgg atggagaggc tattcggcta tgactgggca    60
caacagacaa t                                                        71

<210> SEQ ID NO 5
<211> LENGTH: 71
<212> TYPE: DNA
<213> ORGANISM: Mus sp.

<400> SEQUENCE: 5
taacagacaa cacgggtcag tatcggctta tcggagaggt aggttatctt agtgtagcga    60
atgttccgtt a                                                        71

<210> SEQ ID NO 6
<211> LENGTH: 66
<212> TYPE: DNA
<213> ORGANISM: Mus sp.

<400> SEQUENCE: 6
attgccttgt aagcgatgtg attctattgg atggagaggc tattcggcta tgactgggca    60
caacag                                                              66

<210> SEQ ID NO 7
<211> LENGTH: 35
<212> TYPE: DNA
<213> ORGANISM: Mus sp.

<400> SEQUENCE: 7
tggagaggct attcggctat gactgggcac aacag                              35

<210> SEQ ID NO 8
<211> LENGTH: 31
<212> TYPE: DNA
<213> ORGANISM: Mus sp.

<400> SEQUENCE: 8
attgccttgt aagcgatgtg attctattgg a                                  31

<210> SEQ ID NO 9
<211> LENGTH: 31
<212> TYPE: DNA
<213> ORGANISM: Mus sp.

<400> SEQUENCE: 9
tccaatagaa tcacatcgct tacaaggcaa t                                  31

<210> SEQ ID NO 10
<211> LENGTH: 8831
<212> TYPE: DNA
<213> ORGANISM: Mus sp.

<400> SEQUENCE: 10

```
gagcttcggg cgaaggcccg ggagcagcgg accgaggctg gcgcgatgct gttcccgggg      60
agcgcagtcg gctaccgttg aggaaggtgg agtgaggagt ggcccttcca gcgccccta     120
tgtacgcctt cctgcgctcg gggccggtcg ccgcgttgcc cgcctccgta ccgcccgtga    180
ctctcggggc ccggagctcc ggcggcggcc gggtcgagt  cccgggggag gggaggcgcc    240
cgggcggcgc ccgagcttgc ggccgcggag cgagcgtctg gcaggtccaa gggtagccaa    300
ggatggctgc agcttcatat gatcagttgt taaagcaagt tgaggcactg aagatggaga    360
actcaaatct tcgacaagag ctagaagata attccaatca tcttacaaaa ctggaaactg    420
aggcatctaa tatgaaggaa gtacttaagc agctacaggg aagtattgaa gatgagacta    480
tgacttctgg acagattgac ttactagagc gtcttaaaga atttaactta gatagtaatt    540
tccccggagt gaaactacgc tcaaaaatgt cccttcgctc ctacggaagt cgggaaggat    600
ctgtatccag ccgttcagga gaatgcagtc ctgtccccat ggggtcattc ccaagaagaa    660
catttgtaaa tggaagcaga gagagtactg ggtatctaga agagcttgaa aaagaaagat    720
cattactcct tgctgatctt gacaaagaag agaaggaaaa ggactggtat tatgctcaac    780
ttcagaacct cacaaaaaga atagatagcc tgcctttaac tgaaaatttt tccttacaga    840
cagacatgac aagacggcag ctggagtatg aagcaaggca gatcagggct gcaatggagg    900
agcagcttgg cacctgccag acatggaga  agcgtgcaca cgaagaata  gccaggatcc    960
agcaaataga aaaggacata ctgcgcgtgc gccagctttt acagtcccag gcggcggaag   1020
cggagaggtc atctcagagc aggcatgatg ctgcctccca tgaagctggc cggcagcacg   1080
aaggccacgg agtggcagaa agcaacaccg cagcctccag tagtggtcag agtccagcta   1140
cacgtgtgga tcacgaaaca gccagtgttt tgagttctag cggcacgcac tctgctcctc   1200
gaaggttgac aagtcatctg gggacaaagg tggaaatggt gtattccttg ttgtcaatgc   1260
ttggtactca tgataaggac gatatgtcac gaactttgct agctatgtcc agctcccaag   1320
acagctgtat atccatgcgg cagtctggat gtcttcctct cctcatccag cttttacatg   1380
gcaatgacaa agactctgta ttgttgggaa attcccgggg cagtaaagag gctcgggcca   1440
gggccagtgc agcactccac aacatcattc actcacagcc tgatgacaag agaggcaggc   1500
gtgaaatccg agtccttcat cttttggaac agatacgagc ttactgtgaa acctgttggg   1560
agtggcagga agcccacgaa caaggcatgg accaggacaa aaacccaatg ccagctcctg   1620
ttgagcatca gatctgtcct gctgtgtgtg ttctaatgaa gctttcattt gatgaagagc   1680
ataggcatga atgaatgaa  cttggggac  tgcaggccat tgcagagtta ttgcaggtgg   1740
actgtgagat gtatgggctt actaatgacc actacagtgt tactttaaga cggtatgctg   1800
gaatggcttt gacaaacttg acctttggag atgttgccaa caaggctacg ctgtgttcta   1860
tgaaaggctg catgagagca cttgtggccc agttaaaatc tgagagtgaa gacttacagc   1920
aggttattgc aagtgttttg aggaatttgt cttggcgagc agatgtaaat agcaaaaaga   1980
cgttgagaga agttggaagt gtgaaagcat tgatggaatg tgctttggaa gttaaaaagg   2040
aatcaaccct caaaagcgtt ttgagtgcct tatggaacct gtctgcacac tgcactgaga   2100
ataaggctga catctgtgct gtggatggag cactggcatt tctggttggc accctcactt   2160
```

```
accggagcca gacaaatact ttagccatta ttgaaagtgg aggtgggata ttacggaatg    2220
tgtccagctt gatagctaca acgaagacc  acaggcaaat cctaagagag aacaattgcc    2280
tacaaacttt attacagcac ttgaaatctc acagcttgac aatagtcagt aatgcatgtg    2340
gaactttgtg gaatctctca gcaagaaatc ctaaagacca ggaagccttg tgggacatgg    2400
gggcagtgag catgctcaag aacctcattc attccaagca caaatgatt  gccatgggaa    2460 gtgcagcagc tttaaggaat ctcatggcaa acagacctgc aaagtataag gatgccaata    2520
tcatgtctcc cggctcaagt ctgccatccc ttcacgttag gaaacagaaa gctctagaag    2580
ctgagctaga tgctcagcat ttatcagaaa ccttcgacaa cattgacaac ctaagtccca    2640
aggcctctca ccggagtaag cagagacaca agcagaatct ttatggtgac tatgcttttg    2700
acgccaatcg acatgatgat agtaggtcag acaatttcaa tactggaaac atgactgttc    2760
tttcaccata tttaaatact acggtattgc ccagctcttc ttcctcaagg ggaagtttag    2820
acagttctcg ttctgagaaa gacagaagtt tggagagaga gcgaggtatt ggcctcagtg    2880
cttaccatcc aacaacagaa aatgcaggaa cctcatcaaa acgaggtctg cagatcacta    2940
ccactgcagc ccagatagcc aaagttatgg aagaagtatc agccattcat acctcccagg    3000
acgacagaag ttctgcttct accaccgagt tccattgtgt ggcagacgac aggagtgcgg    3060
cacgaagaag ctctgcctcc cacacacact caaacacata caacttcact aagtcggaaa    3120
attcaaatag acatgctctc atgccttatg ccaaagtgga atataaacga tcttcaaatg    3180
acagtttaaa tagtgtcact agtagtgatg gatatgtaa  aagaggccaa atgaaaccct    3240
cagttgaatc ctattctgaa gatgatgaaa gtaaattttg cagttatggt cagtatccag    3300
ctgacctagc ccataagata cacagtgcaa atcatatgga tgataatgat ggagaactgg    3360
atacaccaat aaattacagt cttaaatatt cagatgagca gttgaactca ggaaggcaga    3420
gtccctcaca gaatgaaagg tgggcaagac caaagcatgt gatagaagat gaaataaagc    3480
aaaacgagca aagacaagca agaagccaga acaccagtta tcctgtctat tctgagaata    3540
ccgatgacaa acacctcaaa ttccaaccac attttggaca caagaatgt  gtttccccat    3600 ataggtcaag gggaaccagt ggttcagaaa caaatcgaat gggttctagt catgcaatta    3660
atcaaaatgt aaaccagtct ctgtgtcagg aagatgatta tgaagatgat aaacctacca    3720
actacagtga acgttattct gaggaagaac aacatgaaga agaagaagag agaccgacaa    3780
attatagcat aaaatataat gaagagaaac atcatgtgga tcagcctatt gattatagtt    3840
taaaatatgc cactgacatt tcttcctcac aaaaaccatc attttcattc tcaaagaatt    3900
catcagcaca aagcactaaa cctgaacatc tctctccaag cagcgagaat acagctgtac    3960
ctccatctaa tgccaaaagg cagaatcagc tgcgtccaag ttcagcacaa agaaatggcc    4020
agactcaaaa aggcactact tgcaaagtcc cctccatcaa ccaagaaaca atacagactt    4080
actgcgtaga agacaccca  atatgttttt caaggtgcag ttcattatca tcactgtcat    4140
cagctgacga tgaaatagga tgtgatcaga acacagga  agcagattct gctaatactc    4200
tgcagacagc agaagtaaaa gagaatgatg taactcggtc agctgaagat cctgcaactg    4260
aagttccagc agtgtcccag aatgctgag  ccaaacccag ccgactccag gcttctggct    4320
tatcttcaga atcaaccagg cataataaag ctgttgagtt ttcttcagga gccaagtctc    4380
cctccaaaag tggtgctcag acaccccaaa gtcccccaga acactatgtc caggagactc    4440
cgctcgtatt cagcaggtgt acttctgtca gctcccttga cagttttgag agtcgctcca    4500
```

```
ttgccagctc tgttcagagt gagccatgta gtggaatggt gagtggcatc ataagcccca    4560
gtgaccttcc agatagtcct gggcagacca tgccaccaag cagaagcaaa acccctccac    4620
ctcctccaca gacagtgcag gccaagagag aggtgccaaa aagtaaagtc cctgctgctg    4680
agaagagaga gagtgggcct aagcagactg ctgtaaatgc tgccgtgcag agggtgcagg    4740
tccttccaga cgtggatact tgttacact tcgccacaga aagtactcca gacgggtttt    4800
cttgttcctc cagcctaagt gctctgagcc tggatgagcc atttatacag aaagatgtag    4860
aattaagaat catgcctcca gttcaggaaa cgacaatgg gaatgaaact gaatcagaac    4920
agcctgagga atcaaatgaa aaccaggata agaggtaga aaagcctgac tctgaaaaag    4980
acttattaga tgattctgat gacgatgata ttgaaatatt agaagaatgt attatttcag    5040
ccatgccaac aaagtcatca cgcaaagcca aaaactagc ccagactgct tcaaaattac    5100
ctccacctgt ggcaaggaaa ccaagtcagc tacctgtgta taaacttctg ccagcacaga    5160
ataggctgca ggcacaaaaa catgttagct ttacaccagg ggatgatgtg ccccgggtgt    5220
actgtgtaga agggacacct ataaactttt ccacagcaac gtctctaagt gatctgacaa    5280
tagagtcccc tccaaatgaa ttggctactg gagatgggt cagagcgggt atacagtcag    5340
gtgaatttga aaaacgagat accattccta cagaaggcag aagtacagat gatgctcagc    5400
gaggaaaaat ctcatctata gttacaccag acctggatga caacaaagca gaggaaggag    5460
atattcttgc agaatgtatc aattctgcta tgcccaaagg aaaaagccac aagcctttcc    5520
gagtgaaaaa gataatggac caagtccaac aagcatcctc gacttcatct ggagctaaca    5580
aaaatcaagt agacactaag aaaaagaagc ctacttcacc agtaaagccc atgccacaaa    5640
atactgaata tagaacgcgt gtgagaaaga atacagactc aaaagttaat gtaaatactg    5700
aagaaacttt ctcagacaac aaagactcaa agaaaccaag cttacaaacc aatgccaagg    5760
ccttcaatga aaagctacct aacaatgaag acagagtgcg ggggagcttc gccttggact    5820
caccgcatca ctacaccct attgagggga cgccgtactg cttttcccga aatgactcct    5880
tgagttctct ggattttgat gatgacgatg ttgacctttc cagggaaaag gccgagttaa    5940
gaaagggcaa agaaagcaag gattccgaag ccaaagttac ctgccgccca gaaccaaact    6000
caagccagca ggcagctagt aagtcacaag ccagtataaa acatccagca aacagagcac    6060
agtccaaacc agtgctgcag aaacagccca cttccccca gtcctccaaa gacggaccag    6120 atagagggc agcaactgac gaaaaactgc agaattttgc tattgaaaat actccagttt    6180
gcttttctcg aaattcctct ctgagttccc ttagtgacat tgaccaggaa aacaacaata    6240
acaaagaaag tgaaccaatc aaagaagctg aacctgccaa ctcacaagga gagcccagta    6300
agcctcaggc atccgggtat gctcccaagt ccttccacgt cgaagacacc cctgtctgtt    6360
tctcaagaaa cagctctctc agttctctta gcattgactc tgaggacgac ctgttacagg    6420
agtgtataag ttctgccatg ccaaaaaaga aaggccttc aagactcaag agtgagagcg    6480
aaaagcagag ccctagaaaa gtgggtggca tattagctga agacctgacg cttgatttga    6540
aagatctaca gaggccagat tcagaacacg ctttctcccc cgactcagaa aattttgact    6600
ggaaagctat tcaggaaggc gcaaactcca tagtaagtag tttgcaccaa gctgctgcag    6660
ccgccgcgtg cttatctaga caagcgtcat ccgactcaga ttccattctg tcactaaagt    6720
ccggcatttc tctgggatcg ccttttcatc ttacacctga tcaagaggaa aagccattca    6780
caagcaataa aggcccaaga attctcaaac ctggagagaa aagcacatta gaagcaaaaa    6840
aaatagaatc tgaaaacaaa ggaatcaaag gcgggaaaaa ggtttataaa agcttgatta    6900
```

```
cgggaaagat tcgctccaat tcagaaattt ccagccaaat gaaacaaccc ctcccgacaa    6960
acatgccttc aatctcaaga ggcaggacga tgattcacat cccagggctt cggaatagct    7020
cctctagtac aagccctgtc tctaagaaag gcccacccct caagactcca gcctctaaaa    7080
gccccagtga agggccggga gctaccactt ctcctcgagg aactaagcca gcaggaaagt    7140
cagagcttag ccctatcacc aggcaaactt cccaaatcag tgggtcaaat aaggggtctt    7200
ctagatcagg atctagagac tccactccct caagacctac acagcaacca ttaagtaggc    7260
caatgcagtc tccagggcga aactcaattt cccctggtag aaatggaata agccctccta    7320
acaaactgtc tcagctgccc agaacatcat ctcccagtac tgcttcaact aagtcctccg    7380
gttctgggaa aatgtcatat acatcccag gtagacagct gagccaacaa atcttacca     7440 aacaagcaag tttatccaag aatgccagca gtatcccag aagtgagtcg gcatctaaag    7500
gactgaatca gatgagtaac ggcaatgggt caaataaaaa ggtagaactt tctagaatgt    7560
cttcaactaa atcaagtgga agtgaatcag acagatcaga aaggcctgca ttagtacgcc    7620
agtctacttt catcaaagaa gccccaagcc caaccctgag gaggaaactg gaggaatctg    7680
cctcatttga atccctttct ccatcttcta gaccagattc tcccaccagg tcgcaggcac    7740 agacccagt tttaagccct tcccttcctg atatgtctct gtccacacat ccatctgttc     7800
aggcaggtgg gtggcgaaag ctcccgccta atctcagccc cactatcgag tataatgacg    7860
gaaggcccac aaaacggcat gatattgcac gctcccattc tgaaagtcct tccagactac    7920
caatcaaccg ggcgggaacc tggaagcgtg aacacagcaa acattcctcg tcccttcctc    7980
gagtgagtac ttggagaaga actggaagct catcttctat tctttctgct tcatcagagt    8040
ccagtgaaaa agcaaaaagt gaggatgaaa ggcatgtgag ctccatgcca gcacccagac    8100
agatgaagga aaaccaggtg cccaccaaag gaacatggag gaaaatcaag gaaagtgaca    8160
tttctcccac aggcatggct tctcagagcg cttcctcagg tgctgccagt ggtgctgaat    8220
ccaagcctct gatctatcag atggcacctc ctgtctctaa aacagaggat gtttgggtga    8280
gaattgagga ctgcccccatt aacaacccta gatctggacg tcccccaca ggcaacaccc    8340 ccccagtgat tgacagtgtt tcagagaagg gaagttcaag cattaaagat tcaaaagaca    8400
cccatgggaa acagagtgtg ggcagtggca gtcctgtgca aaccgtgggt ctggaaaccc    8460
gcctcaactc ctttgttcag gtagaggccc cagaacagaa aggaactgag gcaaaaccag    8520
gacagagtaa cccagtctct atagcagaga ctgctgagac gtgtatagca gagcgtaccc    8580 cttttcagttc cagtagctcc agcaagcaca gctcacctag cgggactgtt gctgccagag    8640
tgacaccttt taattacaac cctagcccta ggaagagcag cgcagacagc acttcagccc    8700
ggccgtctca gatccctacg ccagtgagca ccaacacgaa gaagagagat tcgaagactg    8760
acagcacaga atccagtgga gcccaaagtc ctaaacgcca ttccgggtct tacctcgtga    8820
cgtctgttta a                                                        8831

<210> SEQ ID NO 11
<211> LENGTH: 686
<212> TYPE: DNA
<213> ORGANISM: Mus sp.
<220> FEATURE:
<221> NAME/KEY: misc_feature
<222> LOCATION: (561)..(585)
<223> OTHER INFORMATION: n is a, c, g, or t

<400> SEQUENCE: 11
```

-continued

```
tatcatgtct cccggctcaa gtctgccatc ccttcacgtt aggaaacaga aagctctaga      60
agctgagcta gatgctcagc atttatcaga aaccttcgac aacattgaca acctaagtcc     120
caaggcctct caccggagta agcagagaca caagcagaat ctttatggtg actatgcttt     180
tgacgccaat cgacatgatg atagtaggtc agacaatttc aatactggaa acatgactgt     240
tctttcacca tatttaaata ctacggtatt gcccagctct tcttcctcaa ggggaagttt     300
agacagttct cgttctgaga aagacagaag tttggagaga gagcgaggta ttggcctcag     360
tgcttaccat ccaacaacag aaaatgcagg aacctcatca aaacgaggtc tgcagatcac     420
taccactgca gcccagatag ccaaagttat ggaagaagta tcagccattc atacctccca     480
ggacgacaga agttctgctt ctaccaccga gttccattgt gtggcagacg acaggagtgc     540
ggcacgaaga agctctgcct nnnnnnnnnn nnnnnnnnnn nnnnncttca ctaagtcgga     600
aaattcaaat aggacatgct ctatgcctta tgccaaagtg gaatataaac gatcttcaaa     660
tgacagttta aatagtgtca ctagta                                          686

<210> SEQ ID NO 12
<211> LENGTH: 36
<212> TYPE: DNA
<213> ORGANISM: Mus sp.

<400> SEQUENCE: 12
cgatgtgatt ctattggaaa gttaggagag agagcg                                36

<210> SEQ ID NO 13
<211> LENGTH: 13
<212> TYPE: DNA
<213> ORGANISM: Mus sp.

<400> SEQUENCE: 13
atcttagtgt agc                                                         13

<210> SEQ ID NO 14
<211> LENGTH: 22
<212> TYPE: DNA
<213> ORGANISM: Mus sp.

<400> SEQUENCE: 14
tggaaagtta ggagagagag cg                                               22

<210> SEQ ID NO 15
<211> LENGTH: 36
<212> TYPE: DNA
<213> ORGANISM: Mus sp.

<400> SEQUENCE: 15
gcgagagaga ggattgaaag gttatcttag tgtagc                                36

<210> SEQ ID NO 16
<211> LENGTH: 18
<212> TYPE: DNA
<213> ORGANISM: Mus sp.

<400> SEQUENCE: 16
aagttaggag agagagcg                                                    18

<210> SEQ ID NO 17
<211> LENGTH: 18
<212> TYPE: DNA
<213> ORGANISM: Mus sp.
```

```
<400> SEQUENCE: 17
cgatgtgatt ctattgga                                                    18

<210> SEQ ID NO 18
<211> LENGTH: 31
<212> TYPE: DNA
<213> ORGANISM: Mus sp.

<400> SEQUENCE: 18
tccaatagaa tcacatcgct tacaaggcaa t                                     31

<210> SEQ ID NO 19
<211> LENGTH: 25
<212> TYPE: DNA
<213> ORGANISM: Mus sp.

<400> SEQUENCE: 19
tggagaggct attcggctat gactg                                            25

<210> SEQ ID NO 20
<211> LENGTH: 12
<212> TYPE: DNA
<213> ORGANISM: Mus sp.

<400> SEQUENCE: 20
tatcggagag gt                                                          12

<210> SEQ ID NO 21
<211> LENGTH: 13
<212> TYPE: DNA
<213> ORGANISM: Mus sp.

<400> SEQUENCE: 21
tcggctatga ctg                                                         13

<210> SEQ ID NO 22
<211> LENGTH: 20
<212> TYPE: DNA
<213> ORGANISM: Mus sp.

<400> SEQUENCE: 22
tcggctatga ctgttttcg                                                   20
```

US 7,494,817 B2

METHODS FOR GENOTYPE SCREENING USING MAGNETIC PARTICLES

CROSS-REFERENCE TO RELATED APPLICATIONS

This application claims priority under 35 U.S.C. § 120 as a CONTINUATION-IN-PART APPLICATION of U.S. patent application Ser. No. 09/945,952 which was filed on Sep. 4, 2001, and issued Mar. 14, 2006 into U.S. Pat. No. 7,011,943, as a CONTINUATION-IN-PART APPLICATION of U.S. patent application Ser. No. 11/074,995 which was filed Mar. 8, 2005, and issued Oct. 16, 2007 into U.S. Pat. No. 7,282,361, and as a CONTINUATION-IN-PART APPLICATION of Ser. No. 11/166,990 which was filed on Jun. 24, 2005, the entire disclosures of which are incorporated herein by reference for all that it teaches. U.S. patent application Ser. No. 09/945,952 also claims priority under 35 U.S.C. § 119(e), based on U.S. Provisional Application Ser. No. 60/230,371, filed Sep. 6, 2000, the entire disclosure of which is incorporated herein by reference for all that it teaches.

FIELD OF THE INVENTION

This invention relates to methods for genotype screening. More specifically, this invention relates to various methods to detect or screen for at least one designated genetic sequences in a plurality of biological samples, such as tissues and cells.

BACKGROUND OF THE INVENTION

Genomic modification resulting from mutations in the DNA of an organism can be transferred to the progeny if such mutations are present in the gametes of the organism, referred to as germ-line mutations. These mutations may arise from genetic manipulation of the DNA using recombinant DNA technology or may be introduced by challenging the DNA by chemical or physical means. DNA introduced via recombinant DNA technology can be derived from many sources, including but not limited to DNA from viruses, mycoplasm, bacteria, fungi, yeast, and chordates including mammals such as humans.

Recombinant DNA technology allows for the introduction, deletion or replacement of DNA of an organism. Random introduction of DNA into a cell can be achieved by technologies such as transfection (including electroporation, lipofection), injection (pronuclear injection, nuclear transplantation) or transduction (viral infection). Random mutations (point mutations, deletions, amplifications) can be generated by treatment of cells with chemical mutagens or submitting them to physical insult such as X-irradiation or linear energy transfer irradiation (LET). Targeted addition, deletion or replacement of DNA in an organism (either inducible or non-inducible) is achieved via homologous recombination. Inducible systems employ sequence-specific recombinases such as Cre-LoxP (U.S. Pat. Nos. 5,654,182 and 5,677,177) and FLP/FRT (U.S. Pat. No. 5,527,695).

Transgenic organisms are organisms that carry DNA sequences (be it genes or gene segments) derived from another or the same species, stably integrated randomly into their genome. Transgenic mammals are generally created by microinjection of DNA into the pronucleus of fertilized eggs, a technique in which the number of DNA copies or the integration site of the DNA into the host genome is uncontrollable. A transgenic line or strain refers to an organism that transmits the foreign DNA sequences to its offspring.

Genotype screening is used to determine if a genome possesses specific genetic sequences that exist endogenously or have been modified, mutated or genetically engineered. Genomic nucleic acid is screened for these modifications, mutations or endogenous conditions. Genomic nucleic acid is challenging to work with because of its size. The genomic nucleic acid includes both coding and noncoding regions. Therefore, the genomic nucleic acid contains exons and introns, promoter and gene regulation regions, telomeres, origins or replication and nonfunctional intergenic nucleic acid. The genomic nucleic acid is a double stranded molecule which is methylated. cDNA and PCR-amplicons differs in that the molecules are much smaller. Additionally, biochemical modification events, such as methylation, do not occur with the smaller molecules. Shena, M (2000) DNA Microarrays: A Practical Approach. Oxford University Press, New York, N.Y.

Genotype screening is currently done manually. The present manual system is time-consuming and can provide variable results depending on the laboratory and even depending on skill of laboratory workers. Presently, a researcher using Southern blot technology may require greater than a week to screen a tissue sample for a transgene or a targeted mutation.

In an alternative technology, up to thirty PCR (polymerase chain reaction) can be conducted in an EPPENDORF microtube (BRINKMANN INSTRUMENTS, Westbury, N.Y.) and separated on a gel. This process in most laboratories requires 3 to 7 days. A need exists in the industry to provide a system and method for more accurate, faster and high volume genotype screening.

Additionally, as researchers continue to use transgenic species in research specific information about the progeny of the transgenic species is of vital importance. An emerging technique in mouse mutant breeding is producing 'homozygous' transgenic conditions. During the initial creation of transgenic animals the transgene sequence integrates randomly into the host genome. Moreover, the number of transgene insertions also varies. Once the transgene is established in the genome, some investigators are interested in having this/these transgene(s) on the corresponding chromosome. The preferred mechanism for getting both chromosomes to have the transgene(s), is by breeding two transgenic animals from the same strain together. The goal is to identify homozygous animals that can then be bred to each other to ensure continual homozygous progeny. Typically, such transgenic animals are difficult to genotype by traditional PCR methods as accurate quantification is not possible with fragment-based analysis.

SUMMARY OF THE INVENTION

The present invention relates a method for detecting a designated genetic sequence in a biological sample containing genomic nucleic acid. The sample of genomic nucleic acid includes at least a portion of intact genomic nucleic acid that is obtained from a separated sample using a plurality of magnetically responsive magnetic particles, and undergoes a hybridization assay including a probe specific for a portion of the genomic nucleic acid. The improvement, in one embodiment, involves detecting the probe specific for a portion of the genomic nucleic acid while it is attached to the plurality of magnetically responsive particles in solution.

The present invention also relates to a method for detecting a nucleic acid sequence including the steps of: mixing a biological sample of genomic nucleic acid with a plurality of magnetically responsive magnetic particles, placing the mixture under conditions that facilitate reversible immobilization of the genomic nucleic acid to the plurality of magnetically responsive magnetic particles; removing unattached biological sample; adding nucleic acid probes capable of hybridizing, directly or indirectly, to a portion of said genomic nucleic acid under hybridizing conditions; removing unhybridized nucleic acid probes; and detecting the hybridized nucleic acid probes in solution.

The present invention also relates to an assay for a nucleic acid sequence including the steps of: mixing a biological sample of genomic nucleic acid with a plurality of magnetically responsive magnetic particles, placing said mixture under conditions that facilitate reversible immobilization of the genomic nucleic acid to the plurality of magnetically responsive magnetic particles; removing unattached biological sample; eluting the genomic nucleic acid from the plurality magnetically responsive magnetic particles; adding nucleic acid probes capable of hybridizing to a portion of the genomic nucleic acid under hybridizing conditions to form genomic nucleic acid-nucleic acid probe duplexes; adding a plurality of magnetically responsive magnetic particles to bind the genomic nucleic acid-nucleic acid probe duplexes; removing unbound material; resuspending genomic nucleic acid-nucleic acid probe duplexes in a sufficient amount of suspension buffer to elute genomic nucleic acid-nucleic acid probes from the plurality of magnetically responsive magnetic particles; and detecting hybridized nucleic acid probes in solution.

The hybridized nucleic acid probes can be disassociated from the genomic nucleic acid prior to the step of detecting in solution in one embodiment. Additionally, the nucleic acid probes can be ligated to a dendrimer or in another embodiment the nucleic acid probes react with elements on a dendrimer, e.g. a nucleic acid probe with a hapten (biotin) attached reacts with the anti-hapten element on a dendrimer (i.e. anti-biotin). The hybridized nucleic acid probes can be directly or indirectly detected.

The speed and the sensitivity of the assay are enhanced by suspending the item to be detected in a liquid medium.

BRIEF DESCRIPTION OF THE DRAWINGS

A more complete understanding of the invention and its advantages will be apparent from the following Description of the Preferred Embodiment(s) taken in conjunction with the accompanying drawings, wherein:

FIG. 7C is a block diagram of the laboratory process system.

FIG. 7D is a block diagram of the laboratory process system.

DETAILED DESCRIPTION OF THE PREFERRED EMBODIMENTS

Figure 1:
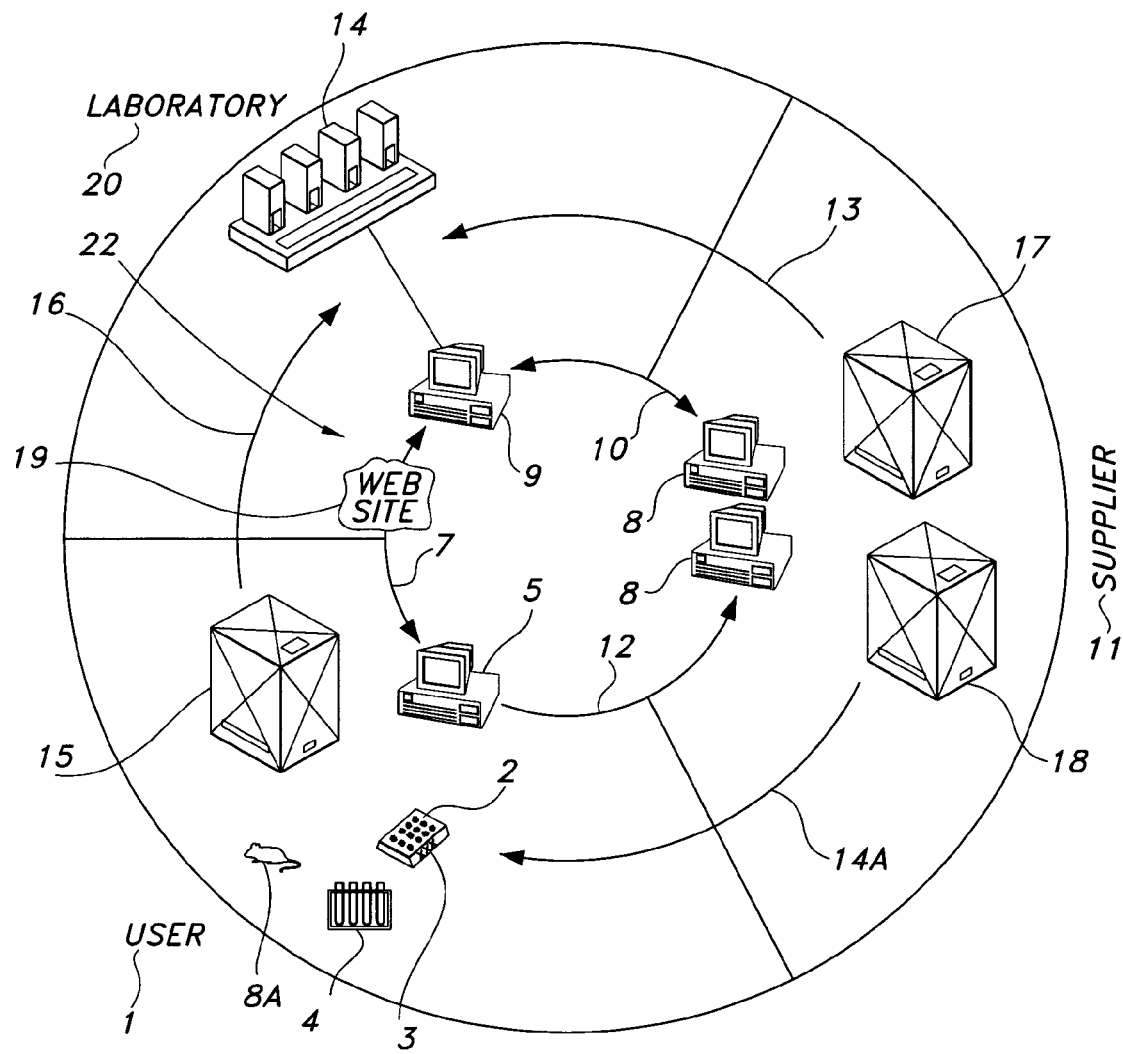
FIG. 1 is an illustrative overview of the remote automated testing procedures of the present invention.

The present invention provides a method and system for high volume genotype screening. This invention provides a method for rapid identification of an organism, whose genome possesses specific genetic sequences that exist endogenously or has been modified, mutated or genetically engineered. All patents, patent applications and articles discussed or referred to in this specification are hereby incorporated by reference.

1. DEFINITIONS

The following terms and acronyms are used throughout the detailed description.

complementary—chemical affinity between nitrogenous bases as a result of hydrogen bonding. Responsible for the base pairing between nucleic acid strands. Klug, W. S. and Cummings, M. R. (1997) *Concepts of Genetics*, fifth ed., Prentice-Hall, Upper Saddle River, N.J.

copy number—the number of transgenes that have randomly integrated into the genome.

deletion mutation—a mutation caused by the removal of one or more nucleotides from a gene or chromosome.

designated genetic sequence—includes a transgenic insert, a selectable marker, microsatellite loci, recombinant site or any gene or gene segment.

DNA (deoxyribonucleic acid)—The molecule that encodes genetic information. DNA is a double-stranded molecule held together by weak bonds between base pairs of nucleotides. The four nucleotides in DNA contain the bases: (A), guanine (G), cytosine (C), and thymine (T). In nature, base pairs form only between A and T and between G and C; thus the base sequence of each single strand can be deduced from that of its partner.

electroporation—the exposure of cells to rapid pulses of high-voltage current which renders the plasma membrane of the cells permeable and thus allowing transfection.

embryonic stem cells (ES cells)—a cell of the early embryo that can replicate indefinitely and which can differentiate into other cells; stem cells serve as a continuous source of new cells.

genome—all the genetic material in the chromosomes of a particular organism; its size is generally given as its total number of base pairs.

genomic DNA—The genomic nucleic acid includes both coding and noncoding regions. Therefore, the genomic nucleic acid contains exons and introns, promoter and gene regulation regions, telomeres, origins or replication and nonfunctional intergenic nucleic acid. The genomic nucleic acid is a double stranded molecule which is methylated. cDNA and PCR-amplicons differs in that the molecules are much smaller. Additionally, biochemical modification events, such as methylation, do not occur with the smaller molecules. Shena, M (2000) *DNA Microarrays: A Practical Approach*. Oxford University Press, New York, N.Y.

genotype—genetic constitution of an individual cell or organism that can include at least one designated genetic sequence.

germ-line—unmodified genetic material transmitted to progeny via gametes.

gene targeting—the creation of a null or mutant allele by homologous recombination or gene replacement.

inducible gene targeting—a method of gene targeting that allows the inducible inactivation (or activation) of a targeted gene by experimental manipulation, such as administration of a drug. Example: Cre recombinase is a site-specific recombinase that catalyzes the excision of DNA flanked by lox recognition sequences. Since the promoter for Cre expression is sensitive to the drug interferon, targeted deletion is inducible.

Internet—a collection of interconnected (public and/or private) networks that are linked together by a set of standard protocols to form a global, distributed network. The World Wide Web (hereinafter web) refers to both a distributed collection of interlinked, user viewable hypertext documents (commonly referred to as web pages) that are accessible via the Internet and the user and server software components which provide user access to such documents using standard Internet protocols.

line—A line is a colony bred for a genetic condition, (i.e. at least one designated genetic sequence).

mutation—a heritable change in DNA sequence resulting from mutagens. Various types of mutations including frameshift mutations, missense mutations, and nonsense mutations.

recombination—The process by which offspring derive a combination of genes different from that of either parent. In higher organisms, this can occur by crossing over.

recombinant DNA—A combination of DNA molecules of different origin that are joined using recombinant DNA technologies.

retroviral infection—retroviral vectors with recombinant DNA incorporate their genome into the chromosomes of cells it infects.

selectable marker—an approach to facilitate the detection of targeted cells by decreasing the detection of random integrants rather than increasing targeting efficiency. There are two types of selectable genes: designated and negative. A designated selector gene, such as neomycin, confers resistance to drugs normally lethal to the cell. Cells that have incorporated neomycin into their genome by homologous recombination will be resistant to the drug neomycin. Conversely, non-homologous recombination events will retain the negative selector gene. The negative selector gene, such as HSV-tk, confers sensitivity to certain drugs (cells expressing HSV-tk are sensitive to gancyclovir) resulting in cell death. A selectable marker is a genetic sequence.

site specific recombinase—an enzyme that promotes recombination between specific DNA sequences.

source well plate—The plate that remote user 1 fills with biological sample.

strain—a group of organisms bred for a genotype (at least one designated genetic sequence).

strain controls—are biomatter samples submitted by a remote use 1. Strain controls are controls positive and negative sent to the screen laboratory as the remote user that discloses the genotype.

targeted deletion—technique for inactivating a gene by deleting it from the genome. May be accomplished by homologous recombination or inducible gene targeting.

targeted mutagenesis—alteration of the germline by the introduction of a site-directed mutation.

transfection—the uptake, incorporation, and expression of recombinant DNA by eukaryotic cells.

transgene—the foreign gene or DNA.

transgenic—this term describes an organism that has had genes from another organism put into its genome through recombinant DNA techniques. These organisms are usually made by microinjection of DNA in the pronucleus of fertilized eggs, with the DNA integrating at random.

transgenic line—a transgenic mouse or organism strain in which the transgene is stably integrated into the germline and therefore inherited in Mendelian fashion by succeeding generation.

web site—a computer system that serves informational content over a network using the standard protocol of the World Wide Web. A web site corresponds to a particular Internet domain name such as TransnetYX.com.

2. OVERVIEW OF THE SYSTEMS COMPONENTS AND OPERATIONS

The present invention provides methods for genotype screening. More specifically, the present application relates to a method to rapidly screen biological samples for at least one designated genetic sequence. Various aspects of genotype screening involve: sample collection, lysing of the biological sample, isolation of a purified genomic nucleic acid and nucleic acid screening in solution. Additionally, the method operating according to the features described herein can provide screening results to a remote user 1 from the screening laboratory 20 within 24 hours of receiving the biological samples.

In order to screen for a designated genetic sequence, that sequence must first be determined or identified. Only when the designated sequence is known can a test be devised to search for its existence in the biological samples provided by the remote user 1 to the screening laboratory 20.

There are a variety of ways the designated genetic sequence can be acquired by the remote user 1 or by the screening laboratory 20. For example, if the sequence of bases that makeup the designated genetic sequence is known by the remote user 1, the sequence can be directly communicated to the screening laboratory 20 via an electronic link, such as any of the electronic communication links identified herein, and particularly the communication links extending between the remote user's computer and the screening laboratory 20.

The remote user 1 can indirectly communicate the designated genetic sequence to the screening laboratory 20 by communicating a publication, journal article, a gene name, a sequence name, a line or strain name (if the designated genetic sequence is found in animals of that line or strain), or the name of a mutation having the designated genetic sequence to the screening laboratory 20. Alternatively, the remote user 1 can communicate to the screening laboratory 20 the sequence of a probe that corresponds to a target genetic sequence of the designated genetic sequence. These probes will have previously been created or defined to indicate the presence of the designated genetic sequence.

The indirect references may provide the entire sequence. Alternatively, the screening laboratory 20 may take the information from the references or from the remote user 1 and use it to search public genetic databases such as The National Center for Biotechnology Information (NCBI), ENSEMBL, or The Wellcome Trust Sanger Institute database. The screening laboratory 20 can also search proprietary databases, such as the database provided by Celera Bioscience (Rockville, Md.).

Another indirect method that may be used to acquire or identify the designated genetic sequence is to use a third party who has specific knowledge of the sequence. For example, the screening laboratory 20 can receive the name of a transgenic animal line or strain from the remote user 1, then contact the company that engineers that line or strain. The company can then transmit the sequence of bases that constitute the particular genetic sequence corresponding to that line or strain back to the screening laboratory 20. These companies include such firms as LEXICON GENETICS (Woodland, Tex.) or CHARLES RIVER LABORATIES (Wilmington, Mass.). Even further, individual researchers who have developed the line or strain, or who work with the same line or strain at another laboratory may provide the designated genetic sequence or the probes necessary to identify the designated genetic sequence.

If the designated genetic sequence is not known by the remote user 1 or third party and is not found in any public or private database, the screening laboratory 20 may use scientific methods. If the remote user 1 has a working genotyping assay, and they are performing PCR and separating fragments in a gel, the appropriate bands can be cut from the gel, purified and sequenced to determine the sequence of bases in that band. The company sequencing the bands can directly communicate the base sequence to the screening laboratory 20 or to the remote user 1, who in turn can communicate the base sequence to the screening laboratory 20.

Once identity of the designated genetic sequence is acquired by the screening laboratory 20 (and assuming the probe has yet to be designed), the screening laboratory 20 must then select a target genetic sequence of the designated genetic sequence for which a probe can be constructed. In the preferred embodiment, the sequence of the probe is determined using software such as OLIGO TECH (OLIGOS ETC Inc, Wilsonville, Oreg.). The target genetic sequence may be directly selected from the designated genetic sequence by the screening laboratory 20. Once selected, the base sequence corresponding to the target genetic sequence is communicated to an oligonucleotide vendor, who manufactures the probes and transmits them to the screening laboratory 20. These oligonucleotides or probes may be directly ligated to the fluorescent dendrimer molecules by the screening laboratory. Alternatively, the oligonucleotides my be transmitted to another reagent vendor such as GENISPHERE (Hatfield, Pa.) to have the oligonucleotide probes ligated to fluorescent molecules such as a dendrimer.

The screening laboratory 20 preferably keeps a supply of probes on hand so each future request by the remote user need not require special production of probes.

Alternatively, a special probe may be required. In that situation, the screening laboratory 20 may not select the target genetic sequence itself, but may communicate to a third party specific areas in the designated genetic sequence that are important for mutation detection. The third party is typically an oligonucleotide vendor, who in turn will select the target genetic sequence, manufacture the probes and send the probes to the screening laboratory 20.

Zygosity genotyping of samples may require special probes. One probe is built for the designated genetic sequence of a mutation, while another probe is built for the designated genetic sequence of the specific endogenous loci. Zygosity testing includes identifying not only the presence of a mutant designated genetic sequence but also whether that designated genetic sequence is located on both (+/+homozygous), one (+/−heterozygous) or neither (−/− wild type) chromosome(s). The zygosity results are then determined by evaluating both pieces of information. If signal is acquired solely from the mutation probe or the endogenous probe then the samples is homozygous for the mutation or homozygous for the endogenous sequence, respectively. If signal is acquired from both probes, then the sample is heterozygous. The LIMS will establish three distinct categories to correspond with the three control samples needed (a homozygous, a heterozygous and a wild type sample).

To effectively genotype these zygosity samples, additional bioinformatics are needed from the remote user 1. Specifically, the screening laboratory 20 requests that the remote user 1 provide both the base sequence of the designated genetic sequence of the mutation as well as the DNA sequence of the endogenous location. The endogenous DNA sequence is disrupted if a mutation has occurred. Once the precise sequence data is acquired, two probes are designed. The first probe determines if the sequence of the mutation is present, irrespective of the number of times it is present. The second probe determines if the endogenous DNA sequence is present. It is these two probes that the oligonucleotide vendor transmits to the screening laboratory 20.

With respect to human genotyping, a remote user 1 can contact the screening laboratory 20 and provide information for a human mutation or suspected endogenous condition of interest. This information may include the remote user's interest in wanting to know if the sample is from a human or a mouse and if it is from a human what gender is the sample. The screening laboratory 20 can acquire a probe that can distinguish between humans and mice. This is accomplished by identifying areas of genetic sequence in the mouse genome that are not homologous with the genetic sequence in the Homo sapiens genome. With no input from the remote user 1, the screening laboratory 20 can query a database such as ENSEMBL that would discriminate between the sex chromosomes in humans (X and Y). This query would yield sequence data for the Y chromosome, which is the designated genetic sequence. The screening laboratory 20 can take the designated genetic sequence, or portion thereof, and build probe as to be informative for screening. Moreover, where there are a large number of nucleotides that are unique on the human Y chromosome, the screening laboratory 20 may build probes anywhere inside the sequence. The remote user 1's Internet web-based account will have a field populated that represents these reagents with an identifier such as the genetic line/profile identification 84. The remote user 1 will use the identifier (strain name or profile name) to indicate that these specific reagents are to be used on subsequent samples.

Similarly, if the remote user 1 requires SNP genotyping a remote user 1 can contact the screening laboratory 20 and provide a literature reference of the mutation which discloses the mutation name. A mutation name query of the Mouse Genome Informatics website yields links to different databases such as ENSEMBL and National Center for Biotechnology Information that provides sequence data. This sequence data is the designated genetic sequence. Knowing the endogenous nucleotide and the mutant nucleotide, the screening laboratory 20 can take the designated genetic sequence, or portion thereof, and build the probes as to be informative for screening. For example, if the designated genetic sequence is 500 nucleotides in length, the screening laboratory 20 may build a SNP assay targeting the 239th nucleotide. The reagent vendor will then supply to the screening laboratory 20, the probe(s) to specifically discriminate between a nucleotide changes at the 239th position of the designated genetic sequence.

The remote user 1's Internet web-based account will have a field populated that represents these reagents with an identifier such as a name or number, or what is commonly referred to as the genetic line/profile identification 84. The remote user 1 will use the genetic line/profile identification 84 to indicate that these specific reagents are to be used on subsequent samples.

The probes, if they are new and have not before been tested against a sample containing the designated genetic sequence, must then be tested by the screening laboratory 20. To do this, the screening laboratory 20 preferably receives both a positive and a negative strain control samples from the remote user 1 and tests them against the probes to confirm that they can be used successfully to determine whether the designated genetic sequence can be detected. These controls include one positive and one negative control for each mutation found in the strain of interest.

If the designated genetic sequence can be detected using the probes, the screening laboratory 20 updates the website and the order management software to provide the remote user 1 with a web-based selection for sample testing using those tested probes. These selections among which the remote user 1 can select are one of the screening parameter selections identified below.

Alternatively, for example, if the remote user 1 or other third party communicates to the screening laboratory 20 that a particular probe has already been tested and is known to work, or if the screening laboratory 20 has already designed a probe for the designated genetic sequence (which is commonly the case for often-used strains or lines of transgenic animals) the screening laboratory 20 can immediately add a selection to the website and does not need to test controls with the probes.

The strain controls are used to tell LIMS 24 a signal magnitude that is then associated with a positive or negative sample. In one case, the remote user 1 may send these controls together with the samples to be tested to the screening laboratory 20 in a single shipment. Alternatively, the controls may be sent separately from the samples to be tested.

The screening laboratory 20 tests the strain controls using the process described herein for testing samples. At the end of this testing process, the signal values for the strain controls are recorded into LIMS 24. The magnitude of the signal provided by the positive control indicates the expected signal level for subsequently tested samples having the designated genetic sequence. The magnitude of the signal provided by the negative control indicating the expected signal level for subsequently tested samples that do not have the designate genetic sequence.

The computer at the screening laboratory 20 is configured to compare the test results (i.e. signal levels) for every sample that it subsequently tests for that designated genetic sequence with these multiple control signal levels and, based on that determination, to decide whether that sample has or does not have the designated genetic sequence. Positive and negative strain controls for a line therefore do not need to be resubmitted for each subsequent order but can be referenced by the screening laboratory 20 computer when later samples are tested for the same designated genetic sequence.

For transgenic zygosity genotyping, additional controls (not just a positive and a negative) are required to indicate each possible variation such as: a homozygous control, a heterozygous control and a wild type control.

Upon receipt of the probes from a vendor, the sample, if available, will be screened using these reagents. Once a determination is made that there is discrimination between different genetic conditions, then the reagents will be placed in the inventory. Additionally, the screening laboratory 20 will populate a data field on the order management system, allowing the remote user 1 to select the probe or combination(s) for subsequent samples. This data field will be populated with an indicator such as a mutation name, strain name or genetic line/profile identification that will represent these reagents or combination of reagents that will be used in subsequent samples of this strain. This allows the remote user 1 to select the indicator of the reagents and prevents the need to transfer genetic information with each order.

Figure 2:
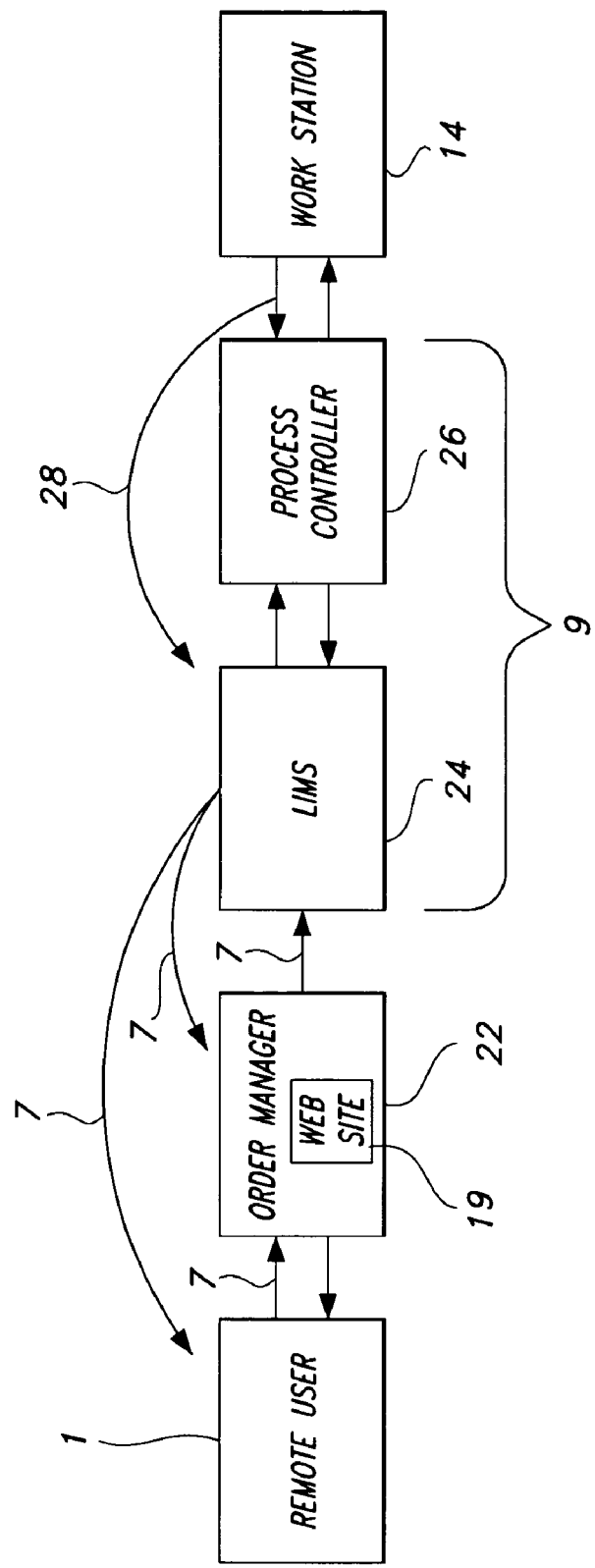
FIG. 2 is a block diagram of one embodiment of the system.
Figure 3:
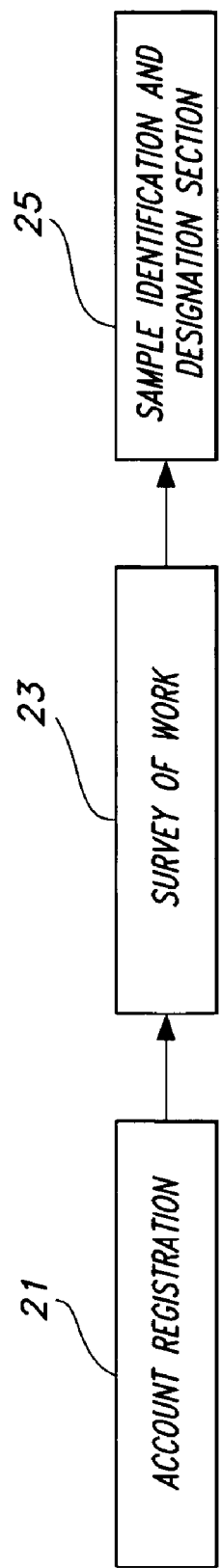
FIG. 3 is a block diagram of the ordering procedure.

FIGS. 1-3 present an overview of certain features of the present invention. The present invention allows a remote user 1 with access to a computer 5 to order genotype screening of samples they submit to screening laboratory 20. Using the Internet or other communication link 7, the remote user 1 sends an access request from the remote user's computer 5 to a screening laboratory 20 computer 9 via an electronic communication link 7, such as the Internet. The screening laboratory 20 website 19 will transmit an access enabling response to the remote user 1 via electronic communication link 7. This response includes three distinct sections. The three sections are Account Registration 21, Survey of Work 23 and Sample Identification and Designation 25 (FIG. 3).

Now referring to FIG. 2, a remote user 1 can access screening laboratory 20 website 19 via communication link 7. The website 19 can be housed by an order manager 22. An order manager is a software-based order management system. In the preferred embodiment the order manager 22 is an order management system developed by BIG FISH, a software development company in Memphis, Tenn. The order manager 22 functions to manage the placement of the order. The order received from the remote user 1 is transmitted to website 19, which reports the order to order manager 22. The order manager 22 is in electronic communication via link 7 with screening laboratory 20 computer 9. Screening laboratory 20 computer 9 includes LIMS 24, which is communicatively coupled to a process controller 26.

LIMS 24 is the generic name for laboratory information management system software. The function of LIMS 24 is to be a repository for data, to control automation of a laboratory, to track samples, to chart work flow, and to provide electronic data capture. LIMS 24 can also, in another embodiment, be in direct communication with the remote user 1 via an electronic communications link 7. Any standard laboratory information management system software can configured to be used to provide these functions. Alternatively, a standard relational database management system such as ORACLE (ORACLE CORP., Redwood Shores, Calif.) or SQL SERVER (MICROSOFT Corp., Redmond, Wash.) either alone or in combination with a standard LIMS system can be used. In the preferred embodiment, the NAUTILUS program (THERMO LABSYSTEMS, a business of THERMO ELECTRON CORPORATION, Beverly, Mass.) is used.

The process controller 26 is communicatively coupled to the workstation 14. The process controller provides commands to any portions of the workstation 14 that are amenable to automation. For example, process controller 26 directs the delivery of the probes to the Screening Station 95. The workstation 14 is communicatively linked 28 to LIMS 24. In this way, the workstation 14 can provide data to LIMS 24 for the formulation of the outcome report 249, and then, via link 7 to the order manager 22 or remote user 1. In an alternative embodiment, remote user 1 at remote user computer 5 can be linked 7 to the screening laboratory 20 by a direct phone line, cable or satellite connection.

Figure 4:
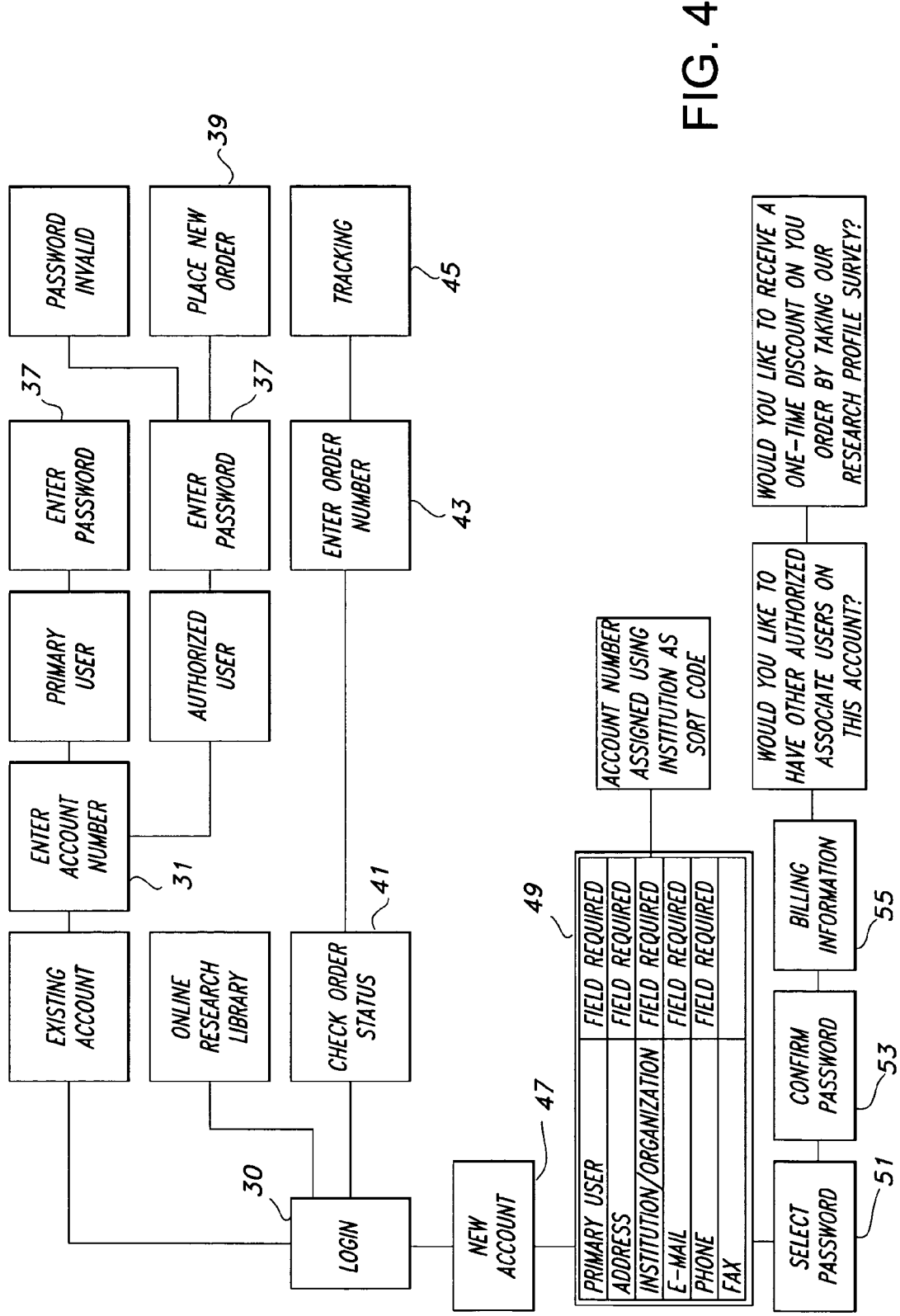
FIG. 4 is a block diagram of account registration.

Now referring to FIG. 4, the user's Account Registration section 21 begins with logging into the system 30. A remote user 1 accesses an existing account by entering an account identification 31, which is, for example, an e-mail address. The remote user 1 will then enter a password 37. If a valid password is entered, the user can place a new order 39. Alternatively, the user can check an order status 41 by providing an order number 43 and can proceed to order tracking 45. Alternatively, a new account 47 can be opened by providing an institution name, principal investigator, address, phone number, fax number, electronic mail address, billing information, and other authorized user names 49. The user can enter a password 51, confirm the password 53 and enter this billing information 55.

Figure 5:
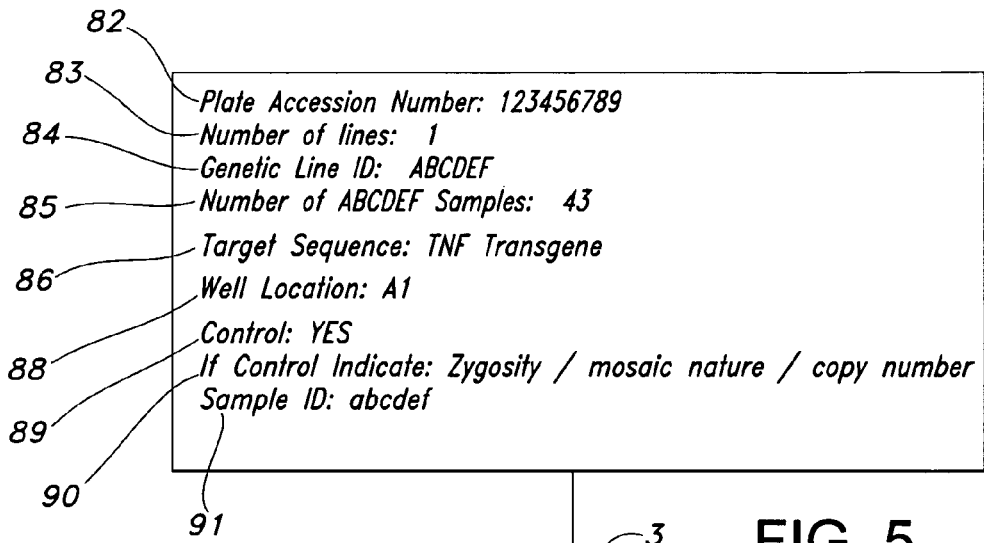
FIGS. 5-6 illustrates the survey of work and sample identification sections.
Figure 6:
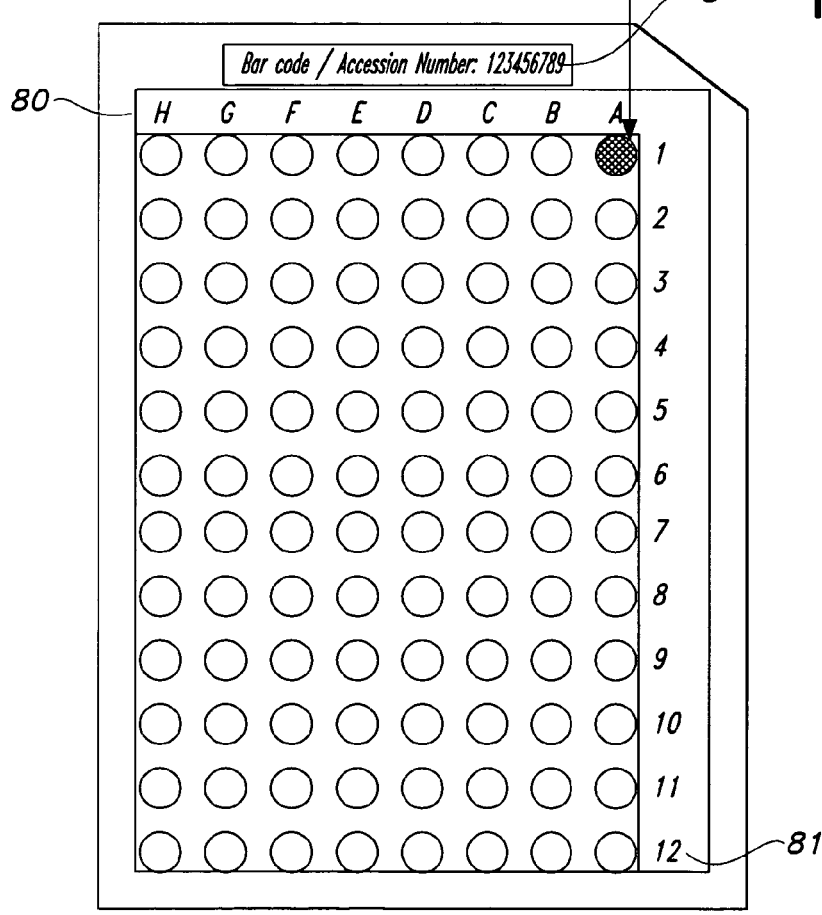

Now referring to FIGS. 5-6, once the remote user 1 submits the Survey of Work section 23 the remote user 1 will be presented with the Sample Identification and Designation section 25. In this section, the user (among other things) identifies where he will place each sample to be tested in an actual (physical) container 2 (FIG. 1) by associating each sample with a corresponding well of a virtual 96 well container displayed on the computer screen of computer 5 as described below. The Sample Identification and Designation section 25 includes 96 well container locations. The remote user 1 designates which sample was or will be placed into each well. If the remote user 1 has more than 96 samples, subsequent 96 source well containers and designations are available. With respect to FIG. 6, a 96 well source well container 2 having a barcode accession number 3 (FIG. 1) will be shown (FIG. 6) oriented in the longitudinal direction having an X axis labeled "A" to "H" (at 80) and a Y axis labeled "1" to "12" (at 81). The X and Y axes designate a well position such as "A1".

FIGS. 5 and 6 together illustrate the Survey of Work section 23 and the Sample Identification and Designation Section 25. Referring now to FIG. 5, the remote user 1 is asked to provide: source well container 2 accession number 82, which the remote user 1 gets from the accession number 3 on the physical source well container 2 at his facility (FIG. 1) that he intends to fill (or has filled) with the samples, number of lines 83, genetic line/profile identification 84, number of samples 85, and well location 88. The remote user 1 is also asked for any internal sample identification number 91.

For genotyping (i.e. screening to determine the presence of a designated genetic sequence) the positive strain control and the negative strain control samples are designated and deposited in wells of a microwell container. The remote user 1 indicates that a sample is a control sample at 89. This assumes, of course, that the strain controls were not earlier provided to the screening laboratory 20 as described above. If a control is deposited in source well container 2, remote user 1 can also designate the zygosity, mosaic nature and copy number of the sample.

At this point, the remote user has completed the Survey of Work section 23 and the Sample Designation section 25 of FIGS. 5-6 and is ready to transmit the screening parameter selections gathered in those sections to website 19 and thence to screening laboratory 20 computer 9.

Now referring to FIGS. 1 and 2, the remote user 1 transmits his or her order including the completed screening parameter selections to the screening laboratory 20 via link 7 such as the Internet or a direct line. The remote user 1 can transmit the selected screening parameter selections to LIMS 24 in screening laboratory 20 via electronic communications link 7. This link 7 can be direct or indirect. In the indirect route, the screening parameters are first transmitted to web site 19, wherein order manager 22 receives the order and then provides LIMS 24 with the screening parameter selections.

In a particularly preferred embodiment of the system described in the foregoing paragraphs, remote user 1 at computer 5 transmits a request for a home web page served by screening laboratory 20 web site 19 via the electronic communication link 7. Web site 19, in turn, serves a home web page to computer 5 that includes information identifying the source of the web page and including a login button. Remote user 1 at computer 5 clicks on the login button displayed on his computer screen, transmitting a signal to web site 19 requesting access to the web site. This request is transmitted over communications link 7 to web site 19, which responds with a second web page having fields for the entry of an account identifier (in the preferred embodiment an e-mail address), and a password. Remote user 1 enters the remote user 1 e-mail address and password, and transmits this information to web site 19 to gain access to the web site. Web site 19 receives this access request and compares the account identifier and password against its database of pre-existing accounts in the order manager 22 to determine whether the user is permitted to access the web site 19. If so, computer order manager 22 serves up a further web page, called an order manager web page, which includes several user selectable choices including an "order status" button for tracking previous orders and results (if any have been received), a "supply request" button for requesting supplies, and an "order" button for ordering additional tests.

To order genetic testing, user 1 clicks on the "order" button displayed on the screen of computer 5. Computer 5 transmits the user 1 request to web site 19. Web site 19 receives this request, and transmits a first ordering web page to computer 5. Computer 5, in turn, displays several fields on its computer screen, including several data entry widgets. The first of these widgets is list box including two selectable entries for requesting the speed of service. In the preferred embodiment there are two speeds of service: 24-hour service and 72 hour service. The second of these widgets is a list box providing several entries, each entry in the box corresponding to a strain for which the sample is to be tested. The third widget is a text box for entering the number of samples of the selected strain to be tested. The fourth widget is a text box for entering the accession number (typically a bar code number) of the source well container 2 in which the samples are to be placed for shipping to the screening laboratory 20.

The remote user 1 types in the number of samples to be tested. In this embodiment the samples are taken from transgenic animals, each sample typically corresponding to one animal to be tested. Typically several animals are tested to determine if they received the transgenic gene from their parents. Each strain of animal is defined by one or more designated genetic sequence. Thus, by designating the strain for which the samples are to be tested, the remote user 1 selects the one or more designated genetic sequences associated with that sequence. In the preferred embodiment, the remote user 1 can also select or deselect each individual probe that is used to screen for the designated sequences in the strain or line of the biological sample.

Once the remote user 1 has entered the number of samples to be tested, he or she then enters the name of the strain that the samples are to be tested for. Again, by selecting a strain the remote user 1 indicates the designated genetic sequence for which the samples are to be tested, since each strain is bred to have that sequence.

Once remote user 1 has selected the speed of service, the strain to be tested, and the number of samples to be tested for that strain, he enters the accession number from the source well container 2 and clicks on a button on the first ordering web page for recording this first group of samples to be tested. Computer 5, in turn, generates a revised first ordering web page, the revised page including a table entry in a table on the revised web page listing the first group of samples in tabular form, wherein each row in the table corresponds to one group of samples to be tested, identifying that group of samples by the strains for which that group of samples is to be tested, and the number of samples in that group.

This process of creating a new group of samples and identifying them by the strain for which they will be tested, and the number of the samples, can be continued as many times as necessary until all the samples to be tested are identified in the table.

Once all of the groups of samples have been entered and listed in the table on the revised first ordering web page, the operator then selects a button identified "next" and moves to the next stage in the ordering process. Computer 5 transmits this request to web site 19, which generates a graphical image of a 96 source well container, appearing on the screen of computer 5 identical to the corresponding 96 source well container 2 that the remote user 1 is filling/has filled with samples, and transmits that image embedded in a second web page back to computer 5 for display. The second web page includes a graphical representation of a 96 well plate, in a top view, showing the two dimensional array of all 96 wells in which the remote user 1 is to place the samples identified previously. Web site 19 calculates the respective positions of each group of samples in the well container 2. Each group is shown in the graphical representation of the well plate in a different color. All the wells in a group are shaded with the color associated with that group.

Samples of the same color from the same group are grouped together thus producing several different contiguous groups of wells, each group of wells have the same color different from the color of the adjacent groups.

The images of the wells in the web page are displayed on the computer with an initial shading to indicate that they have not been identified to a particular animal from which the sample in each well will be taken. In the preferred embodiment, each well contains a sample, such as a tissue sample, taken from an individual animal. The purpose of the testing performed on the samples in the wells is to determine the genetic characteristics of the animal from which each sample was taken. In order to relate the test results performed on each sample back to the animal from which the sample was taken, the user must make a record of the animal source of each sample (i.e. the animal from which each sample was taken).

To uniquely identify each sample in each well with an associated animal, remote user 1 selects a button on the third ordering web page. This button signals computer 9 to generate an additional web page. This web page lists each well in the well plate that was previously identified as containing a sample. Thus, if the first group of samples were 13 in number, there would be 13 entries listed in the additional web page. The web page itself is arranged as a single column of entries. Each entry in the column of entries includes a well identifier (called well location 88, above), which is a string of alphanumeric characters that uniquely identifies one well of source well container 2. A preferred well identifier for the 96 well plate is an alphabetic character followed by a numeric character. A text box is adjacent to each well identifier on the additional web page. To uniquely identify each sample in the source well container 2, the user enters alphanumeric characters in the text box that are uniquely associated with each sample. This identifier is typically a short string of consecutive alphabet or numeric characters, a practice commonly used by research facilities to identify individual animals used for testing.

Animals in a particular group of animals having (presumed) common genetic characteristics will typically be identified by tattoos, tags, or other permanent means by consecutive or sequential numbers, characters, or combinations of numbers and characters (for example "A1", "A2", "A3", or "101", "102", 103", or "AA", AB", "AC", etc.). In a preferred embodiment, user 1 enters each animal number into the text box as a sample ID 91. Animals may also be identified by a unique combination of disfigurements such as cutting or cropping toes, tails or ears that can also be approximated to a progressive alphanumeric sequence.

To assist the remote user 1 in entering the sample ID 91 into each of the text boxes in the additional web page, a button is provided to automatically fill several consecutive text boxes based upon the alphanumeric characters typed into a few text boxes from the group. For example, if the user types in "B7" in the first text box of a group, then types in "B8" in the second text box of a group, computer 5 is configured to automatically generate consecutive alphanumeric strings to fill the remaining text boxes of the group based upon these two manually typed-in entries. In this case, computer 5 would automatically generate the alphanumeric strings "B9", "B10", "B11", etc. and insert these characters sequentially into the remaining text boxes of the group in the additional web page. This process can be repeated for each subsequent group shown on the additional web page. Alternatively, the computer can be configured to automatically generate alphanumeric characters for all the groups at once and to fill the text boxes of all the groups all at once. Once the user has finished identifying all of the groups of samples and filling out all of the sample ID's 91 in the text boxes on the screen of computer 5, he clicks on a button labeled "next". Computer 5 transmits this request to website 19, which responsively generates another web page in which the user 1 enters shipping and tracking information. This page, called the order confirmation page, includes a text box for entering a character string. This character string provides access to a web-based shipment tracking system of a commercial shipping company. In the preferred embodiment, the character string is a tracking number used by the shipping company to track the samples from the remote user 1 to the screening laboratory 20. In the preferred embodiment, the tracking number is provided to the user together with the source well container 2 and the packaging materials in which the user places the source well container 2 for shipment to the screening laboratory 20.

The order confirmation page also includes an invoice that lists the different tests requested by the operator in the foregoing steps on the screen of computer 5. Each test or group of tests is displayed on the screen adjacent to the price or prices for those tests. A total price of all the tests is displayed as well.

The order confirmation page has a second text box in which the remote user 1 can type the expected shipping date. The expected shipping date is the date on which remote user 1 intends to give the samples in their packaging materials to the delivery service associated with the tracking number. By providing the anticipated shipping date to the website 19 and then to the screening laboratory 20, personnel at the screening laboratory 20 can anticipate the arrival of each shipment and prepare for its arrival by pre-ordering reagents, probes required for testing the samples in advance.

Once the operator has entered the tracking number and the expected shipping date, he clicks on a button labeled "confirm order", which transmits the completed order, including the tracking number and expected shipping date to website 19 and order manager 22, and thence to LIMS 24.

In the preferred embodiment, once the order has been transmitted to the order manager 22, the order generates two electronic messages, which will be sent to different locations. The first message is cross-referenced in LIMS 24 with a list of stocked probes. If the probe designated by the user is not stocked, an order message is sent to a supplier 11, such as a contracted probe provider. This request can be transmitted from remote user 1 to screening laboratory 20 via any form of electronic communication, and then via a form of electronic communication 10 to suppliers' computer 8, or in the alternative, the order message can go from user 1 via any form of electronic communication link 12 to suppliers' computer 8. The supplier 11 creates the probe based on the designated genetic sequence designated by the remote user 1 or the screening laboratory 20. The made to order probe can be referred to as the target-binding probe. This supplier 11 will then barcode and overnight ship if possible 13 the target-binding probes 17 to the screening laboratory 20. Once the target-binding probes for each order for that day's screening are received by screening laboratory 20, the barcodes on the target-binding probes are scanned into LIMS 24. The LIMS 24 records the date and time the target-binding probes were received along with the quality control data provided from the probe provider.

In the preferred embodiment, the target-binding probes are placed in workstation 14 and LIMS 24 will record the barcode of the probe and record its specific location on the deck of the workstation 14, as will be discussed in more detail with respect to the Screening Station 95. Additionally, the screening laboratory 20 and the LIMS 24 system correlates which target-binding probes will be used on which samples, as will be discussed in more detail with regard to the Screening Station 95.

The second message, in the preferred embodiment, that is generated from the order placement of the remote user 1 insures that the remote user 1 has the proper supplies to package and ship their samples. This message, sent via link 12, will define the barcode number of well container(s), shipping labels tracking number and amount of reagents needed for the user. In response to this message, supplier 11 will package 18 supplies for remote user 1 and ship 14A the supplies back to remote user 1.

Once the remote user 1 procures or receives these supplies, the remote user 1 places the appropriate samples into the source well containers 2 previously identified in the order sent to website 19, order manager 22 and LIMS 24. In other words, the remote user 1 fills each well of source well container 2 such that each well contains the same sample with the same sample ID 91 that the user previously identified in the order previously sent to website 19. Alternatively, if the user already had sufficient supplies when the user placed the order the user need not wait for a source well container 2 to be sent by a supplier, but can fill the source well container 2 when the user creates the order, or even before the order is created. What is important is that the contents of the actual 96 source well container 2 that the user fills exactly matches the description of the samples and has the same accession number as the order the user previously sent to website 19.

The samples can be obtained from prokaryotic or eukaryotic organisms. The samples may be a tissue sample from a mouse 8A, but can also come from other animals (including humans), plants and viruses. In the preferred embodiment, mouse tails or ears are snipped to provide a tissue sample. Source well container 2 is a 96 well plate or the like that receives the sample in each well of the well plate. A sufficient amount of lysis reagent can be added to cover the sample. In one embodiment, the lysis reagent is added prior to transit to the screening laboratory 20. Although, in the preferred embodiment the lysis reagent is added at the screening laboratory 20 at Lysing Station 92.

Referring now to FIG. 1, source well container 2 has an accession number 3 affixed to the side of the container. The accession number is used by LIMS 24 to track the source of source well container 2. The remote user 1 places the appropriate samples into the well locations in source well container 2 that they had previously designated while placing their order in FIG. 6. Once the samples are in the proper wells in the source well container 2 then the remote user 1 in one embodiment dispenses a predetermined amount of reconstituted lysis reagent 4 to cover the sample into each well using a pipette. The lysis reagent 4 is formulated to lyse the tissue to obtain cellular debris including genomic nucleic acid. A lysis reagent 4 can be formulated to lyse the biological sample while in transit between remote user 1 and the screening laboratory 20. The transit time is approximately 24 hours as all samples are shipped via an express delivery service, such as FEDEX (Memphis, Tenn.). The remote user 1 will add lysis reagent 4 to each well of the source well container 2. The lysis reagent 4 should completely cover the samples. Once the samples and lysis reagent 4 are in the source well container 2 the remote user 1 places a seal on the top of the source well container 2 preventing samples from leaking. The remote user 1 then places a plastic lid on the seal for transportation. The remote user 1 then places the source well container 2 into an overnight delivery service package 15. The remote user 1 will then seal the package and ship 16 to screening laboratory 20, and apply a barcode shipping label.

A biological sample can be collected in a variety of ways to facilitate rapid screening. In one aspect of the invention, the biological sample is a sample of tissue such as from a mouse biopsy. The sample of tissue can include a portion of a tail, toes and ears. The tissue sample is collected by a remote user 1 and placed in a well of a source well container 2. The microwell container is transported to the screening laboratory 20. A multi-well container as shown in FIG. 1, in the preferred embodiment, is a 96 microwell source well container 2 but can include other multi-well containers, such as Strip Racks, 24 well plates, 384 well plates and tube rack holders or the like. As described above with regard to FIG. 6, the remote user 1 operates computer 5 to enter a variety of data regarding the samples placed in the source well container. Once all of the samples in all of the wells have been identified in this manner, the remote user sends the source well container 2 containing a plurality of biological samples to a screening laboratory 20 for screening.

In another embodiment of this invention, the biological sample is a blood sample collected by nicking the animal to be tested and blotting the blood on a filter paper. The blotted filter paper is placed in individual wells of source well container 2 by the remote user 1 and transported to the screening laboratory 20. In both of these embodiments, the biological sample is disposed on an adsorbent carrier.

In another embodiment, the biological sample is embryonic tissue or embryonic stem cells. A sample of embryonic tissue is placed or grown in a well of a source well container 2 by the remote user 1 and transmitted to the screening laboratory 20.

Figure 7A:
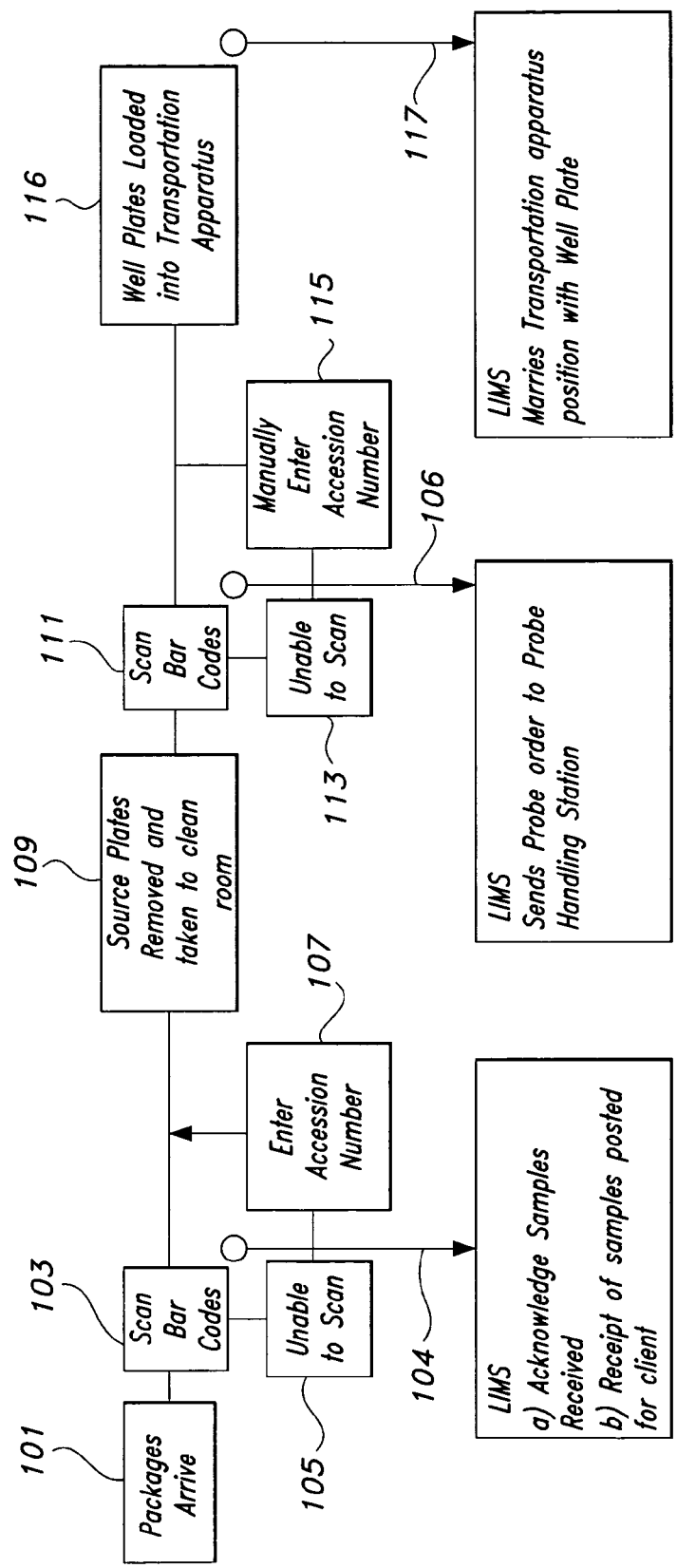
FIG. 7A is a block diagram of the laboratory process system.
Figure 7B:
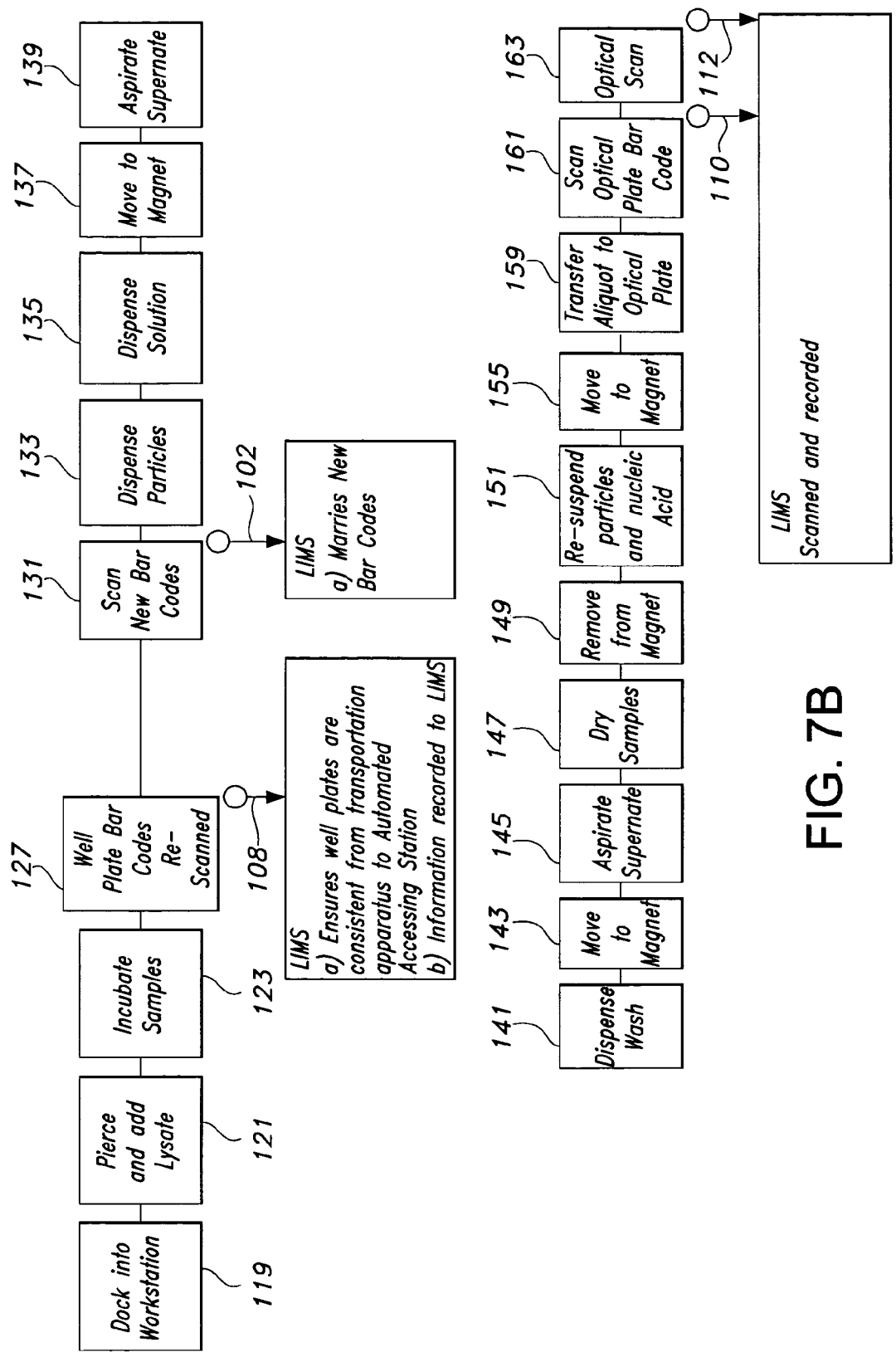
FIG. 7B is a block diagram of the laboratory process system.

Now referring to FIG. 7A-D, the preferred embodiment of the present invention is shown. In FIG. 7A, the source well containers 2 arrive 101 at the screening laboratory 20. The tracking number of the shipping label is read with a barcode reader 103. If the shipping label is unreadable 105, the tracking numbers are manually entered 107. The scanning of the tracking number is received 104 in LIMS 24 and a received message is posted to the user's account as shown in tracking field. The source well container 2 are removed from the package and taken to a clean room 109. The source well containers 2 contain the raw biological matter and in one embodiment lysis reagent. The source well containers 2 individual barcodes are scanned by the barcode reader 111 and recorded 106 in LIMS 24 as accession numbers. LIMS 24 can send 106 a probe order to supplier 11 through the order manager 22. If the source well containers 2 individual barcodes are unable to be scanned 113, the accession numbers are entered manually 115. If the tracking number, accession number, user order and worklist properly correlate, LIMS 24 will activate (not shown) an active record number for the containers.

The source well containers 2 are loaded 116 into a transportation apparatus in a clean room. A transportation apparatus is any device that holds well containers and that can dock with the workstation. The transportation apparatus, in the preferred embodiment, includes several rigid trays stacked vertically in a housing unit that is mobile. This transportation apparatus can be moved between different automated stations, docked and the rigid trays can be removed in an automated fashion and processed on the deck of a workstation. Each rigid tray consists of nine locations for source well containers 2. Each of these nine locations per tray has a unique barcode designating its specific location inside the trays of the transportation module.

Source well container 2 accession number 3 is scanned with a barcode reader and the bar-coded source well container 2 location in the transportation apparatus trays is scanned. The barcodes of source well containers 2 are married 117 in LIMS 24 with the unique barcode locations in the transportation apparatus trays for tracking purposes. LIMS 24 records and associates each well container to this location. Once the transportation apparatus is loaded with the source well containers 2, the transportation apparatus is docked 119 into the laboratory workstation 14.

LIMS 24 will generate a worksheet for laboratory personnel (not shown). The worksheet outlines the probes that the operator will need to prepare or gather in order to test the latest samples. The LIMS 24 worklist will generate a single file. The file format may include, but is not limited to, ASCII, XML or HTML. The file will be written into a specified directory on the network drive. The name of the file will be unique and will correlate to a run number. The extension will be unique for worklist files.

In the configuration described above, a transportation apparatus includes a housing unit provided to support several trays, each tray having nine different locations for nine source well containers 2. In an alternative embodiment, however, the housing unit can be eliminated. Instead, the source well containers 2 can be manually transported throughout the workstation in trays from functional station to functional station. In this system, operator at the laboratory loads source well containers into the trays after the source well containers 2 are received at the screening laboratory 20 and are scanned into LIMS 24 as described above for transportation to workstation 14. Alternatively, source well containers 2 can be transported individually to workstation 14 and be placed in a tray or trays that are already located at workstation 14.

Figure 8:
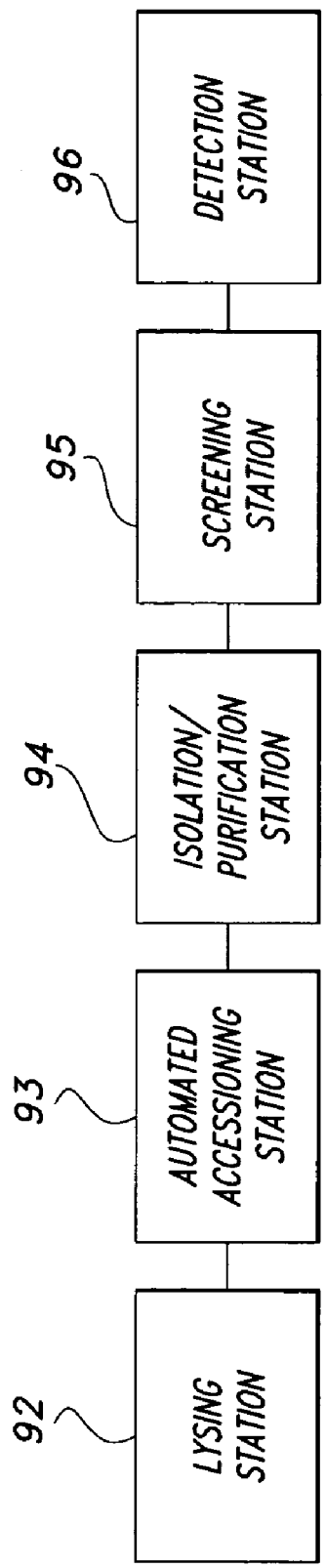
FIG. 8 is a block diagram of standard laboratory stations.

We now refer to FIG. 8, which depicts one embodiment of the workstation 14. Standard laboratory stations are logical groupings of laboratory operations. These groupings, however, do not necessarily refer to different physical stations. These logical groupings include: Lysing Station 92, Automated Accessioning Station 93, Isolation/Purification Station 94, Screening Station 95 and Detection Station 96, all of whom comprise workstation 14. Lysing Station 92 is an alternative step provided to lyse the samples in containers 2 in the event remote user 1 does not choose to lyse the samples by adding a lysis reagent before sending them to laboratory 20. The functions of the various logical stations are described below in connection with the steps shown in FIGS. 7A-D. The following description provides the preferred embodiment, although one skilled in the art could elect to conduct these methods with varying degrees of automation as required.

As mentioned above, remote user 1 need not add a lysis reagent to the samples before shipping them to screening laboratory 20. Instead, the samples may be shipped un-lysed (at room temperature) and may be lysed at laboratory 20 by piercing the cover 121 of the container 2 and treating each of the samples with a lysis reagent after docking the tray in the workstation 119 in the lysing station 92. The samples are incubated 123 to produce a lysate containing cellular debris including at least a portion of intact genomic nucleic acid.

For tissue biopsies, the lysis process in the preferred embodiment includes incubation with the lysis reagent, such as proteinase K and a Nuclei Lysing Solution (NLS) (PROMEGA Corporation, Madison, Wis.) at 55° C. for three hours. Other lysis reagents such as sodium dodecylsulfate and proteinase K can be used. The lysis reagent is selected to not fragment the genomic nucleic acid. A sufficient amount is an amount in the wells of container 2 sufficient to cover the samples.

With respect to the blood sample collection method, a sufficient amount of a lysis reagent, such as Nuclei Lysing Solution (PROMEGA Corporation, Madison, Wis.) is added to each well of source well containers 2 to cover the filter paper. With respect to animal embryonic tissue and embryonic stem cell screening, Nuclei Lysing Solution (PROMEGA Corporation, Madison, Wis.) is added to each well containing the tissue/cells. The source well container 2 is treated under conditions to facilitate rapid lysis of the biological sample. In the preferred embodiment, these conditions are heating at 55° C. for three hours. Additionally, if the samples are embryonic tissue, in the preferred embodiment they are sonicated for 3-5 seconds after lysis. However, embryonic samples should not be sonicated for such a period of time to eliminate all intact genomic nucleic acid.

Figure 10:
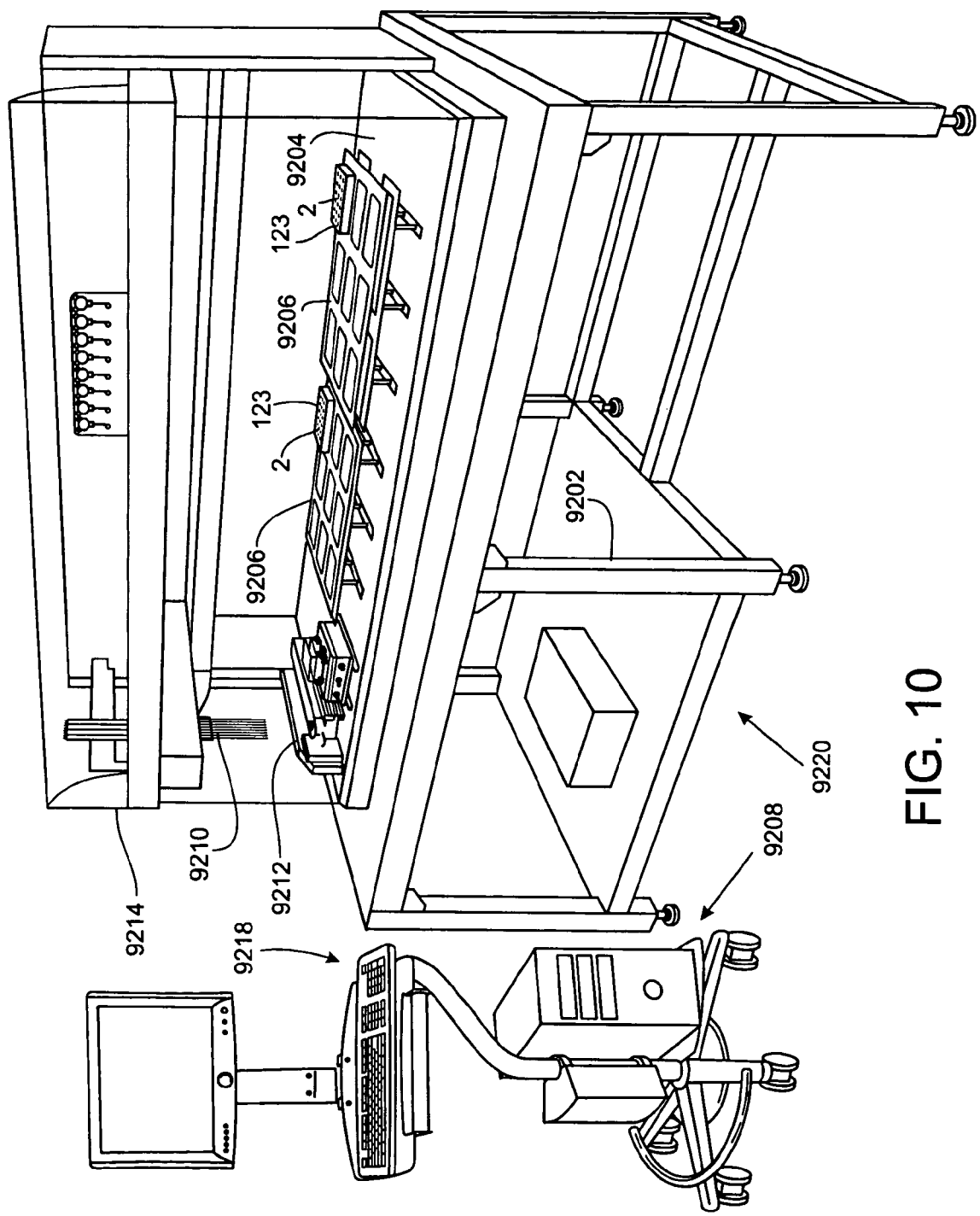
FIGS. 10 and 11 illustrate a preferred device for performing the functions of a Lysing Station and an Automated Accessioning Station as described herein, including an oven (FIG. 11) for incubating the samples.

The preferred method of performing the above lysing steps at Lysing Station 92 includes loading source well containers 2 into the tray 9206 and taking the rigid tray to Lysing Station 92 to be lysed. Lysing Station 92 includes a liquid handler 9220, such as GENESIS TECAN (Raleigh Durham, N.C.) or MULTIMEK BECKMAN (Indianapolis, Ind.). An example of a preferred Lysing Station 92 is shown in FIG. 10. It includes a frame 9202, on which a deck 9204 is mounted to provide a horizontal working surface, which supports tray 9206, which supports and positions up to nine source well containers 2. A material handler 9214 is fixed to frame 9202 and extends upward and across the top surface of deck 9204. A computer 9208 is coupled to material handler 9206 to direct the movement and operation of pipettes 9210. A trough or reservoir 9212 is provided on deck 9204, from which computer 9208 commands the material handler 9214 to aspirate lysis reagent into pipettes 9210 and to deposit the reagent into wells of container 2.

The operator first carries a plurality of source well containers 2 and places them on deck 9204 in one of the nine positions on the rigid tray 9206 that support and orient source well containers 2 thereby docking them 119 into the workstation 14. The operator then enters the number of wells that are filled with samples in each of the source well containers 2 into computer 9208 in combination with the location of that container with respect to tray 9206.

Knowing the location of each source well container 2 in tray 9206, and the number of wells that are filled with samples in each of these source well containers 2, computer 9208 then directs material handler 9214 to move the pipettes 9210 to each source well container 2 in turn, piercing 121 the barrier sealing mechanism and filling each of the wells of source well containers 2 containing a sample with lysis reagent. By providing the location and the number of samples, computer 9208 is configured to fill only the wells containing samples with lysis reagent and to leave the empty wells empty of lysis reagent.

Figure 11:
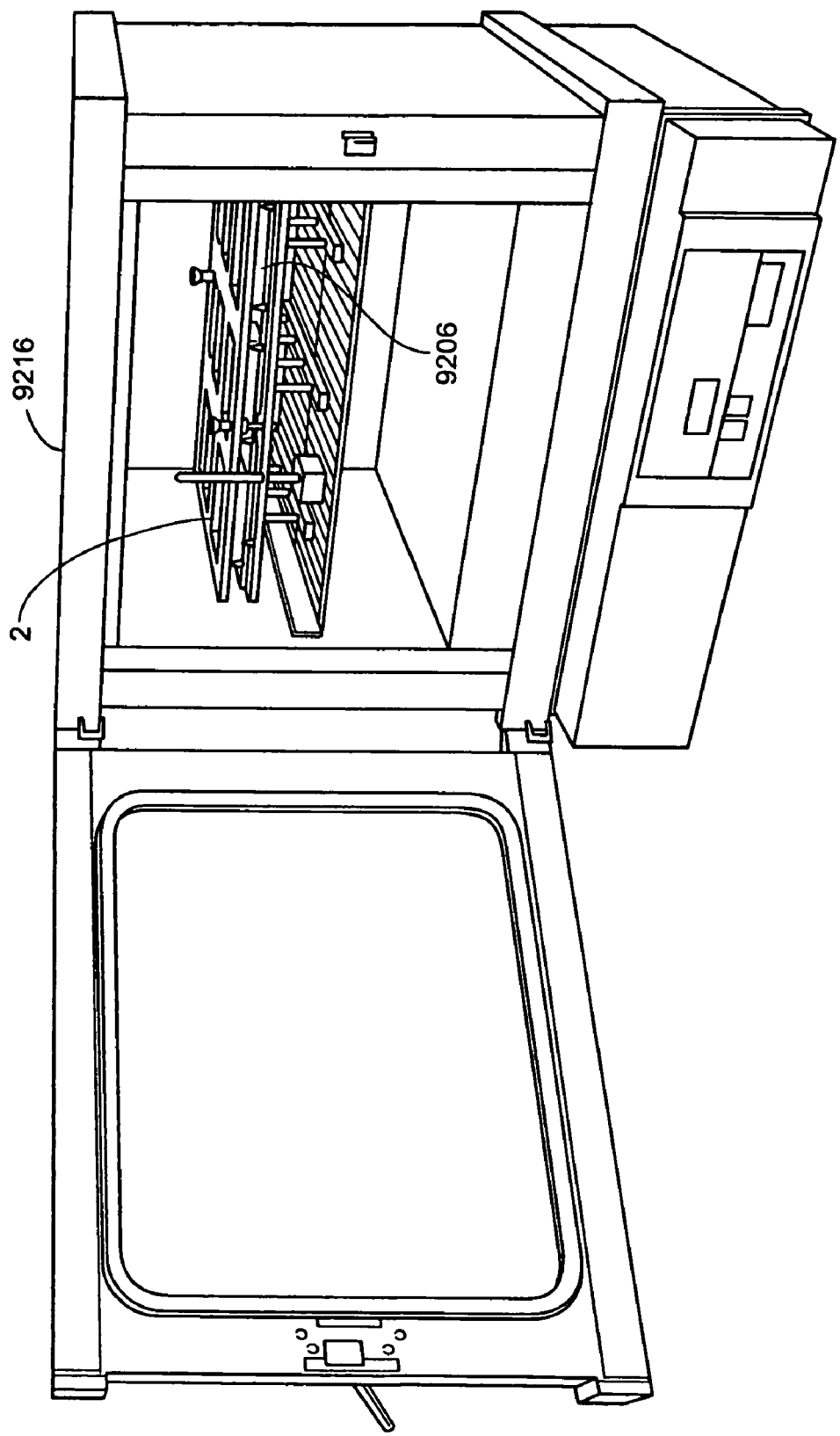

Once each of the sample-containing wells has been filled with lysis reagent, the operator moves the entire tray or trays 9206 containing the samples to an oven 9216 (FIG. 11), where the samples are incubated 123 by heating for a period of about three hours at a temperature of 55° C. (described above). Once the incubation process is complete, the operator moves source well containers 2 supported on the tray or trays 9206 to Automated Accessioning Station 93.

An Automated Accessioning Station 93 provides a device to remove liquid from the source well container 2 to the primary master well container 6. The primary master well container 6 is the container in which the nucleic acid is isolated. It is preferably a 384 well plate (FISHER SCIENTIFIC #NC9134044). Any commercially available automated accessioning device can perform this function such as GENESIS TECAN (Raleigh-Durham, N.C.) or MULTIMEK BECKMAN (Indianapolis, Ind.). These devices are referred to as liquid handlers. The source well containers 2 barcode accession numbers 3 are re-scanned 127. This measurement will be recorded and posted 108 into the LIMS 24 database and reflected in the outcome report 249. Additionally, LIMS 24 ensures 108 that source well containers 2 are consistent from transportation apparatus to the Automated Accessioning Station 93. Error codes will be generated if a sufficient amount of raw testing material is not available. The liquid handler utilizes stainless steel, or the like, pipette tips that are washed between each sample transfer. Alternatively, disposable pipette tips may be used.

The nucleic acid lysate is transferred 129 to clean well containers, called primary master well containers 6. Each of the containers 6 has a scannable accession number, preferably a barcode accession number, called "barcodes" or "accession numbers" below. The barcodes of the primary master well containers 6 are scanned 131 and LIMS 24 marries 102 the barcodes for the primary master well containers 6 to the scanned barcode accession numbers 3 of the source well plates 2. The automated process accessioning continues until all of the day's pending samples are accessioned into the primary master well containers 6. The preferred method of performing the above steps at Accessioning Station 93 includes taking the rigid tray 9206 and the source well containers 2 from the incubating oven 9216 back to the same liquid handler 9220 that performs the functions of Lysing Station 92. This liquid handler 9220 is also preferably configured to function as Accessioning Station 93.

Figure 12:
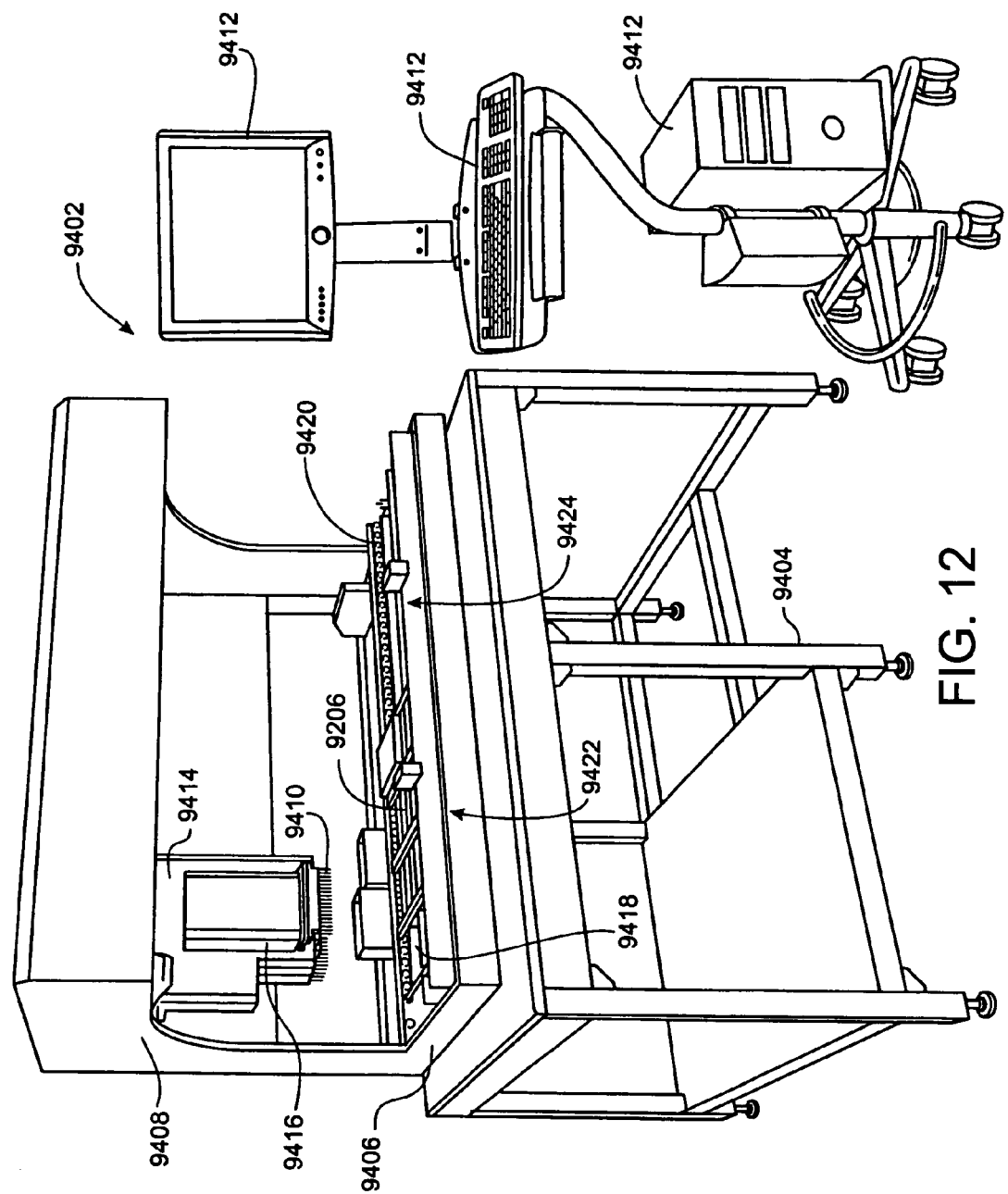
FIG. 12 illustrates a preferred device for performing the functions of an Isolation/Purification Station as described herein.

Referring now to FIG. 12, the operator returns tray 9206 to liquid handler 9220 and places tray 9206 back on deck 9204 generally in the same location it was in when the lysis reagent was inserted into each well containing a sample.

Once in that location, the operator commands computer 9208 to fetch the work list from LIMS 24 and electronically stores it in the computer memory of process controller 26. The work list includes the accession numbers of each source well container 2 that is in tray 9206, together with the probe type that should be used for each well. The work list uniquely associates the location of the well, the accession number of source well container 2 from which the well is from, the probe type that is to be used with the sample in that source well container 2, and the quantity of probe to be added to that sample.

Once computer 9208 fetches the work list, computer 9208 directs the operator to electronically scan 127 the accession numbers of all the source well containers 2 that are in rigid tray 9206 on deck 9204 of liquid handler 9220 using scanning device 9218 coupled to computer 9208. Scanning device 9218 is preferably a glyph scanner, character scanner, bar code scanner, dot matrix scanner, or RFID tag scanner, depending upon the form of the accession identifier (typically a barcode accession number 3) on source well container 2. Once source well containers 2 have been scanned 127, computer 9208 transmits 108 the accession numbers 3 to process controller 26 and thence to LIMS 24. Process controller 26 preferably includes an instrument database to which each of the computers of Lysing Station 92, Automated Accessioning Station 93, Isolation/Purification Station 94, Screening Station 95 and Detection Station 96 transmit their data in order to maintain an ongoing record of the testing process and the location of materials and samples throughout that process. The database is preferably implemented using Microsoft's SQL Server, although any relational database (e.g. Oracle), may be used.

Computer 9208 then commands material handler 9206 to transfer 129 the contents of each well (i.e. lysate) in source well containers 2 to a corresponding well in the primary master well container 6 using pipettes 9210. Computer 9208 directs the operator to scan 131 the accession numbers on the primary master well container 6. Like the accession number on source well containers 2, the accession number on the primary master well container 6 may be any electronically scannable indicia or device. Computer 9208 transmits the accession numbers to process controller 26, which sends them to LIMS 24. In this manner, LIMS 24 maintains a record of each sample and its location in each source well container 2 and in each primary master well container 6. LIMS 24 and process controller 26 correlate the accession number of each primary master well container 6 with the identity of each sample it contains, the strain for which each sample is to be tested, the designated genetic sequence or sequences that identify or indicate that strain, the probes necessary to test for those designated genetic sequences and the results of the testing.

The tray of primary master well containers is moved by the transportation apparatus to the Isolation/Purification Station 94. In this station, the genomic nucleic acid will be isolated and purified using a separation method such as magnetic or paramagnetic particles. Purified genomic nucleic acid, substantially free of protein or chemical contamination is obtained by adding a sufficient amount of magnetic particles to each of the well containers that bind to a predefined quantity of nucleic acid. The term "magnetic" in the present specification means both magnetic and paramagnetic. The magnetic particles can range from 0.1 micron in mean diameter to 100 microns in mean diameter. The magnetic particles can be functionalized as shown by Hawkins, U.S. Pat. No. 5,705,628 at col. 3 (hereinafter '628 patent hereby incorporated by reference). The assay for a nucleic acid sequence uses, in the preferred embodiment, magnetically responsive magnetic particles having a coating of glass microfibers attached thereto.

More specifically, a biological sample including genomic nucleic acid is mixed with a plurality of magnetically responsive magnetic particles having a coating of glass microfibers attached thereto. This lysate contains the constituents of the lysis reagent including surfactant and protein (Proteinase K) as well as the biological constituents including proteins, cellular debris and nucleic acids. In the preferred embodiment, PROMEGA (Madison, Wis.) magnetic particles are used. The magnetic particles and the process to make these magnetic particles are described in Smith et al. U.S. Pat. No. 6,027,945 and Padhye U.S. Pat. No. 5,808,041. These reactants are mixed under conditions to facilitate the binding of genomic nucleic acids to the glass microfibers. The conditions which facilitate binding of the genomic nucleic acids include a binding buffer. The preferred binding buffers are chaotropic salts, such as guanidinium isothiocyanate or a quaternary ammonium salt such as tetramethylammonium chloride or tetraethylammonium chloride.

The unbound portion of the biological sample is removed, preferably by using separation techniques involving magnetically responsive magnetic particles. See e.g. Hawkins (U.S. Pat. No. 5,898,071 col. 3; hereby specifically incorporated by reference). In one embodiment of the invention, a designated nucleic acid sequence, such as a transgenic insert or a selectable marker is detected from a sample of genomic DNA. To detect a nucleic acid sequence, a labeled nucleic acid probe capable of hybridizing to a portion of the bound genomic DNA is mixing with biological sample. In one embodiment, the nucleic acid probe is ligated to a labeled dendrimer. A dendrimer is a nucleic acid structure that is a polymer (either linear of spherical) that is capable of being labeled with fluorescent molecules while at the same time having a plurality of single stranded nucleic acid segments capable of hybridizing to a designated portion of the genomic nucleic acid under hybridization conditions. In the preferred embodiment the hybridization solution is 3.0M Tetramethylammonium Chloride (TMACL), 50 mM Tris, 4 mM EDTA and 0.01% TWEEN 20 polyoxyethylene sorbitan monolaurate. The TMACL is a unique hybridization solution in that it stabilizes the hydrogen bonding between nucleotides. TMACL makes is possible to practically determine melting temperature and subsequently hybridization temperature based on nucleotide length and eliminates the need to account for GC content. Additionally, this hybridization solution is unique in that it keeps the genomic nucleic acid reversibility bound to the magnetic particle during hybridization.

The magnetic particle is washed to remove unhybridized labeled nucleic acid probe and the amount of labeled nucleic acid probe is detected. In an alternative embodiment, the supernate containing a duplex of genomic DNA and hybridized labeled nucleic acid probe is detected.

In the preferred embodiment, the magnetic particles are purchased from PROMEGA Corporation, a measured amount of magnetically responsive magnetic particles are added 133 to the lysate mixture with or without the presence of a chaotropic salt 135. In the preferred embodiment, 30 µl amounts of 1 micron silica magnetic particles with chaotrope 180 µl (PROMEGA Corporation, Madison, Wis.) are added to each well of the microwell container. The fixed volume of magnetic particles becomes saturated with nucleic acid and excess nucleic acid is removed. It has been observed that the resulting nucleic acid concentration between samples is very consistent. In a 100 µl pathlength read by the GENIOS (TECAN, Research Triangle Park, N.C.) a standard A260 is 0.4 OD units. A standard concentration range of 0.1 to 1.0 O.D. units is disassociated from the magnetic particles to yield purified genomic nucleic acid.

Table 1 shows that with increasing amounts of magnetic particles, the nucleic acid concentration also increases.

TABLE 1

| Average | Stdev | Bead Volume per 150 µl of lysate |
|---------|-------|----------------------------------|
| 0.7974  | 0.0072 | 27 |
| 0.8750  | 0.040  | 35 |
| 1.2328  | 0.026  | 50 |
| 1.7900  | 0.022  | 75 |

While the nucleic acid concentration is consistent between samples treated with the same protocol, several factors may increase or decrease the resulting standard concentration of genomic nucleic acid. These factors include: the binding reagent, the number of purification washes, and the solution that is used to elute the nucleic acid. The preferred binding solution for the magnetic particles obtained from PROMEGA (Madison, Wis.) is a chaotropic salt, such as guadinium isothiocyanate. Alternatively, other binding reagents, such as 20% polyethylene glycol (PEG) 8000, 0.02% sodium azide and 2.5 M sodium chloride may be used to nonspecifically bind the genomic nucleic acid to the surface chemistry of the functionalized magnetic particles. If functionalized magnetic particles are used, the preferred binding solution is PEG. The PEG or chaotropic guadinium isothiocyanate allows for the disruption of hydrogen binding of water, which causes binding of the nucleic acid to the magnetic particles. The preferred washing procedure to remove contaminants includes zero chaotrope washes, after the initial chaotrope binding step, followed by three 95% ethanol washes. Aqueous solutions, or the like, are the best elution solutions. These solutions include water, saline sodium citrate (SSC) and Tris Borate EDTA (ie. 1×TBE).

The preferred device for performing the above functions of the Isolation/Purification Station 94 is a liquid handler 9402 identical in general construction to the liquid handler 9220 identified above for use as the Lysing Station 92 and the Accessioning Station 93 that has been configured to automatically transfer the various reagents and other liquids as well as the magnetic particles in the manner described below.

FIG. 12 illustrates a preferred embodiment of the liquid handler 9402. Handler 9402 comprises a frame 9404 on which is mounted a deck 9406, which is surmounted by material handler 9408, which supports and positions pipettes 9410 and is coupled to and controlled by computer 9412, which is in turn coupled to process controller 26 to communicate information to and from LIMS 24. Liquid handler 9402 includes a syringe pump 9414 that is coupled to and driven by computer 9412 to dispense magnetic particles via a 16×24 array of 384 pipettes 9410 simultaneously into all 384 wells of the primary master well container 6 under the command of computer 9412. Liquid handler 9402 also includes a second syringe pump 9416 that is configured to dispense a binding buffer into wells of the primary master well container 6 under computer control. The liquid handler also includes a magnet 9418 mounted in deck 9406 as well as a conveyor 9420 that is coupled to and controlled by computer 9412 to move the primary master well container 6 in tray 9206 back and forth between a first position 9422 in which the container is within the magnetic field and a second position 9424 in which the container is outside the magnetic field.

Before the functions of the Isolation and Purification Station 94 can be performed, the operator must first move the primary master well container 6 from Accessioning Station 93 to deck 9406 of liquid handler 9402 and place it in a predetermined location on the deck. Once the operator has placed the primary master well container 6, the operator starts an isolation/purification program running on computer 9412. This program drives the operations of liquid handler 9402 causing it to dispense magnetic particles 133 into all the wells of the primary master well container 6 containing lysed samples. Computer 9412 signals syringe pump 9414 to dispense the magnetic particles using pipettes 9410 into the primary master well container 6 when container 6 is in position 9424, away from the magnetic field created by magnet 9418.

Once the magnetic particles have been added, computer 9412 then directs the pipettes 9410 to add a chaotropic salt, such as guadinium isothiocyanate to each of the wells to bind the genomic nucleic acid to the magnetic particles at 135. Once the chaotropic salt has been added, computer 9412 then mixes the contents of the wells by signaling the pipettes 9410 to alternately aspirate and redispense the material in each of the wells. This aspiration/redispensing process is preferably repeated three or four times to mix the contents in each well.

Once the contents of the wells have been mixed, computer 9412 pauses for two minutes to permit the magnetic particles, binding reagent, and raw biological material in the wells to incubate at room temperature in position 9424. When the two minutes have passed, computer 9412 commands the conveyor 9420 to move tray 9206 from position 9424 to position 9422, directly above magnet 9418 at 137. In this position the magnet draws the magnetic particles in each of the wells downward to the bottom of the wells of the primary master well container 6. Computer 9412 keeps tray 9206 and the primary master well container 6 over the magnet and within the magnetic field for 2-6 minutes, or until substantially all the magnetic particles are drawn to the bottom of each well and form a small pellet.

The magnetic particles drawn to the bottom of each well have genomic nucleic acid attached to their outer surface—genomic nucleic acid that the magnetic particles hold until an elution solution is placed in each well to release the genomic nucleic acid from the magnetic particles. With the magnetic particles at the bottom of each well and the wells located within the magnetic field, computer 9412 directs the pipettes to aspirate the supernatant 139.

Once the supernatant is removed, computer 9412 signals the conveyor to move the primary master well container 6 on tray 9206 to the nonmagnetic position 9424. The foregoing process of adding chaotropic salt, mixing the combination, pausing, drawing the magnetic particles down and aspirating the supernatant.

Computer 9412 then directs the pipettes to introduce a wash solution (for example 70% ethanol when functionalized magnetic particles are used, or 95% ethanol (3×) when silica beads are used) to resuspend the magnetic particles 141. Computer 9412 again mixes the contents of the wells by signaling the pipettes to alternately aspirate and redispense the material in each of the wells. With the wash buffer and magnetic particles thoroughly mixed, computer 9412 again moves tray 9206 and the primary master well container 6 back over magnet 9420 in position 9422 143 and draws the magnetic particles back to the bottom of the wells. This wash process 141,143,145 is repeated three times to thoroughly cleanse the magnetic particles, and dilute and remove all supernatant.

Figure 13:
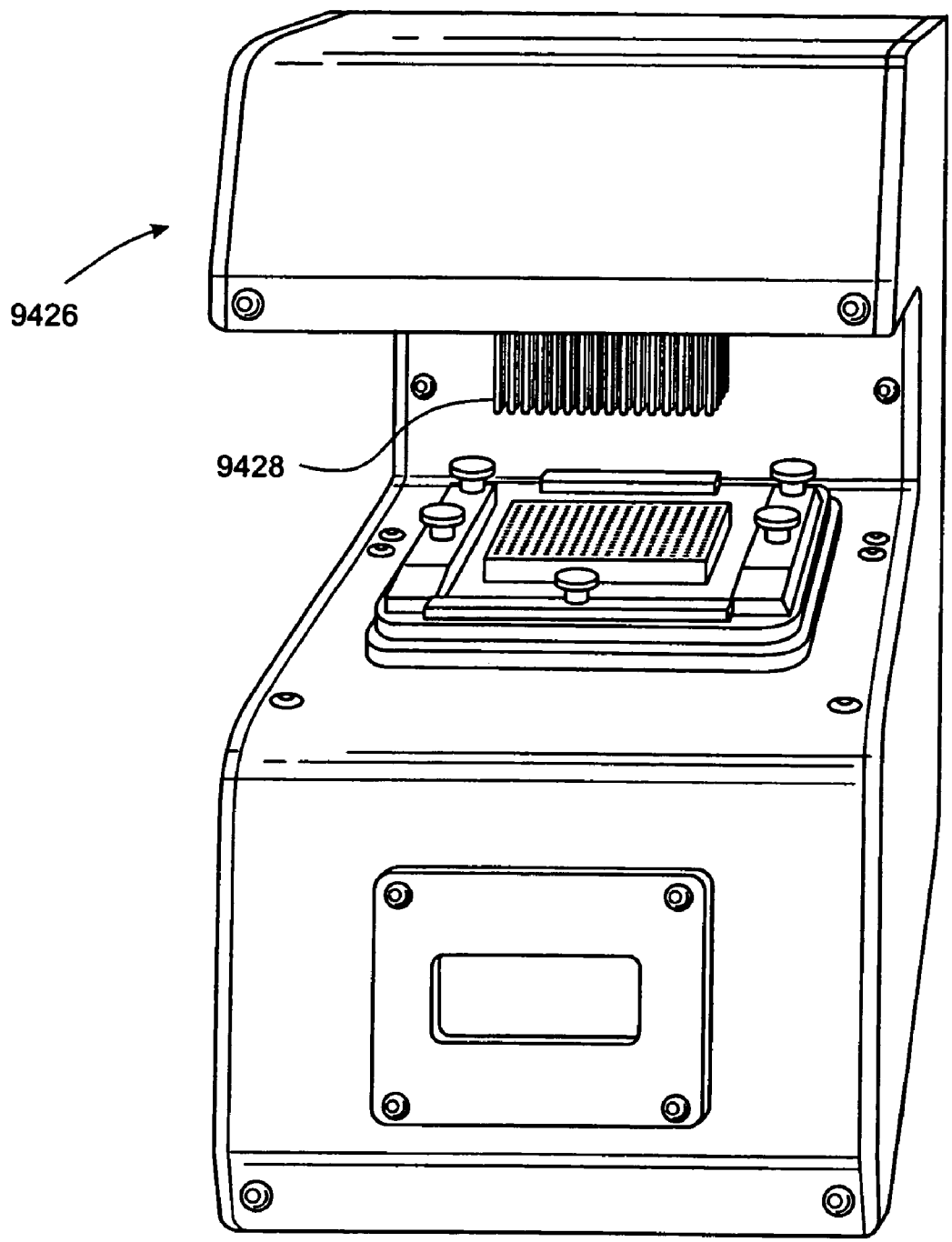
FIG. 13 illustrates a preferred device for drying samples.
Figure 14:
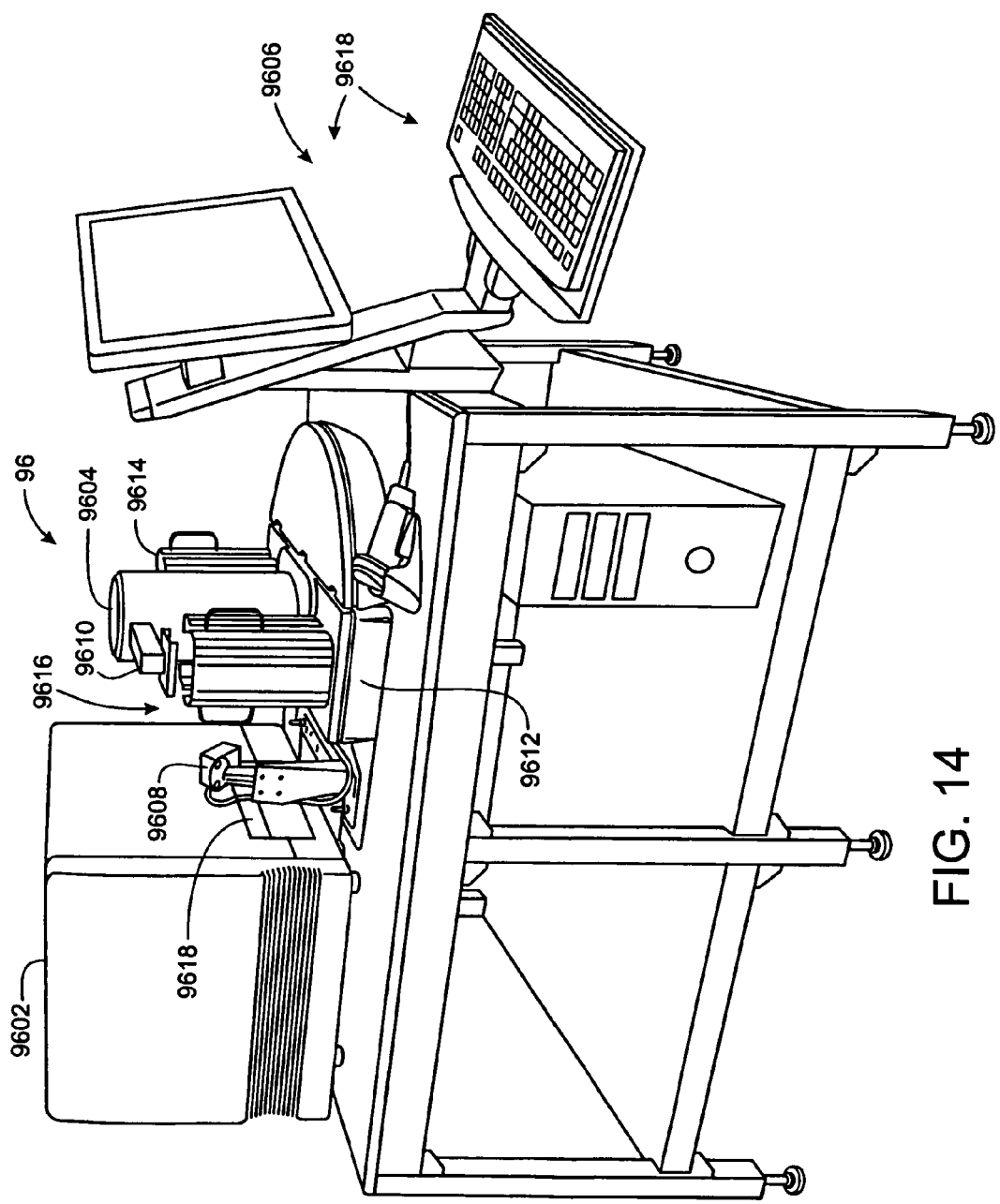
FIG. 14 illustrates a preferred device for performing the functions of a Detection Station as described herein.

Once the magnetic particles are thoroughly washed, computer 9412 permits the magnetic particles in each well to air dry 147. In the preferred embodiment, shown in FIG. 13, the operator moves the primary master well container 6 to a dryer 9426 (an "ULTRAVAP dryer by PORVAIR SCIENCES, UK) having 384 tubules disposed in a 16×24 array 9428 that are configured to be simultaneously inserted into each of the wells of the primary master well container 6 and to supply warm, dry air thereto. In an alternative method, computer 9412 causes material handler 9408 to direct compressed dry nitrogen gas into each well of the primary master well container 6, drying the magnetic particles out in place while the container is in the magnetic field. Alternatively the samples can be permitted to air dry. Once the magnetic particles are completely dry, the primary master well container 6 can be subsequently moved away from the field of magnet 149.

In an alternate embodiment, each well of a wellplate, which contains biological samples, is filled with active magnetically responsive magnetic particles. The magnetic particles may have a functional group, such as carboxylate, surface chemistry. The deck of the isolation station has a mixing mechanism to prevent the settling out of the magnetic particles from solution. The magnetic particles are dispensed into the wells via a syringe pump system. A syringe pump dispenses a binding buffer into the well containing the raw biological material and active magnetic particles. The dispensing itself may facilitate proper mixing of the samples. Alternatively, a 96-tip or 384-tip pipetting head on the workstation may be used to gently mix the samples by gently pipetting up and down several times. Using the 96-tip or 384-tip mixing methodology requires washing of the pipette tips between each usage.

The binding reagent for magnetic particles, having a functional group or surface chemistry attached to the outside, is composed of 20% polyethylene glycol (PEG) 8000, 0.02% Sodium Azide and 2.5 M Sodium Chloride. The PEG allows for the hydrogen binding of water, which causes concentration of the DNA. The high salt condition of the mixture enables the DNA to non-specifically bind to the surface chemistry of the magnetic particles.

The magnetic particles, binding reagent and raw biological material are allowed to incubate at room temperature for ten minutes. After the incubation, a magnetic separator makes contact with the bottom of the 384 wellplate. The magnet will remain in contact for several minutes. The magnetic particles, with attached mammalian genomic DNA, for example, will be magnetically attracted to the bottom of the 384 wellplate, forming a pellet of magnetic particles. Without removing the magnetic separator, the particle free clear supernatant will be aspirated away from the magnetic particles. The supernatant, containing cellular debris, proteins and a high salt concentration will be discarded.

The magnetic separator is removed and a syringe pump dispenses the first wash buffer. The dispensing itself may facilitate proper resuspension of the magnetic particles. Alternatively, a 96-tip or 384-tip pipetting head on the workstation may be used to gently mix the samples by gently pipetting up and down several times. Using the 96-tip mixing methodology requires washing of the pipette tips between each usage.

The first wash buffer is composed of 70% ethanol and 30% de-ionized water. The resuspension of the magnetic particles in the first wash buffer aids in the removal of excess salts and cellular debris. Washing provides for better DNA preparation.

After washing with the first wash buffer, a magnetic separator makes contact with the bottom wellplate. The magnet remains in contact with the wellplates for several minutes. The magnetic particles, with attached genomic DNA will be magnetically attracted to the bottom of the wellplate, forming a pellet of magnetic particles. Without removing the magnetic separator, the magnetic particle free clear supernatant is aspirated away from the magnetic particles. The supernatant, containing cellular debris, proteins and a high salt concentration is discarded. The magnetic particle washing steps may or may not be repeated.

The wellplates with magnetic particles pelletized are allowed to air dry or forced-air dried to remove some ethanol contamination. Alternatively, drying may be facilitated with compressed Nitrogen. Once the magnetic particles are sufficiently dry the magnetic separator will be removed.

Once the magnetic particles are dry, the operator moves the primary master well container 6 to the screening station liquid handler and directs the computer to command the pipettes to fill the wells with 180 μl of hybridization reagent 3.0M Tetramethylammonium Chloride (TMACL), 50 mM Tris, 4 mM EDTA and 0.01% TWEEN 20 polyoxyethylene sorbitan monolaurate (including the dendrimer and bipartite probe) is added to each well at hybridization temperature. In a one-step reaction one hybridization temperature is used which allows for the simultaneous hybridization of bipartite to both the nucleic acid as well as the dendrimer. If the two binding portions of the bipartite are of significantly different lengths a two-stage hybridization can occur with first hybridization being more stringent than the second.

The samples incubate at the hybridization temperature. The well plate is then moved into the magnetic field of a magnet where the magnetic particles are drawn to the bottom of each well. The supernatant is then aspirated and discarded. Next, the samples are washed twice in 180 μl of wash reagent which is composed of 3.0M Tetramethylammonium Chloride (TMACL), 50 mM Tris, 4 mM EDTA and 0.01% TWEEN 20 polyoxyethylene sorbitan monolaurate (without the dendrimer or probe). Next, the samples are washed once in 180 μl of 95% ethanol as described above. The liquid handler dispenses elution reagent into each sample well. This elution solution is formulated to elute the bound genomic nucleic acid from the magnetic particles. An example of one such elution solution is 1×TBE, or nuclease free water. In the preferred embodiment, the elution solution is 1×TBE. In the preferred embodiment, the elution solution temperature is 22° C. The samples are mixed by aspirating and dispensing. The well plate is then moved into the magnetic field of a magnet where the magnetic particles are drawn to the bottom of each well. The supernatant is then aspirated and 130 μl is transferred to a clean optical fluorescent plate. The samples are then placed in a TECAN LSA300 and the fluorescence is detected.

After fluorescent detection the computer then directs the pipettes to aspirate a small amount (100 μl) of genomic nucleic acid, dendrimer and probe mixture and to transfer 159 the small amount from each well into a corresponding well of a clean optical 384-well container that is also mounted on deck 9406. The operator scans 161 a barcode accession number on the optical container and computer 9412 transfers the scanned accession number to process controller 26, which then transfers it to LIMS 24. The operator takes this optical container to a UV spectrometer (GENIOS, by TECAN of Raleigh-Durham, N.C.), and directs the UV spectrometer to optically scan the optical container, by making an A260 measurement 163. This measurement is electronically transferred 112 to LIMS 24 over a data communications link.

If another fully automated system is desired, the magnetic separator can be automated and rise from the bottom of the workstation and make contact with bottoms of all primary well containers simultaneously.

In the preferred embodiment for the biological sample, the genomic nucleic acid is not sonicated after separation from the cellular debris. The genomic nucleic acid includes at least a portion of intact nucleic acid. Unsonicated nucleic acid is recovered in the condition it is found in the lysate. Thus, if the genomic nucleic acid is intact in the lysate, it is intact (i.e., unfragmented) as attached to the magnetic particles. The sample contains at least a portion of intact genomic nucleic acid.

In certain types of samples, such as embryos, the genomic nucleic acid is substantially intact. In one embodiment, the genomic nucleic acid can be sonicated before or after separation with the magnetic particles. When the biological tissue is embryonic sonication is preferred. Sonication can be done by any conventional means such as a fixed horn instrument or plate sonicator. In the one embodiment, the genomic nucleic acid is sonicated for five seconds to produce nucleic acid fragments. Although there is a wide range of fragments from about 100 base pairs to up to 20 kilobases, the average size of the fragment is around about 500 base pairs.

The screening station 95 in the present embodiment employs hybridization of a labeled probe. The direct labeling technique utilizes the complimentary binding of a nucleic acid probe. The probe may be structurally single stranded RNA or DNA or in any conformation, such as the preferred embodiment of the rigid lattice structure of a dendrimer which contains both single and double stranded DNA. Each probe will contain at least one fluorescent, radioactive or colorimetric staining molecule per probe, such as cyanine, horseradish peroxidase (HRP), antibiotin molecule or any other fluorescent signal generation reagent. The labeled nucleic acid probe complementarily binds to a portion of the genomic nucleic acid sequence immobilized on the glass microfibers of the magnetically responsive magnetic particles.

More specifically, in one embodiment, the magnetically responsive particle with the attached genomic nucleic acid is combined with a quaternary ammonium salt based preheated hybridization solution. The probe or oligonucleotide is directly ligated to the dendrimer molecule. This probe-dendrimer complex is then hybridized to the immobilized nucleic acid on the silica magnetic particles. Alternatively, the dendrimer may have a standard capture arm ligated thereto, which is capable of hybridizing to one portion of a bipartite probe while the other element of the bipartite probe is simultaneously hybridizing to the nucleic acid immobilized on the magnetic particle. The double hybridization allows for the detection of the target genetic sequence. In the preferred embodiment, the tetramethylammonium chloride (TMAC or TMACL) is used. The hybridization solution is comprised of 3.0M Tetramethylammonium Chloride (TMACL), 50 mM Tris, 4 mM EDTA and 0.01% TWEEN polyoxyethylene sorbitan monolaurate. Alternatively, hybridization solutions may include 3.0M Tetramethylammonium Chloride (TMACL), 50 mM Tris, 4 mM EDTA, 0.01% TWEEN 20 polyoxyethylene sorbitan monolaurate and 5×Denhardt's or 3.0M Tetramethylammonium Chloride (TMACL), 50 mM Tris, 4 mM EDTA, 0.1% SDS and 5×Denhardt's. To 11 μl of a 1:1000 dilution of Alexa 647 dimer dendrimer (GENISPHERE, Hatfield Pa.) was added to 4,989 μl of hybridization reagent. The dendrimer probe had a standard capture arm ligated to it, known as Cap035. Additionally, 238 μl of 1:1,000,000 dilution of the bipartite probe was added to the 5.0 mls of hybridization reagent. The solution is heated 5° C. below the calculated melting temperature of the dendrimer arm. In the preferred embodiment, the solution is heated to 7° C. below the melting temperature. The melting temperature is calculated depending on the length of the oligonucleotide arm attached to the dendrimer with no consideration given to any linker or extender double stranded DNA sequences. 180 μl of the preheated dendrimer-probe hybridization solution is added to the magnetic particles. The hybridization solution and the magnetic particles are thoroughly mixed. The magnetic particles in the hybridization solution are allowed to incubate at 7° C. below the calculated melting temperature for 60 minutes to 4 hours.

After incubating in the hybridization buffer, the magnetic separator makes contact with the bottom wellplate of FIG. 12. The magnet remains in contact with the wellplates for several minutes. The magnetic particles, with attached genomic DNA and hybridized dendrimer-probe complex are magnetically attracted to the bottom of the wellplate, forming a pellet of magnetic particles. Without removing the magnetic separator, the magnetic particle free clear supernatant is aspirated away from the magnetic particles. The supernatant, containing unbound dendrimer is discarded.

Washing continues by adding 200 µl of a preheated wash solution to the magnetic particle pellet. The wash solution may be 3.0M Tetramethylammonium Chloride (TMACL), 50 mM Tris, 4 mM EDTA and 0.01% TWEEN 20 polyoxyethylene sorbitan monolaurate. The wash solution is the same constituents as the respective hybridization buffer minus the fluorescent dendrimer and probe. The magnetic particle bed and the warm wash buffer is thoroughly mixed.

After washing, a magnetic separator contacts the bottom wellplate. The magnet remains in contact with the wellplates for several minutes. The magnetic particles, with attached genomic DNA and hybridized dendrimer are magnetically attracted to the bottom of the wellplate, forming a pellet of magnetic particles. Without removing the magnetic separator, the magnetic particle-free clear supernatant is aspirated away from the magnetic particles. The supernatant, containing unbound dendrimer is removed.

Washing continues by adding 180 µl of a preheated wash solution to the magnetic particles pellet and thoroughly mixing. Immediately after mixing, a magnetic separator makes contact with the bottom wellplate. The magnet remains in contact with the wellplates for several minutes. The magnetic particles, with attached genomic DNA and hybridized dendrimer are magnetically attracted to the bottom of the wellplate, forming a pellet of magnetic particles. Without removing the magnetic separator, the magnetic particle free clear supernatant are aspirated away from the magnetic particles. The supernatant, containing unbound dendrimer is discarded. This may or may not be repeated a number of times. Alternatively, it has been shown that the molarity of the TMACL can be reduced and washing may occur at less than 3.0 M TMACL.

Washing continues by adding 180 µl of a 95% EtOH wash solution to the magnetic particles pellet and thoroughly mixing. Immediately after mixing, a magnetic separator makes contact with the bottom wellplate. The magnet remains in contact with the wellplates for several minutes. The magnetic particles, with attached genomic DNA and hybridized dendrimer are magnetically attracted to the bottom of the wellplate, forming a pellet of magnetic particles. Without removing the magnetic separator, the magnetic particle-free clear supernatant is aspirated away from the magnetic particles.

Once the magnetic separator is removed and the magnetic particles are almost dry, a syringe pump will dispense Suspension Buffer. The dispensing may facilitate proper re-suspension of the magnetic particles. Alternatively, a 96-tip or 384-tip pipetting head on the workstation may be used to gently mix the samples by gently pipetting up and down several times. Using the 96-tip or 384-tip mixing methodology requires washing of the pipette tips between each usage.

The suspension buffer is composed of an aqueous solution such as 1× Tris Borate EDTA (TBE), which is the preferred embodiment. Alternatively, TE buffer or nuclease free water can be used. The function of these compounds is to elute the bound genomic nucleic acid and probe-dendrimer complex from the magnetic particles. The unbound dendrimer functions as a reported molecule free in solution After re-suspending the genomic nucleic acid or disrupting the dendrimer-probe-nucleic acid complex and releasing the dendrimer into solution, a magnetic separator makes contact with the wellplate. The magnet will remain in contact with the wellplate for several minutes. The magnetically responsive magnetic particles, without the attached genomic nucleic acid or dendrimer-probe complex will be magnetically attracted to the bottom of the wellplate, forming a pellet of magnetic particles. Without removing the magnetic separator, the magnetic particle free clear supernatant will be pipetted away from the magnetic particles. The supernatant, containing fluorescent dendrimer will be pipetted into a clean fluorescent 384 wellplate and scanned.

Another approach which is also contemplated involves a double isolation method. Either initial isolation methodology, as describes above, is employed. However after the genomic nucleic acid (DNA or RNA) is sufficiently washed it is eluted from the magnetic particles. The DNA suspension is then mixed with traditional sodium based hybridization solution such as a final 6×SSC, 1 mM EDTA, 50 mM Tris, 5×Denhardts, and 0.1% SDS or Genisphere's buffer 13 (0.5M $NaPO_4$, 1% SDS, 2 mM EDTA, 2×SSC 4×Denhardts), buffer 14 (50% Formamide, 8×SSC, 1% SDS, 4×Denhardts) or buffer 7 (40% Formamide, 4×SSC, 1% SDS, 2×Denhardts) Hybridization of a dendrimer with a directly ligated capture sequence to unbound nucleic acid may occur in a solution environment. Alternatively, the dendrimer, probe (such as a bipartite) and the unbound genomic nucleic acid may also hybridize in an aqueous environment. The hybridization occurs for 1 to 24 hours. The DNA nucleic acid probe duplexes are then recaptured by the addition of magnetic particles. In the preferred embodiment glass microfibers are attached to the outside of the magnetically responsive particle. The deck of the isolation station has a mixing mechanism to prevent the settling out of the magnetic particles from solution. The magnetic particles will be dispensed into the wells via a syringe pump system. A syringe pump will dispense a binding buffer into the well containing the DNA dendrimer duplex and active magnetic particles. The binding buffer is preferably 4.5-3.0M Tetramethylammonium Chloride (TMACL), 50 mM Tris, 4 mM EDTA and 0.01% TWEEN 20 polyoxyethylene sorbitan monolaurate. The dispensing itself may facilitate proper mixing of the samples. Alternatively, a 96-tip or 384-tip pipetting head on the workstation may be used to gently mix the samples by gently pipetting up and down several times. Using the 96-tip or 384-tip mixing method requires washing of the pipette tips between each usage.

The magnetic particles, binding buffer and genomic DNA nucleic acid probe duplex material are allowed to incubate at room temperature for several minutes. After the incubation, a magnetic separator will make contact with the bottom of the 384 wellplate. The magnet remains in contact for several minutes. The magnetic particles, with attached genomic DNA nucleic acid probe duplexes, are magnetically attracted to the bottom of the 384 wellplate, forming a pellet of magnetic particles. Without removing the magnetic separator, the magnetic particle-free clear supernatant is aspirated away from the magnetic particles. The supernatant, containing initial hybridization reagent, proteins and a high salt concentration are discarded.

The magnetic separator of FIG. 12 is removed and a syringe pump dispenses a first wash buffer. The dispensing itself may facilitate proper re-suspension of the magnetic particles. Alternatively, a 96-tip or 384-tip pipetting head on the workstation can be used to gently mix the samples by gently pipetting up and down several times. Using the 96-tip mixing method requires washing of the pipette tips between each usage.

The first wash buffer is composed of the same constituents as the binding buffer. The preferred embodiment is the use of tetramethylammonium chloride compound.

After washing twice with the first wash buffer, a magnetic separator contacts the bottom wellplate. The magnet remains in contact with the wellplates for several minutes. The magnetic particles, with attached genomic DNA dendrimer duplexes are magnetically attracted to the bottom of the wellplate, forming a pellet of magnetic particles. Without removing the magnetic separator, the particle-free clear supernatant is aspirated away from the magnetic particles. The supernatant, containing unbound dendrimer and loosely bound genomic DNA is discarded. The particle washing steps may or may not be repeated with increasing stringency.

Washing continues by adding 180 µl of a 95% EtOH wash solution to the bead pellet and thoroughly mixing. Immediately after mixing, a magnetic separator makes contact with the bottom wellplate. The magnet remains in contact with the wellplates for several minutes. The magnetic particles, with attached genomic DNA and hybridized dendrimer are magnetically attracted to the bottom of the wellplate, forming a pellet of magnetic particles. Without removing the magnetic separator, the particle-freeclear supernatant is aspirated away from the magnetic particles.

Once the magnetic separator is removed a syringe pump will dispense suspension Buffer. The dispensing can facilitate proper resuspension of the magnetic particles. Alternatively, a 96-tip or 384-tip pipetting head on the workstation may be used to gently mix the samples by gently pipetting up and down several times. Using the 96-tip or 384-tip mixing methodology requires washing of the pipette tips between each usage.

The suspension buffer is composed of an aqueous solution such as 1×TBE, which is the preferred embodiment. The function is to elute the bound genomic DNA from the magnetic particles and to release the genomic nucleic acid, dendrimer and probe into solution. The unbound labeled probe functions as a reported molecule free in solution.

In an alternative embodiment, the genomic nucleic acid, dendrimer and probe may not be eluted into solution. Rather detection may occur while the complex is still immobilized on the beads. A flow cytometer can detect the fluorescence on the magnetic particles.

In an alternative embodiment, the labeled nucleic acid probe is a dendrimer which may be a dimer, two layered dendrimer four layer dendrimer. These dendrimer which are typically labeled with fluorescent molecules can have a hapten element attached to their structure.

After resuspending the genomic nucleic acid, dendrimer and probe into solution, a magnetic separator makes contact with the wellplate. The magnet will remain in contact with the wellplate for several minutes. The magnetic particles, without the attached genomic nucleic acid, dendrimer and probe complex will be magnetically attracted to the bottom of the wellplate, forming a pellet of magnetic particles. Without removing the magnetic separator, the particle free, clear supernatant will be pipetted away from the magnetic particles. The supernatant, containing fluorescent dendrimer will be pipetted into a clean fluorescent 384 wellplate and scanned.

Figure 9:
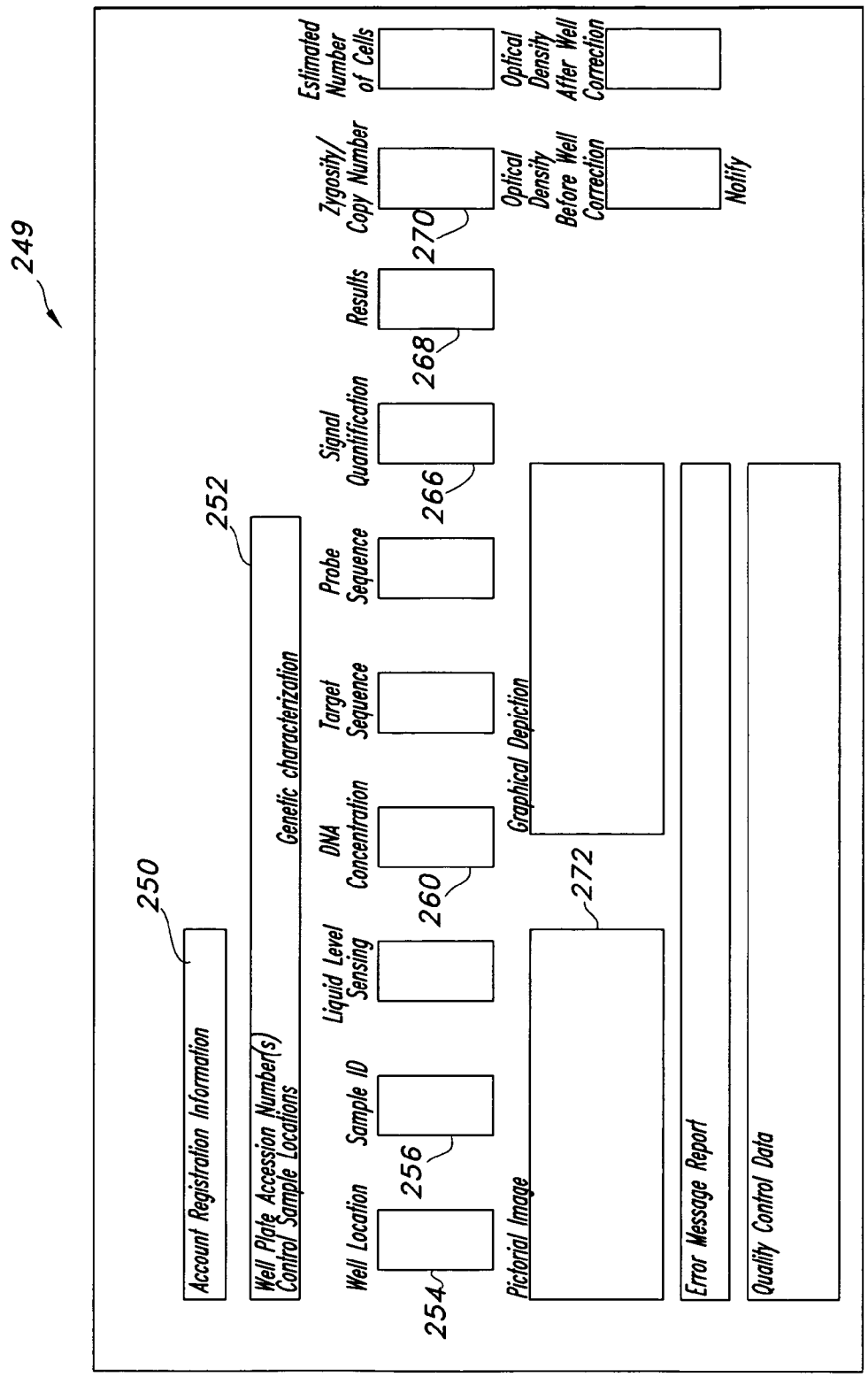
FIG. 9 is a screen display illustrating a document on the transgenic screening laboratory 20's web site relating to an outcome file.

Now referring to FIG. 9, LIMS 24 now prepares the outcome report 249. Several calculations are performed before they are posted to the outcome report 249. In the preferred embodiment, such calculations include the evaluation of all replicates per sample. Calculating the relationship between the experimental quantified signal and the quantified signals of designated control may elucidate the copy number, zygosity or mosaic nature of the sample. The ratio for homozygous individuals should be twice the ratio of heterozygous individuals.

Now referring to FIG. 9, the sample outcome report 249 may include account registration 250, well plate container 2 barcode number(s) (i.e. accession numbers) 252, control sample locations 252 and genetic characterization of the designated control 252. Additionally, the outcome report 249 may include well location 254, sample identification 256, nucleic acid concentration 260, signal quantification 266, qualitative results 268, zygosity/copy number 270, quantitative analysis via comparison to designated control signal strengths allowing for copy number estimation, zygosity or mosaic nature 270. The outcome report 249 may also include a picture file (email) or pictorial representations of results 272 as shown in FIG. 10. Additionally, information gathered at the request of the remote user 1 from optimization and sequence confirmation quality control data and error messages may be included in the outcome report 249. The remote user 1 may choose to have this file electronically sent or choose to be electronically notified. Additionally, remote user 1 has the option to have a hard copy sent via the postal service or facsimile.

Once the LIMS 24 has compiled all the data for the outcome report 249, the outcome report will be sent 7 to the remote user 1. In the preferred embodiment, LIMS 24 will send the report via a remote link 7 to either the remote user 1 or the order manager 22, which can post the results on the web site 16 or via an electronic link 7. The LIMS 24 will keep results available for six months and then the results will be recorded onto a long-term storage disk and archived.

EXAMPLE 1

Mouse Tissue Genotyping with a Bipartite Probe

Specifically, a remote user 1 can contact the screening laboratory 20 and provide a description of the mutation. This description may include information such as the endogenous gene Bgal (also known as Glb1) was disrupted with the deletion of a particular exon with a Neomycin cassette. The gene name may be used to query databases to yield literature specific for this mutation by the screening laboratory 20. The Mouse Genome Informatics (MGI) J:38620, PubMed 9063740, or Medline 97217779 databases with their respective journal numbers, yield the following literature reference: Hahn C N; del Pilar Martin M; Schroder M; Vanier M T; Hara Y; Suzuki K; Suzuki K; d'Azzo A, Generalized CNS disease and massive GM1-ganglioside accumulation in mice defective in lysosomal acid beta-galactosidase., Hum Mol Genet 1997 February; 6(2):205-11.

This reference discloses that a Neomycin cassette was inserted into exon six of the Bgal at an AatII restriction site. The screening laboratory 20 then queries a database such as ENSEMBL. The ENSEMBL database gene identification number is ENSMUSG00000042315. The genomic sequence with the exons and restriction sites is identified.

The screening laboratory 20 queries a database such as ENSEMBL database. This query yields sequence data, which is the designated genetic sequence. By knowing the endogenous bases that have been deleted, the screening laboratory 20 can take the designated genetic sequence, or portion thereof, and build the probe(s) as to be informative for screening. Moreover, if there are a large number of bases that have been deleted or added, the screening laboratory 20 may probe anywhere inside the sequence.

The Neomycin coding sequence, or mutation sequence, does not naturally occur in mice. The same mechanism of identifying the designated genetic sequence using the National Center for Biotechnology Information database and building anywhere inside the sequence is used. The neomycin coding sequence or designated genetic sequence is:

(SEQ ID NO.1)
CATTGAACAAGATGGATTGCACGCAGGTTCTCCGGCCGCTTGGGTGGAGA

GGCTATTCGGCTATGACTGGGCACAACAGACAATCGGCTGCTCTGATGCC

GCCGTGTTCCGGCTGTCAGCGCAGGGGCGCCCGGTTCTTTTTGTCAAGAC

CGACCTGTCCGGTGCCCTGAATGAACTGCAGGACGAGGCAGCGCGGCTAT

CGTGGCTGGCCACGACGGGCGTTCCTTGCGCAGCTGTGCTCGACGTTGTC

ACTGAAGCGGGAAGGGACTGGCTGCTATTGGGCGAAGTGCCGGGGCAGGA

TCTCCTGTCATCTCACCTTGCTCCTGCCGAGAAAGTATCCATCATGGCTG

ATGCAATGCGGCGGCTGCATACGCTTGATCCGGCTACCTGCCCATTCGAC

CACCAAGCGAAACATCGCATCGAGCGAGCACGTACTCGGATGGAAGCCGG

TCTTGTCGATCAGGATGATCTGGACGAAGAGCATCAGGGGCTCGCGCCAG

CCGAACTGTTCGCCAGGCTCAAGGCGCGCATGCCCGACGGCGAGGATCTC

GTCGTGACCCATGGCGATGCCTGCTTGCCGAATATCATGGTGGAAAATGG

CCGCTTTTCTGGATTCATCGACTGTGGCCGGCTGGGTGTGGCGGACCGCT

ATCAGGACATAGCGTTGGCTACCCGTGATATTGCTGAAGAGCTTGGCGGC

GAATGGGCTGACCGCTTCCTCGTGCTTTACGGTATCGCCGCTCCCGATTC

GCAGCGCATCGCCTTCTATCGCCTTCTTGACGAGTTCTTCTG

Upon identification of the designated genetic sequence two other software programs are utilized. The first of these programs is a blast program that identifies homologies between the designated genetic sequence and the endogenous genome of the mouse, as well as other species.

The second of these programs is repeat masking program, such as Repeat Master Web Server. This program identifies areas in the designated genetic sequence that are highly repetitive, making them less than ideal locations to build a probe. If such areas are found in the designated genetic sequence they are masked by replacing the normal nucleotide designation A, C, G or T with the letter N or X. Oligo Ect software program is then utilized to generate a bipartite probe. The software allows the screening laboratory 20 to identify secondary structures that may form when designing the bipartite such as heterodimers and homodimers. A print out from this software program is shown in Table 2.

TABLE 2

SEQUENCE:

(SEQ ID NO. 2)
5' ATT GCC TTG TAA GCG ATG TGA TTC TAT TGG ATG GAG
AGG CTA TTC GGC TAT GAC TGG GCA CAA CAG ACA AT 3'
1.44 nM/OD
31.79 ug/OD
MW = 22.1 k (one strand)
Primer to Target Tm(by % GC) = 90.5° C.

TABLE 2-continued

COMPOSITION:

| A     | 19.00 | 26.8% |
|-------|-------|-------|
| C     | 12.00 | 16.9% |
| G     | 20.00 | 28.2% |
| T     | 20.00 | 28.2% |
| X     |   .00 |  0.0% |
| A + T | 39.00 | 54.9% |
| C + G | 32.00 | 45.1% |

STEM LOOP STRUCTURE:

(SEQ ID NO. 3)
56
 | 54
CGGGTCAGTATCGGCTTATCGGAGAGGTAGGTTATCTTAGTGTAGCGAAT
GTTCCGTTA 5'
A< |||
  CAACAGACAAT 3'
  | 66
  64
G = 0.6 kcal/mol
loop Tm = 9° C.

HOMODIMER:

(SEQ ID NO. 4)
5' ATTGCCTTGTAAGCGATGTGATTCTATTGGATGGAGAGGCTATTCGG
CTATGACTGGGCACAACAGACAAT 3'
(SEQ ID NO. 5)
||||:::::  ::::::  :::::|||
3'TAACAGACAACACGGGTCAGTATCGGCTTATCGGAGAGGTAGGTTAT
CTTAGTGTAGCGAATGTTCCGTTA 5'
Homodimer Tm = 24.3° C.

A bipartite probe is designed to have one portion hybridize to the designated genetic sequence of neomycin. In this case the bipartite probe would have a sequence of: ATTGCCTTG-TAAGCGATGTGATTCTATTGGATG-GAGAGGCTATTCGGCTATGACT GGGCACAACAG. (SEQ ID NO. 6) The TGGAGAGGCTATTCGGCTAT-GACTGGGCACAACAG (SEQ ID NO. 7) portion of bipartite indicated hybridizes to the target genetic sequence of the designated genetic sequence which is:

(SEQ ID NO.1)
CATTGAACAAGATGGATTGCACGCAGGTTCTCCGGCCGCTTGGGTGGAGA

GGCTATTCGGCTATGACTGGGCACAACAGACAATCGGCTGCTCTGATGCC

GCCGTGTTCCGGCTGTCAGCGCAGGGGCGCCCGGTTCTTTTTGTCAAGAC

CGACCTGTCCGGTGCCCTGAATGAACTGCAGGACGAGGCAGCGCGGCTAT

CGTGGCTGGCCACGACGGGCGTTCCTTGCGCAGCTGTGCTCGACGTTGTC

ACTGAAGCGGGAAGGGACTGGCTGCTATTGGGCGAAGTGCCGGGGCAGGA

TCTCCTGTCATCTCACCTTGCTCCTGCCGAGAAAGTATCCATCATGGCTG

ATGCAATGCGGCGGCTGCATACGCTTGATCCGGCTACCTGCCCATTCGAC

CACCAAGCGAAACATCGCATCGAGCGAGCACGTACTCGGATGGAAGCCGG

TCTTGTCGATCAGGATGATCTGGACGAAGAGCATCAGGGGCTCGCGCCAG

CCGAACTGTTCGCCAGGCTCAAGGCGCGCATGCCCGACGGCGAGGATCTC

GTCGTGACCCATGGCGATGCCTGCTTGCCGAATATCATGGTGGAAAATGG

CCGCTTTTCTGGATTCATCGACTGTGGCCGGCTGGGTGTGGCGGACCGCT

ATCAGGACATAGCGTTGGCTACCCGTGATATTGCTGAAGAGCTTGGCGGC

-continued

GAATGGGCTGACCGCTTCCTCGTGCTTTACGGTATCGCCGCTCCCGATTC

GCAGCGCATCGCCTTCTATCGCCTTCTTGACGAGTTCTTCTG

Additionally, the ATTGCCTTGTAAGCGATGTGATTC-TATTGGA (SEQ ID NO. 8) portion of the bipartite probe hybridizes to the Capo35 capture arm of the dendrimer which has a sequence of: 5'-TCC AAT AgA ATC ACA TCg CTT ACA Agg CAA T. (SEQ ID NO. 9)

A biological sample in the form of a mouse tail biopsy is submitted via FEDEX (Memphis, Tenn.) overnight delivery service to the screening laboratory 20 from the remote user 1. Each sample occupies one well of a 96-well source well container.

A lysis reagent (made of 2.5 t of proteinase K (VWR EM-24568-3) and 147.5 µl of Nuclei Lysing Solution (PROMEGA Corporation, Madison, Wis. A7943) per sample)) is gently mixed and poured into a 25 ml trough or reservoir and is placed on the deck of a TECAN GENESIS liquid handling workstation (Research Triangle Park, N.C.). The liquid handler dispenses 150 µl of the lysis reagent in to each sample well of the source well container 2. The well plate is then placed in a 55° C. oven for three hours. The well plate is then placed back on the deck of the TECAN GENESIS liquid handling workstation (Research Triangle Park, N.C.). The liquid handler aspirates 50 µl of each sample and dispenses it into a 384 well primary master well container (FISHER SCIENTIFIC #NC9134044). Once all of the samples are transferred, the primary master well container is moved to the deck of the Isolation Station Purification Station 94.

One-hundred and sixty microliters of SV Lysis reagent (PROMEGA Corporation, Madison Wis., # Z305X), a chaotropic salt, are added to each sample. Next, 30 µl of magnetic particles (PROMEGA Corporation, #A220X) are added and the well components are mixed. The well plate is then moved into the magnetic field of a magnet where the magnetic particles are drawn to the bottom of each well. The supernatant is then aspirated and discarded. Next, the samples are washed three times in 160 µl of 95% ethanol as described above. After the fourth ethanol wash, the microwell container is placed on a 384 tip dryer for 11 minutes. Then the microwell container is moved back to the deck of the liquid handler and 180 µl of hybridization reagent 3.0M Tetramethylammonium Chloride (TMACL), 50 mM Tris, 4 mM EDTA and 0.01% TWEEN 20 polyoxyethylene sorbitan monolaurate (including the dendrimer and bipartite probe) is added to each well at 72° C., the hybridization temperature. In a one-step reaction, only one hybridization temperature is used which allows for the simultaneous hybridization of bipartite to both the nucleic acid as well as the dendrimer. If the two binding portions of the bipartite are significantly different in lengths a two-stage hybridization can occur with first hybridization being more stringent than the second.

The samples incubate at the hybridization temperature for 60 minutes. The well plate is then moved into the magnetic field of a magnet where the magnetic particles are drawn to the bottom of each well. The supernatant is then aspirated and discarded. Next, the samples are washed twice in 180 µl of wash reagent which is composed of 3.0M Tetramethylammonium Chloride (TMACL), 50 mM Tris, 4 mM EDTA and 0.01% TWEEN 20 polyoxyethylene sorbitan monolaurate (without the dendrimer or probe). Next, the samples are washed once in 180 µl of 95% ethanol as described above. The liquid handler dispenses 200 µl of 1×TBE elution reagent into each sample well. The samples are mixed by aspirating and dispensing. The well plate is then moved into the magnetic field of a magnet where the magnetic particles are drawn to the bottom of each well. The supernatant is then aspirated and 130 µl is transferred to a clean optical fluorescent plate. The samples are then placed in a TECAN LSA300 and the fluorescence is detected.

One hundred microliters of the genomic nucleic acid, dendrimer and probe elution is transferred from the fluorescent detection plate to a 384 well optical storage plate (FISHER SCIENTIFIC, #08-772136) for optical density analysis. An $A_{260}$ reading of the storage plate read is performed with a TECAN GENIOS spectrometer (Research Triangle Park, N.C.). This reading shows nucleic acid is present at the desired concentration of 0.5 O.D. units, but a range of 0.1 to 1.5 OD units is acceptable. The results are shown in Tables 3 and 4.

TABLE 3

Bipartite One-Step Hybridization

| Position | Raw intensity | Background | Net Mean | Net Sum | Result |
|---|---|---|---|---|---|
| 1 1-1:1 | 4,292 | 1,557 | 2,735 | 30,150,639 | WT |
| 5 1-3:1 | 4,393 | 1,121 | 3,273 | 36,076,293 | WT |
| 9 1-5:1 | 4,317 | 1,051 | 3,265 | 35,998,667 | WT |
| 1 1-1:1 | 6,462 | 1,168 | 5,294 | 58,360,018 | KO |
| 5 1-3:1 | 6,781 | 1,151 | 5,630 | 62,061,905 | KO |
| 9 1-5:1 | 6,330 | 1,178 | 5,152 | 56,793,715 | KO |
| 1 1-1:1 | 2,169 | 1,025 | 1,145 | 12,618,679 | Blanks |
| 5 1-3:1 | 2,215 | 999 | 1,216 | 13,407,251 | Blanks |

TABLE 4

Optical Density post hybridization

| | |
|---|---|
| GENios; Serial number: 12900400173; Firmware: V 4.60 - 09/00 GENios; XFLUOR4 Version: V 4.5 | |
| Date: | Apr. 5, 2005 |
| Time: | 17:16 |
| Comment to this measurement: | Absorbance |
| Measurement mode: | 260 |
| Measurement wavelength: | 5 nm |
| Number of flashes: | NUN384ft.pdf |
| Plate definition file: | A5 - P6 |
| Part of the plate: | Temperature: 21.7° C. |

| Rawdata | | |
|---|---|---|
| <> | OD | Sample |
| A | 0.4051 | WT |
| B | 0.4158 | WT |
| C | 0.4074 | WT |
| D | 0.4272 | KO |
| E | 0.4340 | KO |
| F | 0.4381 | KO |
| G | 0.0990 | Blanks |
| H | 0.1058 | Blanks |
| I | | |
| J | | |

EXAMPLE 2

Single Nucleotide Polymorphism Genotyping

A single nucleotide polymorphism (SNP) is a mutation that affects only one base in the genetic sequence. These mutations occur naturally or can be engineered into a subject. Although, SNPs occur in both humans and mice the tissue source for this experiment was a mouse tail biopsies. Once the bioinformatics and SNP sequence information is acquired a probe is created that can individually discriminate the genotype. Alternatively, two probes may be created. The first probe determines if the sequence of the mutant is present by the probe being perfectly homologous to the mutant condition. The second probe determines if the endogenous DNA sequence is present. The second probe is perfectly homogolous to the endogenous sequence. The results are then determined by evaluating both pieces of information to determine mutants from nonmutant individuals. Mutations that differ at two or more bases can also be genotyped using this method.

Specifically, a remote user 1 contacts the screening laboratory 20 and provides a mouse vendor stock number. The screening laboratory 20 can then use this number to query a vendor's database, which yields a description. This particular description states that the mutant Apc$^{Min}$ allele has a T to A transversion at nucleotide 2549. This point mutation changes codon 850 to a pre-mature stop codon. The ENSEMBL database is then queried for the transcript sequence which has an ENSEMBL database Transcript Identification number of ENSMUST00000079362. This is the designated genetic sequence. The 850th codon is identified.

(SEQ ID NO. 10)
GAGCTTCGGGCGAAGGCCCGGGAGCAGCGGACCGAGGCTGGCGCGATGCT
GTTCCCGGGGAGCGCAGTCGGCTACCGTTGAGGAAGGTGGAGTGAGGAGT
GGCCCTTCCAGCGCCCCCTATGTACGCCTTCCTGCGCTCGGGGCCGGTCG
CCGCGTTGCCCGCCTCCGTACCGCCCGTGACTCTCGGGGCCCGGAGCTCC
GGCGGCGGCCGGGGTCGAGTCCCGGGGAGGGGAGGCGCCCGGGCGGCGC
CCGAGCTTGCGGCCGCGGAGCGAGCGTCTGGCAGGTCCAAGGGTAGCCAA
GGATGGCTGCAGCTTCATATGATCAGTTGTTAAAGCAAGTTGAGGCACTG
AAGATGGAGAACTCAAATCTTCGACAAGAGCTAGAAGATAATTCCAATCA
TCTTACAAAACTGGAAACTGAGGCATCTAATATGAAGGAAGTACTTAAGC
AGCTACAGGGAAGTATTGAAGATGAGACTATGACTTCTGGACAGATTGAC
TTACTAGAGCGTCTTAAAGAATTTAACTTAGATAGTAATTTCCCCGGAGT
GAAACTACGCTCAAAAATGTCCCTTCGCTCCTACGGAAGTCGGGAAGGAT
CTGTATCCAGCCGTTCAGGAGAATGCAGTCCTGTCCCCATGGGGTCATTC
CCAAGAAGAACATTTGTAAATGGAAGCAGAGAGAGTACTGGGTATCTAGA
AGAGCTTGAAAAAGAAAGATCATTACTCCTTGCTGATCTTGACAAAGAAG
AGAAGGAAAAGGACTGGTATTATGCTCAACTTCAGAACCTCACAAAAAGA
ATAGATAGCCTGCCTTTAACTGAAAATTTTTCCTTACAGACAGACATGAC
AAGACGGCAGCTGGAGTATGAAGCAAGGCAGATCAGGGCTGCAATGGAGG
AGCAGCTTGGCACCTGCCAGGACATGGAGAAGCGTGCACAGCGAAGAATA
GCCAGGATCCAGCAAATAGAAAAGGACATACTGCGCGTGCGCCAGCTTTT
ACAGTCCCAGGCGGCGGAAGCGGAGAGGTCATCTCAGAGCAGGCATGATG
CTGCCTCCCATGAAGCTGGCCGGCAGCACGAAGGCCACGGAGTGGCAGAA
AGCAACACCGCAGCCTCCAGTAGTGGTCAGAGTCCAGCTACAGGTGTGGA
TCACGAAACAGCCAGTGTTTTGAGTTCTAGCGGCACGCACTCTGCTCCTC
GAAGGTTGACAAGTCATCTGGGGACAAAGGTGGAAATGGTGTATTCCTTG
TTGTCAATGCTTGGTACTCATGATAAGGACGATATGTCACGAACTTTGCT

AGCTATGTCCAGCTCCCAAGACAGCTGTATATCCATGCGGCAGTCTGGAT
GTCTTCCTCTCCTCATCCAGCTTTTACATGGCAATGACAAAGACTCTGTA
TTGTTGGGAAATTCCCGGGGCAGTAAAGAGGCTCGGGCCAGGGCCAGTGC
AGCACTCCACAACATCATTCACTCACAGCCTGATGACAAGAGAGGCAGGC
GTGAAATCCGAGTCCTTCATCTTTTGGAACAGATACGAGCTTACTGTGAA
ACCTGTTGGGAGTGGCAGGAAGCCCACGAACAAGGCATGGACCAGGACAA
AAACCCAATGCCAGCTCCTGTTGAGCATCAGATCTGTCCTGCTGTGTGTG
TTCTAATGAAGCTTTCATTTGATGAAGAGCATAGGCATGCAATGAATGAA
CTTGGGGGACTGCAGGCCATTGCAGAGTTATTGCAGGTGGACTGTGAGAT
GTATGGGCTTACTAATGACCACTACAGTGTTACTTTAAGACGGTATGCTG
GAATGGCTTTGACAAACTTGACCTTTGGAGATGTTGCCAACAAGGCTACG
CTGTGTTCTATGAAAGGCTGCATGAGAGCACTTGTGGCCCAGTTAAAATC
TGAGAGTGAAGACTTACAGCAGGTTATTGCAAGTGTTTTGAGGAATTTGT
CTTGGCGAGCAGATGTAAATAGCAAAAAGACGTTGAGAGAAGTTGGAAGT
GTGAAAGCATTGATGGAATGTGCTTTGGAAGTTAAAAAGGAATCAACCCT
CAAAAGCGTTTTGAGTGCCTTATGGAACCTGTCTGCACACTGCACTGAGA
ATAAGGCTGACATCTGTGCTGTGGATGGAGCACTGGCATTTCTGGTTGGC
ACCCTCACTTACCGGAGCCAGACAAATACTTTAGCCATTATTGAAAGTGG
AGGTGGGATATTACGGAATGTGTCCAGCTTGATAGCTACAAACGAAGACC
ACAGGCAAATCCTAAGAGAGAACAATTGCCTACAAACTTTATTACAGCAC
TTGAAATCTCACAGCTTGACAATAGTCAGTAATGCATGTGGAACTTTGTG
GAATCTCTCAGCAAGAAATCCTAAAGACCAGGAAGCCTTGTGGGACATGG
GGGCAGTGAGCATGCTCAAGAACCTCATTCATTCCAAGCACAAAATGATT
GCCATGGGAAGTGCAGCAGCTTTAAGGAATCTCATGGCAAACAGACCTGC
AAAGTATAAGGATGCCAATATCATGTCTCCCGGCTCAAGTCTGCCATCCC
TTCACGTTAGGAAACAGAAAGCTCTAGAAGCTGAGCTAGATGCTCAGCAT
TTATCAGAAACCTTCGACAACATTGACAACCTAAGTCCCAAGGCCTCTCA
CCGGAGTAAGCAGAGACACAAGCAGAATCTTTATGGTGACTATGCTTTTG
ACGCCAATCGACATGATGATAGTAGGTCAGACAATTTCAATACTGGAAAC
ATGACTGTTCTTTCACCATATTTAAATACTACGGTATTGCCCAGCTCTTC
TTCCTCAAGGGGAAGTTTAGACAGTTCTCGTTCTGAGAAAGACAGAAGTT
TGGAGAGAGAGCGAGGTATTGGCCTCAGTGCTTACCATCCAACAACAGAA
AATGCAGGAACCTCATCAAAACGAGGTCTGCAGATCACTACCACTGCAGC
CCAGATAGCCAAAGTTATGGAAGAAGTATCAGCCATTCATACCTCCCAGG
ACGACAGAAGTTCTGCTTCTACCACCGAGTTCCATTGTGTGGCAGACGAC
AGGAGTGCGGCACGAAGAAGCTCTGCCTCCCACACACACTCAAACACATA
CAACTTCACTAAGTCGGAAAATTCAAATAGGACATGCTCTATGCCTTATG
CCAAAGTGGAATATAAACGATCTTCAAATGACAGTTTAAATAGTGTCACT
AGTAGTGATGGATATGGTAAAAGAGGCCAAATGAAACCCTCAGTTGAATC
CTATTCTGAAGATGATGAAAGTAAATTTTGCAGTTATGGTCAGTATCCAG

```
CTGACCTAGCCCATAAGATACACAGTGCAAATCATATGGATGATAATGAT
GGAGAACTGGATACACCAATAAATTACAGTCTTAAATATTCAGATGAGCA
GTTGAACTCAGGAAGGCAGAGTCCCTCACAGAATGAAAGGTGGGCAAGAC
CAAAGCATGTGATAGAAGATGAAATAAAGCAAAACGAGCAAAGACAAGCA
AGAAGCCAGAACACCAGTTATCCTGTCTATTCTGAGAATACCGATGACAA
ACACCTCAAATTCCAACCACATTTTGGACAACAAGAATGTGTTTCCCCAT
ATAGGTCAAGGGGAACCAGTGGTTCAGAAACAAATCGAATGGGTTCTAGT
CATGCAATTAATCAAAATGTAAACCAGTCTCTGTGTCAGGAAGATGATTA
TGAAGATGATAAACCTACCAACTACAGTGAACGTTATTCTGAGGAAGAAC
AACATGAAGAAGAAGAAGAGAGACCGACAAATTATAGCATAAAATATAAT
GAAGAGAAACATCATGTGGATCAGCCTATTGATTATAGTTTAAAATATGC
CACTGACATTTCTTCCTCACAAAAACCATCATTTTCATTCTCAAAGAATT
CATCAGCACAAAGCACTAAACCTGAACATCTCTCTCCAAGCAGCGAGAAT
ACAGCTGTACCTCCATCTAATGCCAAAAGGCAGAATCAGCTGCGTCCAAG
TTCAGCACAAAGAAATGGCCAGACTCAAAAAGGCACTACTTGCAAAGTCC
CCTCCATCAACCAAGAAACAATACAGACTTACTGCGTAGAAGACACCCCA
ATATGTTTTTCAAGGTGCAGTTCATTATCATCACTGTCATCAGCTGACGA
TGAAATAGGATGTGATCAGACAACACAGGAAGCAGATTCTGCTAATACTC
TGCAGACAGGAGAAGTAAAAGAGAATGATGTAACTCGGTCAGCTGAAGAT
CCTGCAACTGAAGTTCCAGCAGTGTCCCAGAATGCTAGAGCCAAACCCAG
CCGACTCCAGGCTTCTGGCTTATCTTCAGAATCAACCAGGCATAATAAAG
CTGTTGAGTTTTCTTCAGGAGCCAAGTCTCCCTCCAAAAGTGGTGCTCAG
ACACCCAAAAGTCCCCCAGAACACTATGTCCAGGAGACTCCGCTCGTATT
CAGCAGGTGTACTTCTGTCAGCTCCCTTGACAGTTTTGAGAGTCGCTCCA
TTGCCAGCTCTGTTCAGAGTGAGCCATGTAGTGGAATGGTGAGTGGCATC
ATAAGCCCCAGTGACCTTCCAGATAGTCCTGGGCAGACCATGCCACCAAG
CAGAAGCAAAACCCCTCCACCTCCTCCACAGACAGTGCAGGCCAAGAGAG
AGGTGCCAAAAAGTAAAGTCCCTGCTGCTGAGAAGAGAGAGAGTGGGCCT
AAGCAGACTGCTGTAAATGCTGCCGTGCAGAGGGTGCAGGTCCTTCCAGA
CGTGGATACTTTGTTACACTTCGCCACAGAAAGTACTCCAGACGGGTTTT
CTTGTTCCTCCAGCCTAAGTGCTCTGAGCCTGGATGAGCCATTTATACAG
AAAGATGTAGAATTAAGAATCATGCCTCCAGTTCAGGAAAACGACAATGG
GAATGAAACTGAATCAGAACAGCCTGAGGAATCAAATGAAAACCAGGATA
AGAGGTAGAAAAGCCTGACTCTGAAAAAGACTTATTAGATGATTCTGAT
GACGATGATATTGAAATATTAGAAGAATGTATTATTTCAGCCATGCCAAC
AAAGTCATCACGCAAAGCCAAAAAACTAGCCCAGACTGCTTCAAAATTAC
CTCCACCTGTGGCAAGGAAACCAAGTCAGCTACCTGTGTATAAACTTCTG
CCAGCACAGAATAGGCTGCAGGCACAAAAACATGTTAGCTTTACACCAGG
GGATGATGTGCCCCGGGTGTACTGTGTAGAAGGGACACCTATAAACTTTT
CCACAGCAACGTCTCTAAGTGATCTGACAATAGAGTCCCCTCCAAATGAA
TTGGCTACTGGAGATGGGGTCAGAGCGGGTATACAGTCAGGTGAATTTGA
AAAACGAGATACCATTCCTACAGAAGGCAGAAGTACAGATGATGCTCAGC
GAGGAAAAATCTCATCTATAGTTACACCAGACCTGGATGACAACAAAGCA
GAGGAAGGAGATATTCTTGCAGAATGTATCAATTCTGCTATGCCCAAAGG
AAAAAGCCACAAGCCTTTCCGAGTGAAAAAGATAATGGACCAAGTCCAAC
AAGCATCCTCGACTTCATCTGGAGCTAACAAAAATCAAGTAGACACTAAG
AAAAAGAAGCCTACTCACCAGTAAAGCCCATGCCACAAAATACTGAATAT
AGAACGCGTGTGAGAAAGAATACAGACTCAAAAGTTAATGTAAATACTGA
AGAAACTTTCTCAGACAACAAAGACTCAAAGAAACCAAGCTTACAAACCA
ATGCCAAGGCCTTCAATGAAAAGCTACCTAACAATGAAGACAGAGTGCGG
GGGAGCTTCGCCTTGGACTCACCGCATCACTACACCCCTATTGAGGGGAC
GCCGTACTGCTTTTCCCGAAATGACTCCTTGAGTTCTCTGGATTTTGATG
ATGACGATGTTGACCTTTCCAGGGAAAAGGCCGAGTTAAGAAAGGGCAAA
GAAAGCAAGGATTCCGAAGCCAAAGTTACCTGCCGCCCAGAACCAAACTC
AAGCCAGCAGGCAGCTAGTAAGTCACAAGCCAGTATAAAACATCCAGCAA
ACAGAGCACAGTCCAAACCAGTGCTGCAGAAACAGCCCACTTTCCCCCAG
TCCTCCAAAGACGGACCAGATAGAGGGGCAGCAACTGACGAAAAACTGCA
GAATTTTGCTATTGAAAATACTCCAGTTTGCTTTTCTCGAAATTCCTCTC
TGAGTTCCCTTAGTGACATTGACCAGGAAAACAACAATAACAAAGAAAGT
GAACCAATCAAAGAAGCTGAACCTGCCAACTCACAAGGAGAGCCCAGTAA
GCCTCAGGCATCCGGGTATGCTCCCAAGTCCTTCCACGTCGAAGACACCC
CTGTCTGTTTCTCAAGAAACAGCTCTCTCAGTTCTCTTAGCATTGACTCT
GAGGACGACCTGTTACAGGAGTGTATAAGTTCTGCCATGCCAAAAAAGAA
AAGGCCTTCAAGACTCAAGAGTGAGAGCGAAAAGCAGAGCCCTAGAAAAG
TGGGTGGCATATTAGCTGAAGACCTGACGCTTGATTTGAAAGATCTACAG
AGGCCAGATTCAGAACACGCTTTCTCCCCCGACTCAGAAAATTTTGACTG
GAAAGCTATTCAGGAAGGCGCAAACTCCATAGTAAGTAGTTTGCACCAAG
CTGCTGCAGCCGCCGCGTGCTTATCTAGACAAGCGTCATCCGACTCAGAT
TCCATTCTGTGACTAAAGTCCGGCATTTCTCTGGGATCGCCTTTTCATCT
TACACCTGATCAAGAGGAAAAGCCATTCACAAGCAATAAAGGCCCAAGAA
TTCTCAAACCTGGAGAGAAAGCACATTAGAAGCAAAAAAAATAGAATCT
GAAAACAAAGGAATCAAAGGCGGGAAAAAGGTTTATAAAAGCTTGATTAC
GGGAAAGATTCGCTCCAATTCAGAAATTTCCAGCCAAATGAAACAACCCC
TCCCGACAAACATGCCTTCAATCTCAAGAGGCAGGACGATGATTCACATC
CCAGGGCTTCGGAATAGCTCCTCTAGTACAAGCCCTGTCTCTAAGAAAGG
CCCACCCCTCAAGACTCCAGCCTCTAAAAGCCCCAGTGAAGGGCCGGGAG
CTACCACTTCTCCTCGAGGAACTAAGCCAGCAGGAAAGTCAGAGCTTAGC
CCTATCACCAGGCAAACTTCCCAAATCAGTGGGTCAAATAAGGGGTCTTC
TAGATCAGGATCTAGAGACTCCACTCCCTCAAGACCTACACAGCAACCAT
TAAGTAGGCCAATGCAGTCTCCAGGGCGAAACTCAATTTCCCCTGGTAGA
```

-continued

```
AATGGAATAAGCCCTCCTAACAAACTGTCTCAGCTGCCCAGAACATCATC

TCCCAGTACTGCTTCAACTAAGTCCTCCGGTTCTGGGAAAATGTCATATA

CATCCCCAGGTAGACAGCTGAGCCAACAAAATCTTACCAAACAAGCAAGT

TTATCCAAGAATGCCAGCAGTATCCCCAGAAGTGAGTCGGCATCTAAAGG

ACTGAATCAGATGAGTAACGGCAATGGGTCAAATAAAAAGGTAGAACTTT

CTAGAATGTCTTCAACTAAATCAAGTGGAAGTGAATCAGACAGATCAGAA

AGGCCTGCATTAGTACGCCAGTCTACTTTCATCAAAGAAGCCCCAAGCCC

AACCCTGAGGAGGAAACTGGAGGAATCTGCCTCATTTGAATCCCTTTCTC

CATCTTCTAGACCAGATTCTCCCACCAGGTCGCAGGCACAGACCCCAGTT

TTAAGCCCTTCCCTTCCTGATATGTCTCTGTCCACACATCCATCTGTTCA

GGCAGGTGGGTGGCGAAAGCTCCCGCCTAATCTCAGCCCCACTATCGAGT

ATAATGACGGAAGGCCCACAAAACGGCATGATATTGCACGCTCCCATTCT

GAAAGTCCTTCCAGACTACCAATCAACCGGGCGGGAACCTGGAAGCGTGA

ACACAGCAAACATTCCTCGTCCCTTCCTCGAGTGAGTACTTGGAGAAGAA

CTGGAAGCTCATCTTCTATTCTTTCTGCTTCATCAGAGTCCAGTGAAAAA

GCAAAAAGTGAGGATGAAAGGCATGTGAGCTCCATGCCAGCACCCAGACA

GATGAAGGAAAACCAGGTGCCCACCAAAGGAACATGGAGGAAAATCAAGG

AAAGTGACATTTCTCCCACAGGCATGGCTTCTCAGAGCGCTTCCTCAGGT

GCTGCCAGTGGTGCTGAATCCAAGCCTCTGATCTATCAGATGGCACCTCC

TGTCTCTAAAACAGAGGATGTTTGGGTGAGAATTGAGGACTGCCCCATTA

ACAACCCTAGATCTGGACGGTCCCCCACAGGCAACACCCCCCCAGTGATT

GACAGTGTTTCAGAGAAGGGAAGTTCAAGCATTAAAGATTCAAAAGACAC

CCATGGGAAACAGAGTGTGGGCAGTGGCAGTCCTGTGCAAACCGTGGGTC

TGGAAACCCGCCTCAACTCCTTTGTTCAGGTAGAGGCCCCAGAACAGAAA

GGAACTGAGGCAAAACCAGGACAGAGTAACCCAGTCTCTATAGCAGAGAC

TGCTGAGACGTGTATAGCAGAGCGTACCCCTTTCAGTTCCAGTAGCTCCA

GCAAGCACAGCTCACCTAGCGGGACTGTTGCTGCCAGAGTGACACCTTTT

AATTACAACCCTAGCCCTAGGAAGAGCAGCGCAGACAGCACTTCAGCCCG

GCCGTCTCAGATCCCTACGCCAGTGAGCACCAACACGAAGAAGAGAGATT

CGAAGACTGACAGCACAGAATCCAGTGGAGCCCAAAGTCCTAAACGCGAT

TCCGGGTCTTACCTCGTGACGTCTGTTTAA
```

This large designated genetic sequence can be truncated for easier data handling. The smaller designated genetic sequence is a subset of nucleotides of the larger designated genetic sequence. The smaller designated genetic sequence contains the informative locations and nucleotides for the assay to be designed. The smaller designated genetic sequence is:

(SEQ ID NO.11)
```
TATCATGTCTCCCGGCTCAAGTCTGCCATCCCTTCACGTTAGGAAACAGA

AAGCTCTAGAAGCTGAGCTAGATGCTCAGCATTTATCAGAAACCTTCGAC

AACATTGACAACCTAAGTCCCAAGGCCTCTCACCGGAGTAAGCAGAGACA

CAAGCAGAATCTTTATGGTGACTATGCTTTTGACGCCAATCGACATGATG

ATAGTAGGTCAGACAATTTCAATACTGGAAACATGACTGTTCTTTCACCA

TATTTAAATACTACGGTATTGCCCAGCTCTTCTTCCTCAAGGGGAAGTTT

AGACAGTTCTCGTTCTGAGAAAGACAGAAGTTTGGAGAGAGAGCGAGGTA

TTGGCCTCAGTGCTTACCATCCAACAACAGAAAATGCAGGAACCTCATCA

AAACGAGGTCTGCAGATCACTACCACTGCAGCCCAGATAGCCAAAGTTAT

GGAAGAAGTATCAGCCATTCATACCTCCCAGGACGACAGAAGTTCTGCTT

CTACCACCGAGTTCCATTGTGTGGCAGACGACAGGAGTGCGGCACGAAGA

AGCTCTGCCTNNNNNNNNNNNNNNNNNNNNNNNNNNNCTTCACTAAGTCGGA

AAATTCAAATAGGACATGCTCTATGCCTTATGCCAAAGTGGAATATAAAC

GATCTTCAAATGACAGTTTAAATA GTGTCACTAGTA
```

Upon identification of the designated genetic sequence two other software programs are utilized. The first of these programs is a blast program that identifies homologies between the designated genetic sequence and the endogenous genome of the mouse, as well as other species.

The second of these programs is repeat masking program, such as Repeat Master Web Server. This program identifies areas in the designated genetic sequence that are highly repetitive, making them less than ideal locations to build a probe. If such areas are found in the designated genetic sequence they are masked by replacing the normal nucleotide designation A, C, G or T with the letter N or X.

An OLIGOS ETC software program is then utilized to generate a bipartite probe. The software allows the screening laboratory 20 to identify secondary structures that may form when designing the bipartite such as heterodimers and homodimers. Results are shown in Table 5.

TABLE 5

Bipartite:

Sequence: CGA TGT GAT TCT ATT GGA aagttAggagagagagcg    (SEQ ID NO. 12)

SEQUENCE:

```
   1    4    7   10   13   16   19    22   25   28   31  34        (SEQ ID NO. 12)
5' CGA  TGT  GAT  TCT  ATT  GGA  aag   ttA  gga  gag  aga gcg 3'
2.69 nM/OD
30.55 ug/OD
MW = 11.3 k (one strand)
Primer to Target Tm(by % GC) 81.0° C.
```

TABLE 5-continued

Bipartite:

COMPOSITION:

| | | |
|---|---|---|
| A | 11.00 | 30.6% |
| C | 3.00 | 8.3% |
| G | 13.00 | 36.1% |
| T | 9.00 | 25.0% |
| X | .00 | 0.0% |
| A + T | 20.00 | 55.6% |
| C + G | 16.00 | 44.4% |

STEM LOOP STRUCTURE:

```
 1|
 |9
  ATCTTAGTGTAGC 5'                           (SEQ ID NO. 13)
T< |||
  TGGAaagttAggagagagagcg 3'                  (SEQ ID NO. 14)
  |19
  17
G = 0.9 kca/lmol
loop Tm 2° C.
```

HOMODIMER:

```
     5' CGATGTGATTCTATTGGAaagttAggagagagagcg 3'   (SEQ ID NO. 12)
        :  |||::|||  :
     3' gcgagagagaggAttgaaAGGTTATCTTAGTGTAGC 5'   (SEQ ID NO. 15)
Homodimer Tm = 8.8° C.
```

A bipartite probe is designed to have one portion hybridize to the designated genetic sequence of the SNP. In this case the bipartite probe would have a sequence of: CGATGTGATTC-TATTGGAaagttAggagagagagcg. (SEQ ID NO. 2). The aagttAggagagagagcg (SEQ ID NO. 16) portion of bipartite indicated hybridizes to the target genetic sequence of the designated genetic sequence which is:

(SEQ ID NO. 11)
TATCATGTCTCCCGGCTCAAGTCTGCCATCCCTTCACGTTAGGAAACAGA

AAGCTCTAGAAGCTGAGCTAGATGCTCAGCATTTATCAGAAACCTTCGAC

AACATTGACAACCTAAGTCCCAAGGCCTCTCACCGGAGTAAGCAGAGACA

CAAGCAGAATCTTTATGGTGACTATGCTTTTGACGCCAATCGACATGATG

ATAGTAGGTCAGACAATTTCAATACTGGAAACATGACTGTTCTTTCACCA

TATTTAAATACTACGGTATTGCCCAGCTCTTCTTCCTCAAGGGGAAGTTT

AGACAGTTCTCGTTCTGAGAAAGACAG<u>AAGTTTGGAGAGAGAGCG</u>AGGTA

TTGGCCTCAGTGCTTACCATCCAACAACAGAAAATGCAGGAACCTCATCA

AAACGAGGTCTGCAGATCACTACCACTGCAGCCCAGATAGCCAAAGTTAT

GGAAGAAGTATCAGCCATTCATACCTCCCAGGACGACAGAAGTTCTGCTT

CTACCACCGAGTTCCATTGTGTGGCAGACGACAGGAGTGCGGCACGAAGA

AGCTCTGCCTNNNNNNNNNNNNNNNNNNNNNNNNNNCTTCACTAAGTCGGA

AAATTCAAATAGGACATGCTCTATGCCTTATGCCAAAGTGGAATATAAAC

GATCTTCAAATGACAGTTTAAATA GTGTCACTAGTA.

Additionally, the CGATGTGATTCTATTGGA (SEQ ID NO. 17) portion of the bipartite probe hybridizes to the Capo35 capture arm of the dendrimer which has a sequence of: 5'-TCC AAT AgA ATC ACA TCg CTT ACA Agg CAA T (SEQ ID NO. 18)

A biological sample in the form of a mouse tail biopsy is submitted via FEDEX (Memphis, Tenn.) overnight delivery service to the screening laboratory 20 from the remote user 1. Each sample occupies one well of a 96-well source well container.

A lysis reagent (made of 2.5 µl of proteinase K (VWR EM-24568-3) and 147.5 µl of Nuclei Lysing Solution (PROMEGA Corporation, Madison, Wis. A7943) per sample)) is gently mixed and poured into a 25 ml trough or reservoir and is placed on the deck of a TECAN GENESIS liquid handling workstation (Research Triangle Park, N.C.). The liquid handler dispenses 150 µl of the lysis reagent in to each sample well of the source well container 2. The well plate is then placed in a 55° C. oven for three hours. The well plate is then placed back on the deck of the TECAN GENESIS liquid handling workstation (Research Triangle Park, N.C.). The liquid handler aspirates 50 pt of each sample and dispenses it into a 384 well primary master well container (FISHER SCIENTIFIC #NC9134044). Once all of the samples are transferred, the primary master well container is moved to the deck of the Isolation Station Purification Station 94.

One-hundred and sixty microliters of SV Lysis reagent (PROMEGA Corporation, Madison Wis., # Z305X), a chaotropic salt, are added to each sample. Next, 30 µl of magnetic particles (PROMEGA Corporation, #A220X) are added and the well components are mixed. The well plate is then moved into the magnetic field of a magnet where the magnetic particles are drawn to the bottom of each well. The supernatant is then aspirated and discarded. Next, the samples are washed three times in 180 µl of 95% ethanol as described above. After the fourth ethanol wash, the microwell container are placed on a 384 tip dryer for 11 minutes. Then the microwell container are moved back to the deck of the liquid handler and 180 µl of hybridization reagent 3.0M Tetramethylammonium Chloride (TMACL), 50 mM Tris, 4 mM EDTA and 0.01% TWEEN 20 polyoxyethylene sorbitan monolaurate (including the dendrimer and bipartite probe) is added to each well at 48° C., the hybridization temperature. In a one-step reaction one hybridization temperature is used which allows for the simultaneous hybridization of bipartite to both the nucleic acid as well as the dendrimer. If the two binding portions of the bipartite are of significant length a two-stage hybridization can occur with first hybridization being more stringent than the second.

The samples incubate at the hybridization temperature for 60 minutes. The well plate is then moved into the magnetic field of a magnet where the magnetic particles are drawn to the bottom of each well. The supernatant is then aspirated and discarded. Next, the samples are washed twice in 180 μl of wash reagent which is composed of 3.0M Tetramethylammonium Chloride (TMACL), 50 mM Tris, 4 mM EDTA and 0.01% TWEEN 20 polyoxyethylene sorbitan monolaurate (without the dendrimer or probe). Next, the samples are washed once in 180 μl of 95% ethanol as described above. The liquid handler dispenses 200 μl of 1×TBE elution reagent into each sample well. The samples are mixed by aspirating and dispensing. The well plate is then moved into the magnetic field of a magnet where the magnetic particles are drawn to the bottom of each well. The supernatant is then aspirated and 130 μl is transferred to a clean optical fluorescent plate. The samples are then placed in a TECAN LSA300 and the fluorescence is detected.

One hundred microliters of the genomic nucleic acid, dendrimer and probe elution is transferred from the fluorescent detection plate to a 384 well optical storage plate (FISHER SCIENTIFIC, #08-772136) for optical density analysis. An $A_{260}$ reading of the storage plate read is performed with a TECAN GENIOS spectrometer (Research Triangle Park, N.C.). This reading shows nucleic acid is present at the desired concentration of 0.5 O.D. units, but a range of 0.1 to 1.5 OD units is acceptable. The results are shown in Table 6.

TABLE 6

| Position | Raw intensity | Background | Net Mean | Net Sum | Results |
|---|---|---|---|---|---|
| 1 1-1:1 | 3,657 | 1,129 | 2,528 | 27,866,350 | WT |
| 5 1-3:1 | 3,326 | 1,048 | 2,277 | 25,104,247 | WT |
| 9 1-5:1 | 3,784 | 1,077 | 2,707 | 29,838,279 | WT |
| 1 1-1:1 | 5,692 | 1,078 | 4,613 | 50,858,087 | KO |
| 5 1-3:1 | 5,278 | 1,117 | 4,160 | 45,863,094 | KO |
| 9 1-5:1 | 5,381 | 1,059 | 4,322 | 47,649,855 | KO |
| 1 1-1:1 | 1,745 | 1,197 | 549 | 6,049,992 | Blanks |
| 5 1-3:1 | 1,715 | 1,141 | 574 | 6,323,344 | Blanks |

Although the present invention has been described and illustrated with respect to preferred embodiments and a preferred use thereof, it is not to be so limited since modifications and changes can be made therein which are within the full scope of the invention.

EXAMPLE 3

Mouse Tissue Genotyping with a Biotin Probe with an Anti-Biotin Dendrimer (Two Stage)

Specifically, a remote user 1 can contact the screening laboratory 20 and provide a description of the mutation. This description may include information such as the endogenous gene Bgal (also known as Glb1) was disrupted with the deletion of a particular exon with a Neomycin cassette. The gene name may be used to query databases to yield literature specific for this mutation by the screening laboratory 20. The Mouse Genome Informatics (MGI) J:38620, PubMed 9063740, or Medline 97217779 databases with their respective journal numbers, yield the following literature reference: Hahn C N; del Pilar Martin M; Schroder M; Vanier M T; Hara Y; Suzuki K; Suzuki K; d'Azzo A, Generalized CNS disease and massive GM1-ganglioside accumulation in mice defective in lysosomal acid beta-galactosidase., Hum Mol Genet 1997 February; 6(2):205-11.

This reference discloses that a Neomycin cassette was inserted into exon six of the Bgal at a AatII restriction site. The screening laboratory 20 would then query a database such as ENSEMBL. The ENSEMBL database gene identification number is ENSMUSG00000042315. The genomic sequence with the exons and restriction sites is identified.

The screening laboratory 20 queries a database such as ENSEMBL. This query yields sequence data, which is the designated genetic sequence. By knowing the endogenous bases that have been deleted, the screening laboratory 20 can take the designated genetic sequence, or portion thereof, and build the probe(s) as to be informative for screening. Moreover, if there are a large number of bases that have been deleted or added, the screening laboratory 20 may probe anywhere inside the sequence.

The Neomycin coding sequence, or mutation sequence, does not naturally occur in mice. The same mechanism of identifying the designated genetic sequence using the National Center for Biotechnology Information database and building anywhere inside the sequence is used. The neomycin coding sequence or designated genetic sequence is:

(SEQ ID NO. 1)
CATTGAACAAGATGGATTGCACGCAGGTTCTCCGGCCGCTTGGGTGGAGA

GGCTATTCGGCTATGACTGGGCACAACAGACAATCGGCTGCTCTGATGCC

GCCGTGTTCCGGCTGTCAGCGCAGGGGCGCCCGGTTCTTTTTGTCAAGAC

CGACCTGTCCGGTGCCCTGAATGAACTGCAGGACGAGGCAGCGCGGCTAT

CGTGGCTGGCCACGACGGGCGTTCCTTGCGCAGCTGTGCTCGACGTTGTC

ACTGAAGCGGGAAGGGACTGGCTGCTATTGGGCGAAGTGCCGGGGCAGGA

TCTCCTGTCATCTCACCTTGCTCCTGCCGAGAAAGTATCCATCATGGCTG

ATGCAATGCGGCGGCTGCATACGCTTGATCCGGCTACCTGCCCATTCGAC

CACCAAGCGAAACATCGCATCGAGCGAGCACGTACTCGGATGGAAGCCGG

TCTTGTCGATCAGGATGATCTGGACGAAGAGCATCAGGGGCTCGCGCCAG

CCGAACTGTTCGCCAGGCTCAAGGCGCGCATGCCCGACGGCGAGGATCTC

GTCGTGACCCATGGCGATGCCTGCTTGCCGAATATCATGGTGGAAAATGG

CCGCTTTTCTGGATTCATCGACTGTGGCCGGCTGGGTGTGGCGGACCGCT

ATCAGGACATAGCGTTGGCTACCCGTGATATTGCTGAAGAGCTTGGCGGC

GAATGGGCTGACCGCTTCCTCGTGCTTTACGGTATCGCCGCTCCCGATTC

GCAGCGCATCGCCTTCTATCGCCTTCTTGACGAGTTCTTCTG

Upon identification of the designated genetic sequence two other software programs are utilized. The first of these programs is a blast program that identifies homologies between the designated genetic sequence and the endogenous genome of the mouse, as well as other species.

The second of these programs is repeat masking program, such as Repeat Master Web Server. This program identifies areas in the designated genetic sequence that are highly repetitive, making them less than ideal locations to build a probe. If such areas are found in the designated genetic sequence they are masked by replacing the normal nucleotide designation A, C, G or T with the letter N or X.

An OLIGOS ETC software program is then utilized to generate a bipartite probe. The software allows the screening laboratory 20 to identify secondary structures that may form when designing the bipartite such as heterodimers and homodimers.

TABLE 7

SEQUENCE:

```
   1   4   7  10  13  16  19  22  25        (SEQ ID NO. 19)
5' tgg aga ggc tat tcg gct atg act g 3'
4.13 nM/OD
32.37 ug/OD
MW = 7.8k (one strand)
Primer to Target Tm(by % GC) = 75.8° C.
```

COMPOSITION:

```
A        5.00                  20.0%
C        4.00                  16.0%
G        9.00                  36.0%
T        7.00                  28.0%
X         .00                   0.0%
A + T   12.00                  48.0%
C + G   13.00                  52.0%
```

STEM LOOP STRUCTURE:

```
  9
 |8
tatcggagaggt 5'                     (SEQ ID NO. 20)
<   ||
tcggctatgactg 3'                    (SEQ ID NO. 21)
  |17
  |6
G = 1.2 k cal/mol
No Stable Secondary Structure
```

HOMODIMER:

No Homodimer

```
                                    (SEQ ID NO. 1)
CATTGAACAAGATGGATTGCACGCAGGTTCTCCGGCCGCTTGGGTGGAGA

GGCTATTCGGCTATGACTGGGCACAACAGACAATCGGCTGCTCTGATGCC

GCCGTGTTCCGGCTGTCAGCGCAGGGGCGCCCGGTTCTTTTTGTCAAGAC

CGACCTGTCCGGTGCCCTGAATGAACTGCAGGACGAGGCAGCGCGGCTAT

CGTGGCTGGCCACGACGGGCGTTCCTTGCGCAGCTGTGCTCGACGTTGTC

ACTGAAGCGGGAAGGGACTGGCTGCTATTGGGCGAAGTGCCGGGGCAGGA

TCTCCTGTCATCTCACCTTGCTCCTGCCGAGAAAGTATCCATCATGGCTG

ATGCAATGCGGCGGCTGCATACGCTTGATCCGGCTACCTGCCCATTCGAC

CACCAAGCGAAACATCGCATCGAGCGAGCACGTACTCGGATGGAAGCCGG

TCTTGTCGATCAGGATGATCTGGACGAAGAGCATCAGGGGCTCGCGCCAG

CCGAACTGTTCGCCAGGCTCAAGGCGCGCATGCCCGACGGCGAGGATCTC

GTCGTGACCCATGGCGATGCCTGCTTGCCGAATATCATGGTGGAAAATGG

CCGCTTTTCTGGATTCATCGACTGTGGCCGGCTGGGTGTGGCGGACCGCT

ATCAGGACATAGCGTTGGCTACCCGTGATATTGCTGAAGAGCTTGGCGGC
```

-continued

```
GAATGGGCTGACCGCTTCCTCGTGCTTTACGGTATCGCCGCTCCCGATTC

GCAGCGCATCGCCTTCTATCGCCTTCTTGACGAGTTCTTCTG
```

A biological sample in the form of a mouse tail biopsy is submitted via FEDEX (Memphis, Tenn.) overnight delivery service to the screening laboratory 20 from the remote user 1. Each sample occupies one well of a 96-well source well container.

A lysis reagent (made of 2.5 µl of proteinase K (VWR EM-24568-3) and 147.5 µl of Nuclei Lysing Solution (PROMEGA Corporation, Madison, Wis. A7943) per sample)) is gently mixed and poured into a 25 ml trough or reservoir and is placed on the deck of a TECAN GENESIS liquid handling workstation (Research Triangle Park, N.C.). The liquid handler dispenses 150 µl of the lysis reagent in to each sample well of the source well container 2. The well plate is then placed in a 55° C. oven for three hours. The well plate is then placed back on the deck of the TECAN GENESIS liquid handling workstation (Research Triangle Park, N.C.). The liquid handler aspirates 50 µl of each sample and dispenses it into a 384 well primary master well container (FISHER SCIENTIFIC #NC9134044). Once all of the samples are transferred, the primary master well container is moved to the deck of the Isolation Station Purification Station 94.

One-hundred and sixty microliters of SV Lysis reagent (PROMEGA Corporation, Madison Wis., # Z305X), a chaotropic salt, are added to each sample. Next, 30 µl of magnetic particles (PROMEGA Corporation, #A220X) are added and the well components are mixed. The well plate is then moved into the magnetic field of a magnet where the magnetic particles are drawn to the bottom of each well. The supernatant is then aspirated and discarded. Next, the samples are washed three times in 180 μl of 95% ethanol as described above. After the fourth ethanol wash, the microwell container are placed on a 384 tip dryer for 11 minutes. Then the microwell container are moved back to the deck of the liquid handler and 180 μl of hybridization reagent 3.0M Tetramethylammonium Chloride (TMACL), 50 mM Tris, 4 mM EDTA and 0.01% TWEEN 20 polyoxyethylene sorbitan monolaurate, 5×Denhardt's (including the biotin probe) is added to each well at 60° C., the hybridization temperature for 60 minutes. The well plate is then moved into the magnetic field of a magnet where the magnetic particles are drawn to the bottom of each well. The supernatant is then aspirated and discarded. Next, 180 μl of anti-biotin dendrimer reagent was added to each sample. The samples were incubated for 10 minutes at 65° C. The supernatant is then aspirated and discarded. Next, the samples are washed once in 180 μl of wash reagent which is composed of 3.0M Tetramethylammonium Chloride (TMACL), 50 mM Tris, 4 mM EDTA and 0.01% TWEEN 20 polyoxyethylene sorbitan monolaurate. The liquid handler dispenses 200 μl of 1×TBE elution reagent into each sample well. The samples are mixed by aspirating and dispensing. The well plate is then moved into the magnetic field of a magnet where the magnetic particles are drawn to the bottom of each well. The supernatant is then aspirated and 130 μl is transferred to a clean optical fluorescent plate. The samples are then placed in a TECAN LSA300 and the fluorescence is detected.

One hundred microliters of the genomic nucleic acid, dendrimer and probe elution is transferred from the fluorescent detection plate to a 384 well optical storage plate (FISHER SCIENTIFIC, #08-772136) for optical density analysis. An $A_{260}$ reading of the storage plate read is performed with a TECAN GENIOS spectrometer (Research Triangle Park, N.C.). This reading shows nucleic acid is present at the desired concentration of 0.5 O.D. units, but a range of 0.1 to 1.5 OD units is acceptable. The results are shown in Table 8.

TABLE 8

| | | Two Stage Anti-Biotin | | | |
|---|---|---|---|---|---|
| Position | Raw intensity | Background | Net Mean | Net Sum | Results |
| 1 1-1:1 | 10205 | 1036 | 9,169 | 101,078,485 | WT |
| 5 1-3:1 | 10753 | 1043 | 9,710 | 107,041,886 | WT |
| 9 1-5:1 | 10698 | 1080 | 9,618 | 106,031,377 | WT |
| 1 1-1:1 | 18520 | 1101 | 17,418 | 192,020,732 | KO |
| 5 1-3:1 | 18724 | 1127 | 17,598 | 193,995,767 | KO |
| 9 1-5:1 | 18852 | 1193 | 17,659 | 194,677,506 | KO |
| 1 1-1:1 | 4504 | 988 | 3,516 | 38,758,638 | Blanks |
| 5 1-3:1 | 4255 | 1057 | 3,198 | 35,251,839 | Blanks |

EXAMPLE 4

Genotyping with a Probe Ligated to a Dendrimer

Specifically, a remote user 1 can contact the screening laboratory 20 and provide a description of the mutation. This description may include information such as the endogenous gene Bgal (also known as Glb1) was disrupted with the deletion of a particular exon with a Neomycin cassette. The gene name may be used to query databases to yield literature specific for this mutation by the screening laboratory 20. The Mouse Genome Informatics (MGI) J:38620, PubMed 9063740, or Medline 97217779 databases with their respective journal numbers, yield the following literature reference: Hahn C N; del Pilar Martin M; Schroder M; Vanier M T; Hara Y; Suzuki K; Suzuki K; d'Azzo A, Generalized CNS disease and massive GM1-ganglioside accumulation in mice defective in lysosomal acid beta-galactosidase., Hum Mol Genet 1997 February; 6(2):205-11.

This reference discloses that a Neomycin cassette was inserted into exon six of the Bgal at a AatII restriction site. The screening laboratory 20 would then query a database such as ENSEMBL. The ENSEMBL database gene identification number is ENSMUSG0000042315. The genomic sequence with the exons and restriction sites is identified.

The screening laboratory 20 queries a database such as ENSEMBL. This query yields sequence data, which is the designated genetic sequence. By knowing the endogenous bases that have been deleted, the screening laboratory 20 can take the designated genetic sequence, or portion thereof, and build the probe(s) as to be informative for screening. Moreover, if there are a large number of bases that have been deleted or added, the screening laboratory 20 may probe anywhere inside the sequence.

The Neomycin coding sequence, or mutation sequence, does not naturally occur in mice. The same mechanism of identifying the designated genetic sequence using the National Center for Biotechnology Information database and building anywhere inside the sequence is used. The neomycin coding sequence or designated genetic sequence is:

```
                                              (SEQ ID NO. 1)
CATTGAACAAGATGGATTGCACGCAGGTTCTCCGGCCGCTTGGGTGGAGA

GGCTATTCGGCTATGACTGGGCACAACAGACAATCGGCTGCTCTGATGCC

GCCGTGTTCCGGCTGTCAGCGCAGGGGCGCCCGGTTCTTTTTGTCAAGAC

CGACCTGTCCGGTGCCCTGAATGAACTGCAGGACGAGGCAGCGCGGCTAT

CGTGGCTGGCCACGACGGGCGTTCCTTGCGCAGCTGTGCTCGACGTTGTC

ACTGAAGCGGGAAGGGACTGGCTGCTATTGGGCGAAGTGCCGGGGCAGGA

TCTCCTGTCATCTCACCTTGCTCCTGCCGAGAAAGTATCCATCATGGCTG

ATGCAATGCGGCGGCTGCATACGCTTGATCCGGCTACCTGCCCATTCGAC

CACCAAGCGAAACATCGCATCGAGCGAGCACGTACTCGGATGGAAGCCGG

TCTTGTCGATCAGGATGATCTGGACGAAGAGCATCAGGGGCTCGCGCCAG

CCGAACTGTTCGCCAGGCTCAAGGCGCGCATGCCCGACGGCGAGGATCTC

GTCGTGACCCATGGCGATGCCTGCTTGCCGAATATCATGGTGGAAAATGG

CCGCTTTTCTGGATTCATCGACTGTGGCCGGCTGGGTGTGGCGGACCGCT

ATCAGGACATAGCGTTGGCTACCCGTGATATTGCTGAAGAGCTTGGCGGC

GAATGGGCTGACCGCTTCCTCGTGCTTTACGGTATCGCCGCTCCCGATTC

GCAGCGCATCGCCTTCTATCGCCTTCTTGACGAGTTCTTCTG
```

Upon identification of the designated genetic sequence two other software programs are utilized. The first of these programs is a blast program that identifies homologies between the designated genetic sequence and the endogenous genome of the mouse, as well as other species.

The second of these programs is repeat masking program, such as Repeat Master Web Server. This program identifies areas in the designated genetic sequence that are highly repetitive, making them less than ideal locations to build a probe. If such areas are found in the designated genetic sequence they are masked by replacing the normal nucleotide designation A, C, G or T with the letter N or X.

OLIGOS ETC software program is then utilized to generate a bipartite probe. The software allows the screening laboratory 20 to identify secondary structures that may form when designing the bipartite such as heterodimers and homodimers

TABLE 9

SEQUENCE:

5'tgg aga ggc tat tcg gct atg act g 3'    (SEQ ID NO. 19)
3.32 nM/OD
33.13 ug/OD
MW = 10.0k (one strand)
Primer to Target Tm(by % GC) = 79.6° C.

COMPOSITION:

| | | |
|---|---|---|
| A | 5.00 | 15.6% |
| C | 5.00 | 15.6% |
| G | 10.00 | 31.3% |
| T | 12.00 | 37.5% |
| X | .00 | 0.0% |
| A + T | 17.00 | 53.1% |
| C + G | 15.00 | 46.9% |

STEM LOOP STRUCTURE:

```
   9
  |8
tatcggagaggt 5'                (SEQ ID NO. 20)
<  ||
tcggctatgactgTTTTTCg 3'        (SEQ ID NO. 22)
  |17
   16
```
G = 1.2 kcal/mol
No Stable Secondary Structure

HOMODIMER:

No Homodimer

---

The biotin probe is designed to bind to the target genetic sequence of the designated genetic sequence which is:

(SEQ ID NO. 1)
CATTGAACAAGATGGATTGCACGCAGGTTCTCCGGCCGCTTGGGTGGAGA

GGCTATTCGGCTATGACTGGGCACAACAGACAATCGGCTGCTCTGATGCC

GCCGTGTTCCGGCTGTCAGCGCAGGGGCGCCCGGTTCTTTTTGTCAAGAC

CGACCTGTCCGGTGCCCTGAATGAACTGCAGGACGAGGCAGCGCGGCTAT

CGTGGCTGGCCACGACGGGCGTTCCTTGCGCAGCTGTGCTCGACGTTGTC

ACTGAAGCGGGAAGGGACTGGCTGCTATTGGGCGAAGTGCCGGGGCAGGA

TCTCCTGTCATCTCACCTTGCTCCTGCCGAGAAAGTATCCATCATGGCTG

ATGCAATGCGGCGGCTGCATACGCTTGATCCGGCTACCTGCCCATTCGAC

CACCAAGCGAAACATCGCATCGAGCGAGCACGTACTCGGATGGAAGCCGG

TCTTGTCGATCAGGATGATCTGGACGAAGAGCATCAGGGGCTCGCGCCAG

CCGAACTGTTCGCCAGGCTCAAGGCGCGCATGCCCGACGGCGAGGATCTC

GTCGTGACCCATGGCGATGCCTGCTTGCCGAATATCATGGTGGAAAATGG

CCGCTTTTCTGGATTCATCGACTGTGGCCGGCTGGGTGTGGCGGACCGCT

ATCAGGACATAGCGTTGGCTACCCGTGATATTGCTGAAGAGCTTGGCGGC

GAATGGGCTGACCGCTTCCTCGTGCTTTACGGTATCGCCGCTCCCGATTC

GCAGCGCATCGCCTTCTATCGCCTTCTTGACGAGTTCTTCTG

A biological sample in the form of a mouse tail biopsy is submitted via FEDEX (Memphis, Tenn.) overnight delivery service to the screening laboratory 20 from the remote user 1. Each sample occupies one well of a 96-well source well container.

A lysis reagent (made of 2.5 t of proteinase K (VWR EM-24568-3) and 147.5 µl of Nuclei Lysing Solution (PROMEGA Corporation, Madison, Wis. A7943) per sample)) is gently mixed and poured into a 25 ml trough or reservoir and is placed on the deck of a TECAN GENESIS liquid handling workstation (Research Triangle Park, N.C.). The liquid handler dispenses 150 µl of the lysis reagent in to each sample well of the source well container 2. The well plate is then placed in a 55° C. oven for three hours. The well plate is then placed back on the deck of the TECAN GENESIS liquid handling workstation (Research Triangle Park, N.C.). The liquid handler aspirates 50 pt of each sample and dispenses it into a 384 well primary master well container (FISHER SCIENTIFIC #NC9134044). Once all of the samples are transferred, the primary master well container is moved to the deck of the Isolation Station Purification Station 94.

One-hundred and sixty microliters of SV Lysis reagent (PROMEGA Corporation, Madison Wis., # Z305X), a chaotropic salt, are added to each sample. Next, 30 µl of magnetic particles (PROMEGA Corporation, #A220X) are added and the well components are mixed. The well plate is then moved into the magnetic field of a magnet where the magnetic particles are drawn to the bottom of each well. The supernatant is then aspirated and discarded. Next, the samples are washed three times in 180 µl of 95% ethanol as described above. After the fourth ethanol wash, the microwell container are placed on a 384 tip dryer for 11 minutes. Then the microwell container are moved back to the deck of the liquid handler and 180 µl of hybridization reagent 3.0M Tetramethylammonium Chloride (TMACL), 50 mM Tris, 4 mM EDTA and 0.1% SDS, 5×Denhardt's (including the fluorescent dendrimer with ligated probe) is added to each well at 60° C., the hybridization temperature for 60 minutes. The well plate is then moved into the magnetic field of a magnet where the magnetic particles are drawn to the bottom of each well. The supernatant is then aspirated and discarded. Next, the samples are washed 4× in 180 μl of wash reagent which is composed of 3.0 M Tetramethylammonium Chloride (TMACL), 50 mM Tris, 4 mM EDTA and 0.1% SDS. The samples are then washed one time with 180 μl of 95% EtOH. The supernatant is then aspirated and discarded. The liquid handler dispenses 200 μl of 1×TBE elution reagent into each sample well. The samples are mixed by aspirating and dispensing. The well plate is then moved into the magnetic field of a magnet where the magnetic particles are drawn to the bottom of each well. The supernatant is then aspirated and 130 μl is transferred to a clean optical fluorescent plate. The samples are then placed in a TECAN LSA300 and the fluorescence is detected.

One hundred microliters of the genomic nucleic acid, dendrimer and probe elution is transferred from the fluorescent detection plate to a 384 well optical storage plate (FISHER SCIENTIFIC, #08-772136) for optical density analysis. An $A_{260}$ reading of the storage plate read is performed with a TECAN GENIOS spectrometer (Research Triangle Park, NC). This reading shows nucleic acid is present at the desired concentration of 0.5 O.D. units, but a range of 0.1 to 1.5 OD units is acceptable. The data is shown in Table 10.

TABLE 10

| | Ligated Dimer Dendrimer | | | | |
|---|---|---|---|---|---|
| Position | Raw intensity | Background | Net intensity | Net intensity | Results |
| 1 1-1:1 | 2,563 | 1,224 | 1,339 | 14,765,015 | WT |
| 5 1-3:1 | 2,393 | 949 | 1,444 | 15,923,444 | WT |
| 9 1-5:1 | 2,436 | 972 | 1,464 | 16,136,454 | WT |
| 1 1-1:1 | 3,118 | 1,104 | 2,014 | 22,203,551 | KO |
| 5 1-3:1 | 3,083 | 960 | 2,123 | 23,401,818 | KO |
| 9 1-5:1 | 3,067 | 941 | 2,126 | 23,435,652 | KO |
| 5 1-3:1 | 1,853 | 914 | 938 | 10,345,690 | Blank |
| 9 1-5:1 | 1,890 | 1,046 | 844 | 9,308,969 | Blank |

Although the present invention has been described and illustrated with respect to preferred embodiments and a preferred use thereof, it is not to be so limited since modifications and changes can be made therein which are within the full scope of the invention.

I claim:

1. A method for detecting a nucleic acid sequence comprising:
   treating a mammalian sample to obtain cellular debris including genomic nucleic acid;
   mixing said cellular debris and a plurality of magnetically-responsive particles under conditions to facilitate reversible immobilization of said genomic nucleic acid to said plurality of magnetically-responsive particles, wherein said magnetically-responsive particles have a coating of glass microfiber;
   removing the portion of said cellular debris not reversibly immobilized to any of said magnetically-responsive particles;
   adding to said magnetic particles under hybridizing conditions nucleic acid probes capable of hybridizing to a portion of said genomic nucleic acid resulting in hybridized nucleic acid probes and unhybridized nucleic acid probes;
   removing said unhybridized nucleic acid probes; and
   detecting said hybridized nucleic acid probes.

2. The method of claim 1 further comprising:
   eluting said genomic nucleic acid from said plurality of magnetically-responsive particles.

3. The method of claim 1 wherein said nucleic acid probes are ligated to a dendrimer.

4. The method of claim 3 further comprising the steps of:
   releasing said dendrimer from said nucleic acid probes; and
   detecting said dendrimer in solution.

5. The method of claim 1 wherein said nucleic acid probes react with elements on a dendrimer.

6. The method of claim 1 wherein said hybridized nucleic acid probes are disassociated from said genomic nucleic acid prior to detecting in solution.

7. The method of claim 1 wherein said mammalian sample is embryonic.

8. An assay for a nucleic acid sequence comprising:

treating a mammalian sample to obtain cellular debris including genomic nucleic acid;

mixing said cellular debris and a plurality of magnetically-responsive particles under conditions that facilitate reversible immobilization of said genomic nucleic acid to said plurality of magnetically-responsive particles, wherein said magnetically-responsive particles have a coating of glass microfiber;

removing the portion of said cellular debris not reversibly immobilized to any of said magnetically-responsive particles;

eluting said nucleic acid from said plurality of magnetically-responsive particles;

adding nucleic acid probes capable of hybridizing to a portion of said genomic nucleic acid under hybridizing conditions to form genomic nucleic acid-nucleic acid probe duplexes while in solution;

adding a plurality of magnetically-responsive particles to bind the genomic nucleic acid-nucleic acid probe duplexes while in solution;

removing unbound nucleic acid probes from said solution;

eluting said genomic nucleic acid-nucleic acid probe from said plurality of magnetically-responsive particles; and detecting hybridized nucleic acid probes in said solution.

9. The assay of claim 8 wherein said nucleic acid probes are ligated to a dendrimer.

10. The assay of claim 9 wherein said nucleic acid probes are reactive with elements on said dendrimer.

11. The method of claim 9 further comprising the steps of:

releasing said dendrimer from said nucleic acid probes; and detecting said dendrimer in solution.

12. The assay of claim 8 wherein said hybridized nucleic acid probes are disassociated from said genomic nucleic acid prior to detecting in solution.

13. The assay of claim 8 wherein said mammalian sample is embryonic.

\* \* \* \* \*